(12) United States Patent
Barchen et al.

(10) Patent No.: US 12,357,767 B2
(45) Date of Patent: Jul. 15, 2025

(54) PARTIAL DOOR CLOSURE PREVENTION SPRING

(71) Applicant: West Pharma. Services IL, Ltd., Ra'anana (IL)

(72) Inventors: Lior Barchen, Gani Tal (IL); Yossi Bar-El, Beit Arye (IL)

(73) Assignee: WEST PHARMA. SERVICES IL, ltd., Ra'anana (IL)

( * ) Notice: Subject to any disclaimer, the term of this patent is extended or adjusted under 35 U.S.C. 154(b) by 7 days.

(21) Appl. No.: 18/211,061

(22) Filed: Jun. 16, 2023

(65) Prior Publication Data
US 2023/0330351 A1   Oct. 19, 2023

Related U.S. Application Data

(62) Division of application No. 16/321,557, filed as application No. PCT/US2016/068049 on Dec. 21, 2016, now Pat. No. 11,730,892.

(60) Provisional application No. 62/369,505, filed on Aug. 1, 2016.

(51) Int. Cl.
*A61M 5/32* (2006.01)
*A61M 5/14* (2006.01)
*E05B 65/00* (2006.01)

(52) U.S. Cl.
CPC ............ *A61M 5/3202* (2013.01); *A61M 5/14* (2013.01); *E05B 65/00* (2013.01); *A61M 2209/06* (2013.01)

(58) Field of Classification Search
CPC .. A61M 5/3202; A61M 2209/06; E05B 65/00
See application file for complete search history.

(56) References Cited

U.S. PATENT DOCUMENTS

| | | | |
|---|---|---|---|
| 232,432 | A | 9/1880 | Allison |
| 1,125,887 | A | 1/1915 | Schimmel |
| 1,321,550 | A | 11/1919 | Platt |
| 1,704,921 | A | 3/1929 | Nicoll |
| 1,795,530 | A | 3/1931 | Watson |
| 1,795,630 | A | 3/1931 | Wilson |
| 2,453,590 | A | 11/1948 | Poux |

(Continued)

FOREIGN PATENT DOCUMENTS

| | | |
|---|---|---|
| CA | 832729 | 1/1970 |
| CA | 2832729 A1 | 10/2012 |

(Continued)

OTHER PUBLICATIONS

US 8,333,733 B2, 12/2012, Lanigan (withdrawn)

(Continued)

*Primary Examiner* — Jessica Arble
*Assistant Examiner* — Hans Kaliher
(74) *Attorney, Agent, or Firm* — Blank Rome LLP

(57) ABSTRACT

A method for visually indicating that a door of a drug delivery device is open is described. A closing force to move the door is received. Then, it is detected that the door is not closed. A biasing element pushes the door to a perceptibly open position with an opening force when the door reaches the last 30 degrees of rotation of toward closure or when the door reaches the last 30% of range of movement during the rotation of the door. The perceptibly open position of the door is indicated relative to a drug delivery device housing.

18 Claims, 16 Drawing Sheets

(56) References Cited

U.S. PATENT DOCUMENTS

| | | |
|---|---|---|
| 2,589,426 A | 3/1952 | Ogle |
| 2,677,373 A | 5/1954 | Barradas |
| 2,702,547 A | 2/1955 | Glass |
| 2,860,635 A | 11/1958 | Wilburn |
| 3,002,754 A | 10/1961 | Dombrowski |
| 3,203,269 A | 8/1965 | Perrine |
| 3,212,685 A | 10/1965 | Swan |
| 3,585,439 A | 6/1971 | Schneeberger |
| 3,623,474 A | 11/1971 | Heilman |
| 3,689,748 A | 9/1972 | Bothne |
| 3,705,582 A | 12/1972 | Stumpf |
| 3,708,945 A | 1/1973 | Klettke |
| 3,782,365 A | 1/1974 | Pinna |
| 3,794,028 A | 2/1974 | Mueller |
| 3,834,387 A | 9/1974 | Brown |
| 3,946,732 A | 3/1976 | Hurscham |
| 3,994,295 A | 11/1976 | Wulff |
| 4,026,128 A | 5/1977 | Blanco |
| 4,082,094 A | 4/1978 | Dailey |
| 4,085,747 A | 4/1978 | St. Jacques |
| 4,126,132 A | 11/1978 | Portner |
| 4,167,663 A | 9/1979 | Granzow, Jr. |
| 4,189,065 A | 2/1980 | Wolf-Dietrich |
| 4,195,636 A | 4/1980 | Behnke |
| 4,218,724 A | 8/1980 | Kaufman |
| 4,222,380 A | 9/1980 | Terayama |
| 4,241,381 A | 12/1980 | Cobaugh |
| 4,254,768 A | 3/1981 | Ty |
| 4,270,537 A | 6/1981 | Romaine |
| 4,273,122 A | 6/1981 | Whitney |
| 4,276,879 A | 7/1981 | Yiournas |
| 4,300,554 A | 11/1981 | Hessberg |
| 4,322,668 A | 3/1982 | Trussler |
| 4,324,262 A | 4/1982 | Hall |
| 4,396,385 A | 8/1983 | Kelly |
| 4,403,987 A | 9/1983 | Gottinger |
| 4,425,120 A | 1/1984 | Sampson |
| 4,435,173 A | 3/1984 | Siposs |
| 4,465,478 A | 8/1984 | Sabelman |
| 4,497,036 A | 1/1985 | Dunn |
| 4,502,488 A | 3/1985 | Degironimo |
| 4,504,263 A | 3/1985 | Steuer |
| 4,549,554 A | 10/1985 | Markham |
| 4,564,054 A | 1/1986 | Gustavsson |
| 4,565,543 A | 1/1986 | Bekkering |
| 4,583,974 A | 4/1986 | Kokernak |
| 4,585,439 A | 4/1986 | Michel |
| 4,599,082 A | 7/1986 | Grimard |
| 4,601,702 A | 7/1986 | Hudson |
| 4,634,426 A | 1/1987 | Kamen |
| 4,636,201 A | 1/1987 | Ambrose |
| 4,645,326 A | 2/1987 | Kiuchi |
| 4,664,654 A | 5/1987 | Strauss |
| 4,667,299 A | 5/1987 | Dunn |
| 4,685,903 A | 8/1987 | Cable |
| 4,689,043 A | 8/1987 | Bisha |
| 4,695,274 A | 9/1987 | Fox |
| 4,698,055 A | 10/1987 | Sealfon |
| 4,702,738 A | 10/1987 | Spencer |
| 4,704,105 A | 11/1987 | Adorjan |
| 4,710,178 A | 12/1987 | Henri |
| 4,729,208 A | 3/1988 | Galy |
| 4,735,311 A | 4/1988 | Lowe |
| 4,737,144 A | 4/1988 | Choksi |
| 4,772,272 A | 9/1988 | McFarland |
| 4,781,688 A | 11/1988 | Thoma |
| 4,810,215 A | 3/1989 | Kaneko |
| 4,810,249 A | 3/1989 | Haber |
| 4,813,426 A | 3/1989 | Haber |
| 4,840,185 A | 6/1989 | Hernandez |
| 4,850,966 A | 7/1989 | Grau |
| 4,861,341 A | 8/1989 | Woodburn |
| 4,863,434 A | 9/1989 | Bayless |
| 4,867,743 A | 9/1989 | Vaillancourt |
| 4,874,383 A | 10/1989 | McNaughton |
| 4,882,575 A | 11/1989 | Kawahara |
| 4,886,499 A | 12/1989 | Cirelli |
| 4,892,521 A | 1/1990 | Laico |
| 4,897,083 A | 1/1990 | Martell |
| 4,900,310 A | 2/1990 | Ogle, II |
| 4,908,014 A | 3/1990 | Kroyer |
| 4,915,702 A | 4/1990 | Haber |
| 4,919,569 A | 4/1990 | Siegfried |
| 4,919,596 A | 4/1990 | Slate |
| 4,923,446 A | 5/1990 | Page |
| 4,929,241 A | 5/1990 | Kulli |
| 4,950,235 A | 8/1990 | Slate |
| 4,950,241 A | 8/1990 | Ranford |
| 4,950,246 A | 8/1990 | Muller |
| 4,957,490 A | 9/1990 | Byrne |
| 4,964,866 A | 10/1990 | Szwarc |
| 4,994,045 A | 2/1991 | Ranford |
| 4,998,924 A | 3/1991 | Ranford |
| 5,019,051 A | 5/1991 | Hake |
| 5,034,004 A | 7/1991 | Crankshaw |
| 5,051,109 A | 9/1991 | Simon |
| 5,062,828 A | 11/1991 | Waltz |
| D322,671 S | 12/1991 | Szwarc |
| 5,088,988 A | 2/1992 | Talonn |
| 5,089,783 A | 2/1992 | Kapsokavathis |
| 5,090,877 A | 2/1992 | D'Silva |
| 5,097,122 A | 3/1992 | Colman |
| 5,107,685 A | 4/1992 | Kobayashi |
| 5,109,850 A | 5/1992 | Blanco |
| 5,112,317 A | 5/1992 | Michel |
| 5,114,406 A | 5/1992 | Gabriel |
| 5,127,910 A | 7/1992 | Talonn |
| 5,131,816 A | 7/1992 | Brown |
| 5,147,326 A | 9/1992 | Talonn |
| 5,156,599 A | 10/1992 | Ranford |
| 5,190,521 A | 3/1993 | Hubbard |
| 5,211,638 A | 5/1993 | Dudar |
| 5,217,437 A | 6/1993 | Talonn |
| 5,246,670 A | 9/1993 | Haber |
| 5,254,096 A | 10/1993 | Rondelet |
| 5,267,977 A | 12/1993 | Feeney, Jr. |
| 5,269,762 A | 12/1993 | Armbruster |
| 5,275,582 A | 1/1994 | Wimmer |
| 5,282,593 A | 2/1994 | Fast |
| 5,295,966 A | 3/1994 | Stern |
| 5,298,023 A | 3/1994 | Haber |
| 5,300,045 A | 4/1994 | Plassche, Jr. |
| 5,318,522 A | 6/1994 | D'Antonio |
| 5,338,311 A | 8/1994 | Mahurkar |
| 5,342,313 A | 8/1994 | Campbell |
| 5,346,086 A | 9/1994 | Harris |
| 5,348,543 A | 9/1994 | Talley |
| 5,348,544 A | 9/1994 | Sweeney |
| 5,354,287 A | 10/1994 | Wacks |
| 5,364,364 A | 11/1994 | Kasvikis |
| 5,366,498 A | 11/1994 | Brannan |
| 5,376,785 A | 12/1994 | Chin |
| 5,383,865 A | 1/1995 | Michel |
| D356,150 S | 3/1995 | Duggan |
| 5,411,482 A | 5/1995 | Campbell |
| 5,415,645 A | 5/1995 | Friend |
| 5,430,636 A | 7/1995 | Kachi |
| 5,445,621 A | 8/1995 | Poli |
| 5,456,360 A | 10/1995 | Griffin |
| 5,478,315 A | 12/1995 | Brothers |
| 5,478,316 A | 12/1995 | Bitdinger |
| 5,482,446 A | 1/1996 | Williamson |
| 5,496,274 A | 3/1996 | Graves |
| 5,501,665 A | 3/1996 | Jhuboo |
| 5,505,709 A | 4/1996 | Funderburk |
| 5,527,287 A | 6/1996 | Miskinyar |
| D372,098 S | 7/1996 | Lattin |
| 5,558,639 A | 9/1996 | Gangemi |
| 5,562,624 A | 10/1996 | Righi |
| 5,562,686 A | 10/1996 | Sauer |
| 5,563,479 A | 10/1996 | Suzuki |
| 5,593,390 A | 1/1997 | Castellano |
| 5,609,580 A | 3/1997 | Kwiatkowski |
| 5,611,785 A | 3/1997 | Mito |

(56) References Cited

U.S. PATENT DOCUMENTS

| | | |
|---|---|---|
| 5,616,132 A | 4/1997 | Newman |
| 5,624,400 A | 4/1997 | Firth |
| 5,637,095 A | 6/1997 | Nason |
| 5,640,071 A | 6/1997 | Malaspina |
| 5,643,218 A | 7/1997 | Lynn |
| 5,645,530 A | 7/1997 | Boukhny |
| 5,645,955 A | 7/1997 | Maglica |
| 5,647,853 A | 7/1997 | Feldmann |
| 5,658,133 A | 8/1997 | Anderson |
| 5,658,256 A | 8/1997 | Shields |
| 5,661,372 A | 8/1997 | Ishimaru |
| 5,662,678 A | 9/1997 | Macklin |
| 5,672,160 A | 9/1997 | Oesterlind |
| D384,745 S | 10/1997 | Lattin |
| 5,683,367 A | 11/1997 | Jordan |
| 5,690,618 A | 11/1997 | Smith |
| 5,697,908 A | 12/1997 | Imbert |
| 5,697,916 A | 12/1997 | Schraga |
| 5,709,662 A | 1/1998 | Olive |
| 5,725,500 A | 3/1998 | Micheler |
| 5,728,075 A | 3/1998 | Levander |
| D393,314 S | 4/1998 | Meisner |
| 5,741,227 A | 4/1998 | Sealfon |
| 5,741,275 A | 4/1998 | Wyssmann |
| 5,766,186 A | 6/1998 | Faraz |
| 5,776,103 A | 7/1998 | Kriesel |
| 5,779,676 A | 7/1998 | Kriesel |
| 5,795,675 A | 8/1998 | Maglica |
| 5,800,420 A | 9/1998 | Gross |
| 5,807,375 A | 9/1998 | Gross |
| 5,810,167 A | 9/1998 | Fujii |
| 5,810,784 A | 9/1998 | Tamaro |
| 5,814,020 A | 9/1998 | Gross |
| 5,820,406 A | 10/1998 | Hetherington |
| 5,830,187 A | 11/1998 | Kriesel |
| 5,836,920 A | 11/1998 | Robertson |
| 5,839,537 A | 11/1998 | Nishino |
| 5,848,991 A | 12/1998 | Gross |
| 5,851,197 A | 12/1998 | Marano |
| 5,858,001 A | 1/1999 | Tsals |
| 5,858,008 A | 1/1999 | Capaccio |
| 5,868,710 A | 2/1999 | Battiato |
| 5,884,237 A | 3/1999 | Kanki |
| 5,893,842 A | 4/1999 | Imbert |
| 5,894,015 A | 4/1999 | Rechtin |
| 5,919,167 A | 7/1999 | Mulhauser |
| 5,925,018 A | 7/1999 | Ungerstedt |
| 5,926,596 A | 7/1999 | Edwards |
| 5,931,814 A | 8/1999 | Alex |
| 5,941,850 A | 8/1999 | Shah |
| 5,944,699 A | 8/1999 | Barrelle |
| 5,948,392 A | 9/1999 | Haslwanter |
| 5,954,697 A | 9/1999 | Srisathapat |
| 5,957,895 A | 9/1999 | Sage |
| 5,968,011 A | 10/1999 | Larsen |
| 5,989,221 A | 11/1999 | Hjertman |
| 5,993,423 A | 11/1999 | Choi |
| 5,997,501 A | 12/1999 | Gross |
| 6,004,296 A | 12/1999 | Jansen |
| 6,004,297 A | 12/1999 | Steenfeldt-Jensen |
| 6,033,245 A | 3/2000 | Yamkovoy |
| 6,033,377 A | 3/2000 | Rasmussen |
| 6,039,713 A | 3/2000 | Botich |
| 6,045,533 A | 4/2000 | Kriesel |
| 6,064,797 A | 5/2000 | Crittendon |
| 6,074,369 A | 6/2000 | Sage |
| 6,081,098 A | 6/2000 | Bertness |
| 6,117,575 A | 9/2000 | Dinsdale |
| 6,138,865 A | 10/2000 | Gilmore |
| 6,139,399 A | 10/2000 | Deangelis |
| 6,149,614 A | 11/2000 | Dunshee |
| 6,160,487 A | 12/2000 | Deluca |
| 6,162,197 A | 12/2000 | Mohammad |
| 6,175,688 B1 | 1/2001 | Cassidy |
| 6,186,979 B1 | 2/2001 | Dysarz |
| 6,186,982 B1 | 2/2001 | Gross |
| 6,189,292 B1 | 2/2001 | Odell |
| 6,200,289 B1 | 3/2001 | Hochman |
| 6,200,296 B1 | 3/2001 | Dibiasi |
| 6,224,569 B1 | 5/2001 | Brimhall |
| 6,248,093 B1 | 6/2001 | Moberg |
| 6,270,478 B1 | 8/2001 | Morton |
| 6,270,481 B1 | 8/2001 | Mason |
| 6,277,095 B1 | 8/2001 | Kriesel |
| 6,277,098 B1 | 8/2001 | Klitmose |
| 6,277,099 B1 | 8/2001 | Strowe |
| 6,287,283 B1 | 9/2001 | Ljunggreen |
| 6,293,925 B1 | 9/2001 | Safabash |
| 6,302,633 B1 | 10/2001 | Poe |
| 6,305,908 B1 | 10/2001 | Hermann |
| 6,331,762 B1 | 12/2001 | Bertness |
| 6,336,729 B1 | 1/2002 | Pavelle |
| 6,345,968 B1 | 2/2002 | Shupe |
| 6,362,591 B1 | 3/2002 | Moberg |
| 6,377,848 B1 | 4/2002 | Garde |
| 6,391,005 B1 | 5/2002 | Lum |
| 6,423,029 B1 | 7/2002 | Elsberry |
| 6,423,035 B1 | 7/2002 | Das |
| 6,423,036 B1 | 7/2002 | Van Huizen |
| D461,243 S | 8/2002 | Niedospial, Jr. |
| D465,026 S | 10/2002 | May |
| 6,458,102 B1 | 10/2002 | Mann |
| 6,471,436 B1 | 10/2002 | Gjata |
| 6,485,461 B1 | 11/2002 | Mason |
| 6,485,465 B2 | 11/2002 | Moberg |
| 6,500,150 B1 | 12/2002 | Gross |
| 6,503,231 B1 | 1/2003 | Prausnitz |
| 6,511,336 B1 | 1/2003 | Turek |
| 6,517,517 B1 | 2/2003 | Farrugia |
| D471,274 S | 3/2003 | Diaz |
| D471,983 S | 3/2003 | Hippolyte |
| 6,530,901 B1 | 3/2003 | Tsukada |
| 6,554,800 B1 | 4/2003 | Nezhadian |
| 6,555,986 B2 | 4/2003 | Moberg |
| 6,558,351 B1 | 5/2003 | Steil |
| 6,558,365 B2 | 5/2003 | Zinger |
| 6,565,541 B2 | 5/2003 | Sharp |
| 6,585,695 B1 | 7/2003 | Adair |
| 6,589,229 B1 | 7/2003 | Connelly |
| 6,595,205 B2 | 7/2003 | Andersson |
| 6,595,956 B1 | 7/2003 | Gross |
| 6,595,960 B2 | 7/2003 | West |
| 6,599,272 B1 | 7/2003 | Hjertman |
| 6,632,201 B1 | 10/2003 | Mathias |
| 6,645,181 B1 | 11/2003 | Lavi |
| 6,652,482 B2 | 11/2003 | Hochman |
| 6,656,158 B2 | 12/2003 | Dwayne |
| 6,656,159 B2 | 12/2003 | Flaherty |
| 6,659,980 B2 | 12/2003 | Moberg |
| 6,673,033 B1 | 1/2004 | Sciulli |
| 6,679,862 B2 | 1/2004 | Diaz |
| 6,685,678 B2 | 2/2004 | Evans |
| 6,689,118 B2 | 2/2004 | Alchas |
| 6,699,218 B2 | 3/2004 | Flaherty |
| 6,719,141 B2 | 4/2004 | Heinz |
| 6,722,916 B2 | 4/2004 | Buccinna |
| 6,736,796 B2 | 5/2004 | Shekalim |
| 6,743,211 B1 | 6/2004 | Prausnitz |
| 6,749,587 B2 | 6/2004 | Flaherty |
| 6,752,783 B2 | 6/2004 | Hung |
| 6,752,787 B1 | 6/2004 | Causey, III |
| 6,767,336 B1 | 7/2004 | Kaplan |
| 6,768,425 B2 | 7/2004 | Flaherty |
| 6,786,890 B2 | 9/2004 | Preuthun |
| 6,800,071 B1 | 10/2004 | McConnell |
| 6,805,687 B2 | 10/2004 | Dextradeur |
| 6,817,990 B2 | 11/2004 | Yap |
| 6,824,529 B2 | 11/2004 | Gross |
| 6,830,558 B2 | 12/2004 | Flaherty |
| 6,843,782 B2 | 1/2005 | Gross |
| 6,851,197 B2 | 2/2005 | Terry |
| 6,854,620 B2 | 2/2005 | Ramey |
| 6,905,298 B1 | 6/2005 | Haring |
| 6,907,679 B2 | 6/2005 | Yarborough |

(56) References Cited

U.S. PATENT DOCUMENTS

| | | |
|---|---|---|
| 6,908,452 B2 | 6/2005 | Diaz |
| 6,910,138 B2 | 6/2005 | Hayashi |
| 6,933,693 B2 | 8/2005 | Schuchmann |
| 6,943,531 B2 | 9/2005 | Fukaya |
| 6,950,028 B2 | 9/2005 | Zweig |
| 6,960,192 B1 | 11/2005 | Flaherty |
| 6,972,002 B2 | 12/2005 | Thorne |
| 6,979,316 B1 | 12/2005 | Rubin |
| 6,997,727 B1 | 2/2006 | Legrady |
| 7,001,360 B2 | 2/2006 | Veasey |
| 7,004,104 B1 | 2/2006 | Kundus |
| 7,004,929 B2 | 2/2006 | McWethy |
| 7,025,226 B2 | 4/2006 | Ramey |
| 7,033,338 B2 | 4/2006 | Vilks |
| 7,034,223 B2 | 4/2006 | Fan |
| 7,048,715 B2 | 5/2006 | Diaz |
| 7,054,737 B2 | 5/2006 | Degner |
| 7,060,054 B2 | 6/2006 | Nissels |
| 7,060,059 B2 | 6/2006 | Keith |
| 7,063,684 B2 | 6/2006 | Moberg |
| 7,064,454 B2 | 6/2006 | Fukaya |
| 7,066,909 B1 | 6/2006 | Peter |
| 7,075,311 B1 | 7/2006 | Oshiro |
| 7,094,221 B2 | 8/2006 | Veasey |
| 7,097,637 B2 | 8/2006 | Triplett |
| 7,112,187 B2 | 9/2006 | Karlsson |
| 7,122,982 B2 | 10/2006 | Sasaya |
| 7,124,310 B2 | 10/2006 | Hayashi |
| 7,126,341 B2 | 10/2006 | Bertness |
| 7,127,288 B2 | 10/2006 | Sturman |
| 7,128,727 B2 | 10/2006 | Flaherty |
| 7,144,384 B2 | 12/2006 | Gorman |
| 7,193,521 B2 | 3/2007 | Moberg |
| 7,214,209 B2 | 5/2007 | Mazzoni |
| D544,092 S | 6/2007 | Lewis |
| 7,225,694 B2 | 6/2007 | Said |
| 7,247,149 B2 | 7/2007 | Beyerlein |
| 7,247,150 B2 | 7/2007 | Bierman |
| 7,250,037 B2 | 7/2007 | Shermer |
| 7,267,669 B2 | 9/2007 | Staunton |
| RE39,923 E | 11/2007 | Blom |
| 7,291,132 B2 | 11/2007 | DeRuntz |
| 7,291,159 B2 | 11/2007 | Schmelzeisen-Redeker |
| 7,292,462 B2 | 11/2007 | Watanabe |
| 7,303,549 B2 | 12/2007 | Flaherty |
| 7,306,578 B2 | 12/2007 | Gray |
| 7,326,194 B2 | 2/2008 | Zinger |
| 7,344,385 B2 | 3/2008 | Chen |
| 7,364,570 B2 | 4/2008 | Gerondale |
| 7,377,907 B2 | 5/2008 | Shekalim |
| 7,377,912 B2 | 5/2008 | Graf |
| 7,384,413 B2 | 6/2008 | Gross |
| 7,390,312 B2 | 6/2008 | Barrelle |
| 7,390,314 B2 | 6/2008 | Stutz, Jr. |
| 7,407,493 B2 | 8/2008 | Mario |
| 7,418,880 B1 | 9/2008 | Smith |
| D578,210 S | 10/2008 | Muta |
| 7,442,186 B2 | 10/2008 | Blomquist |
| 7,455,663 B2 | 11/2008 | Bikovsky |
| 7,459,571 B2 | 12/2008 | Schlitter |
| 7,465,290 B2 | 12/2008 | Reilly |
| 7,468,055 B2 | 12/2008 | Prais |
| 7,488,181 B2 | 2/2009 | Van Haaster |
| 7,497,842 B2 | 3/2009 | Diaz |
| 7,500,963 B2 | 3/2009 | Westbye |
| 7,501,587 B2 | 3/2009 | English |
| 7,503,786 B2 | 3/2009 | Kato |
| 7,524,304 B2 | 4/2009 | Genosar |
| 7,530,964 B2 | 5/2009 | Lavi |
| 7,540,858 B2 | 6/2009 | Dibiasi |
| 7,547,281 B2 | 6/2009 | Hayes |
| 7,563,253 B2 | 7/2009 | Tanner |
| 7,565,208 B2 | 7/2009 | Harris |
| 7,569,050 B2 | 8/2009 | Moberg |
| 7,579,716 B2 | 8/2009 | Sato |
| D600,341 S | 9/2009 | Loerwald |
| 7,585,287 B2 | 9/2009 | Bresina |
| 7,588,559 B2 | 9/2009 | Aravena |
| 7,589,974 B2 | 9/2009 | Grady |
| D602,155 S | 10/2009 | Foley |
| D602,586 S | 10/2009 | Foley |
| 7,597,682 B2 | 10/2009 | Moberg |
| D604,835 S | 11/2009 | Conley |
| 7,611,491 B2 | 11/2009 | Pickhard |
| 7,612,542 B2 | 11/2009 | Eguchi |
| 7,621,893 B2 | 11/2009 | Moberg |
| 7,628,770 B2 | 12/2009 | Ethelfeld |
| 7,628,772 B2 | 12/2009 | McConnell |
| 7,628,782 B2 | 12/2009 | Adair |
| 7,637,891 B2 | 12/2009 | Wall |
| 7,637,899 B2 | 12/2009 | Woolston |
| 7,641,649 B2 | 1/2010 | Moberg |
| 7,642,787 B2 | 1/2010 | Bertness |
| 7,658,734 B2 | 2/2010 | Adair |
| 7,660,627 B2 | 2/2010 | McNichols |
| 7,678,079 B2 | 3/2010 | Shermer |
| 7,682,338 B2 | 3/2010 | Griffin |
| 7,686,787 B2 | 3/2010 | Moberg |
| 7,690,456 B2 | 4/2010 | Deng |
| 7,692,399 B2 | 4/2010 | Harriman |
| 7,699,829 B2 | 4/2010 | Harris |
| 7,699,833 B2 | 4/2010 | Moberg |
| 7,704,088 B2 | 4/2010 | Sakamoto |
| 7,704,227 B2 | 4/2010 | Moberg |
| 7,704,229 B2 | 4/2010 | Moberg |
| 7,704,231 B2 | 4/2010 | Pongpairochana |
| 7,705,602 B2 | 4/2010 | Bertness |
| 7,708,717 B2 | 5/2010 | Estes |
| 7,713,238 B2 | 5/2010 | Mernoe |
| 7,713,240 B2 | 5/2010 | Istoc |
| 7,717,903 B2 | 5/2010 | Estes |
| 7,717,913 B2 | 5/2010 | Novak |
| 7,722,574 B2 | 5/2010 | Toman |
| 7,736,333 B2 | 6/2010 | Gillespie, III |
| 7,736,344 B2 | 6/2010 | Moberg |
| 7,740,600 B2 | 6/2010 | Slatkine |
| 7,744,589 B2 | 6/2010 | Mounce |
| 7,749,194 B2 | 7/2010 | Edwards |
| 7,753,879 B2 | 7/2010 | Mernoe |
| 7,758,548 B2 | 7/2010 | Gillespie |
| 7,758,550 B2 | 7/2010 | Bollenbach |
| 7,766,867 B2 | 8/2010 | Lynch |
| 7,766,873 B2 | 8/2010 | Moberg |
| 7,776,030 B2 | 8/2010 | Estes |
| 7,780,636 B2 | 8/2010 | Radmer |
| 7,780,637 B2 | 8/2010 | Jerde |
| 7,789,857 B2 | 9/2010 | Moberg |
| 7,789,862 B2 | 9/2010 | Thorne, Jr. |
| 7,794,426 B2 | 9/2010 | Briones |
| 7,794,427 B2 | 9/2010 | Estes |
| 7,801,599 B2 | 9/2010 | Young |
| 7,806,868 B2 | 10/2010 | De Polo |
| 7,815,622 B2 | 10/2010 | Istoc |
| 7,828,528 B2 | 11/2010 | Estes |
| 7,837,659 B2 | 11/2010 | Bush, Jr. |
| 7,846,132 B2 | 12/2010 | Gravesen |
| 7,854,723 B2 | 12/2010 | Hwang |
| 7,857,131 B2 | 12/2010 | Vedrine |
| 7,879,025 B2 | 2/2011 | Jacobson |
| 7,879,026 B2 | 2/2011 | Estes |
| 7,892,206 B2 | 2/2011 | Moberg |
| 7,901,382 B2 | 3/2011 | Daily |
| 7,905,867 B2 | 3/2011 | Veasey |
| 7,918,825 B2 | 4/2011 | O'Connor |
| 7,918,843 B2 | 4/2011 | Genosar |
| 7,935,104 B2 | 5/2011 | Yodfat |
| 7,935,105 B2 | 5/2011 | Miller |
| 7,938,803 B2 | 5/2011 | Mernoe |
| 7,955,297 B2 | 6/2011 | Radmer |
| 7,955,305 B2 | 6/2011 | Moberg |
| 7,967,784 B2 | 6/2011 | Pongpairochana |
| 7,967,795 B1 | 6/2011 | Cabiri |
| 7,976,514 B2 | 7/2011 | Abry |
| 7,981,105 B2 | 7/2011 | Adair |

(56) References Cited

U.S. PATENT DOCUMENTS

| | | |
|---|---|---|
| 7,988,683 B2 | 8/2011 | Adair |
| 7,993,300 B2 | 8/2011 | Nyholm |
| 7,993,301 B2 | 8/2011 | Boyd |
| 7,998,111 B2 | 8/2011 | Moberg |
| 7,998,116 B2 | 8/2011 | Mernoe |
| 7,998,117 B2 | 8/2011 | Gross |
| 7,998,131 B2 | 8/2011 | Adair |
| 8,002,752 B2 | 8/2011 | Yodfat |
| 8,002,754 B2 | 8/2011 | Kawamura |
| 8,008,892 B2 | 8/2011 | Kikuchi |
| 8,021,357 B2 | 9/2011 | Tanaka |
| 8,025,658 B2 | 9/2011 | Chong |
| 8,029,459 B2 | 10/2011 | Rush |
| 8,029,460 B2 | 10/2011 | Rush |
| 8,029,469 B2 | 10/2011 | Ethelfeld |
| 8,034,019 B2 | 10/2011 | Nair |
| 8,034,026 B2 | 10/2011 | Grant |
| 8,038,648 B2 | 10/2011 | Marksteiner |
| 8,038,666 B2 | 10/2011 | Triplett |
| 8,057,431 B2 | 11/2011 | Woehr |
| 8,057,436 B2 | 11/2011 | Causey |
| 8,062,253 B2 | 11/2011 | Nielsen |
| 8,062,255 B2 | 11/2011 | Brunnberg |
| 8,062,257 B2 | 11/2011 | Moberg |
| 8,062,259 B2 | 11/2011 | Nycz |
| 8,065,096 B2 | 11/2011 | Moberg |
| 8,066,694 B2 | 11/2011 | Wagener |
| D650,079 S | 12/2011 | Presta |
| D650,903 S | 12/2011 | Kosinski |
| 8,086,306 B2 | 12/2011 | Katzman |
| D652,503 S | 1/2012 | Cameron, III |
| 8,105,279 B2 | 1/2012 | Mernoe |
| 8,105,293 B2 | 1/2012 | Pickhard |
| 8,114,046 B2 | 2/2012 | Covino |
| 8,114,064 B2 | 2/2012 | Alferness |
| 8,114,066 B2 | 2/2012 | Naef |
| 8,118,781 B2 | 2/2012 | Knopper |
| 8,121,603 B2 | 2/2012 | Zhi |
| D657,462 S | 4/2012 | Siroky |
| 8,147,446 B2 | 4/2012 | Yodfat |
| 8,151,169 B2 | 4/2012 | Bieth |
| 8,152,764 B2 | 4/2012 | Istoc |
| 8,152,770 B2 | 4/2012 | Reid |
| 8,152,779 B2 | 4/2012 | Cabiri |
| 8,152,793 B2 | 4/2012 | Antti |
| 8,157,693 B2 | 4/2012 | Waksmundzki |
| 8,157,769 B2 | 4/2012 | Cabiri |
| 8,162,674 B2 | 4/2012 | Cho |
| 8,162,923 B2 | 4/2012 | Adams |
| 8,167,841 B2 | 5/2012 | Teisen-Simony |
| 8,172,591 B2 | 5/2012 | Wertz |
| 8,172,804 B2 | 5/2012 | Bikovsky |
| 8,177,749 B2 | 5/2012 | Slate |
| 8,182,447 B2 | 5/2012 | Moberg |
| 8,182,462 B2 | 5/2012 | Istoc |
| 8,197,444 B1 | 6/2012 | Bazargan |
| 8,206,296 B2 | 6/2012 | Jennewine |
| 8,206,351 B2 | 6/2012 | Sugimoto |
| 8,221,356 B2 | 7/2012 | Enggaard |
| 8,221,359 B2 | 7/2012 | Kristensen |
| 8,226,607 B2 | 7/2012 | Carter |
| 8,226,608 B2 | 7/2012 | Mernoe |
| 8,234,769 B2 | 8/2012 | Leidig |
| 8,257,345 B2 | 9/2012 | Adair |
| 8,267,893 B2 | 9/2012 | Moberg |
| 8,267,921 B2 | 9/2012 | Yodfat |
| 8,273,061 B2 | 9/2012 | McConnell |
| 8,287,520 B2 | 10/2012 | Drew |
| 8,292,647 B1 | 10/2012 | McGrath |
| 8,303,572 B2 | 11/2012 | Adair |
| 8,308,679 B2 | 11/2012 | Hanson |
| 8,308,695 B2 | 11/2012 | Laiosa |
| 8,323,250 B2 | 12/2012 | Chong |
| 8,348,898 B2 | 1/2013 | Cabiri |
| 8,361,028 B2 | 1/2013 | Gross |
| 8,366,668 B2 | 2/2013 | Maritan |
| 8,372,039 B2 | 2/2013 | Mernoe |
| 8,373,421 B2 | 2/2013 | Lindegger |
| 8,409,141 B2 | 4/2013 | Johansen |
| 8,409,142 B2 | 4/2013 | Causey |
| 8,409,143 B2 | 4/2013 | Lanigan |
| 8,409,149 B2 | 4/2013 | Hommann |
| 8,414,533 B2 | 4/2013 | Alexandersson |
| 8,414,557 B2 | 4/2013 | Istoc |
| 8,425,468 B2 | 4/2013 | Weston |
| 8,430,847 B2 | 4/2013 | Mernoe |
| D685,083 S | 6/2013 | Schneider |
| 8,465,455 B2 | 6/2013 | Cabiri |
| 8,469,942 B2 | 6/2013 | Kow |
| D687,141 S | 7/2013 | Schneider |
| 8,474,332 B2 | 7/2013 | Bente, IV |
| 8,475,408 B2 | 7/2013 | Mernoe |
| 8,479,595 B2 | 7/2013 | Vazquez |
| 8,483,980 B2 | 7/2013 | Moberg |
| 8,490,790 B2 | 7/2013 | Cocheteux |
| 8,493,022 B2 | 7/2013 | Bertness |
| 8,495,918 B2 | 7/2013 | Bazargan |
| 8,496,862 B2 | 7/2013 | Zelkovich |
| D687,536 S | 8/2013 | Guarraia |
| 8,500,716 B2 | 8/2013 | Adair |
| 8,512,287 B2 | 8/2013 | Cindrich |
| 8,512,295 B2 | 8/2013 | Evans |
| 8,517,987 B2 | 8/2013 | Istoc |
| 8,517,992 B2 | 8/2013 | Jones |
| 8,523,803 B1 | 9/2013 | Favreau |
| D692,552 S | 10/2013 | Lovell |
| 8,551,046 B2 | 10/2013 | Causey |
| 8,556,856 B2 | 10/2013 | Bazargan |
| 8,562,364 B2 | 10/2013 | Lin |
| 8,568,361 B2 | 10/2013 | Yodfat |
| 8,574,216 B2 | 11/2013 | Istoc |
| 8,603,026 B2 | 12/2013 | Favreau |
| 8,603,027 B2 | 12/2013 | Favreau |
| 8,603,028 B2 | 12/2013 | Mudd |
| 8,617,110 B2 | 12/2013 | Moberg |
| 8,622,966 B2 | 1/2014 | Causey |
| 8,628,510 B2 | 1/2014 | Bazargan |
| 8,632,499 B2 | 1/2014 | Grant |
| 8,647,074 B2 | 2/2014 | Moberg |
| 8,647,296 B2 | 2/2014 | Moberg |
| 8,647,303 B2 | 2/2014 | Cowe |
| 8,668,672 B2 | 3/2014 | Moberg |
| 8,674,288 B2 | 3/2014 | Hanson |
| 8,679,060 B2 | 3/2014 | Mernoe |
| 8,679,062 B2 | 3/2014 | Yodfat |
| 8,681,010 B2 | 3/2014 | Moberg |
| D702,834 S | 4/2014 | Norton |
| 8,690,855 B2 | 4/2014 | Alderete, Jr. |
| 8,708,961 B2 | 4/2014 | Field |
| 8,715,237 B2 | 5/2014 | Moberg |
| 8,721,603 B2 | 5/2014 | Lundquist |
| 8,751,237 B2 | 6/2014 | Kubota |
| 8,753,326 B2 | 6/2014 | Chong |
| 8,753,331 B2 | 6/2014 | Murphy |
| 8,764,707 B2 | 7/2014 | Moberg |
| 8,764,723 B2 | 7/2014 | Chong |
| 8,771,222 B2 | 7/2014 | Kanderian, Jr. |
| 8,777,896 B2 | 7/2014 | Starkweather |
| 8,777,924 B2 | 7/2014 | Kanderian, Jr. |
| 8,777,925 B2 | 7/2014 | Patton |
| 8,784,369 B2 | 7/2014 | Starkweather |
| 8,784,370 B2 | 7/2014 | Lebel |
| 8,784,378 B2 | 7/2014 | Weinandy |
| 8,790,295 B1 | 7/2014 | Sigg |
| 8,795,224 B2 | 8/2014 | Starkweather |
| 8,795,231 B2 | 8/2014 | Chong |
| 8,795,260 B2 | 8/2014 | Drew |
| 8,801,668 B2 | 8/2014 | Ali |
| 8,801,679 B2 | 8/2014 | Iio |
| 8,808,230 B2 | 8/2014 | Rotstein |
| 8,808,269 B2 | 8/2014 | Bazargan |
| 8,810,394 B2 | 8/2014 | Kalpin |
| 8,814,379 B2 | 8/2014 | Griffiths |
| 8,845,587 B2 | 9/2014 | Lanigan |

(56) References Cited

U.S. PATENT DOCUMENTS

| | | |
|---|---|---|
| 8,858,508 B2 | 10/2014 | Lavi |
| 8,864,739 B2 | 10/2014 | Moberg |
| 8,870,818 B2 | 10/2014 | Alderete, Jr. |
| 8,876,770 B2 | 11/2014 | Kraft |
| 8,876,778 B2 | 11/2014 | Carrel |
| 8,911,410 B2 | 12/2014 | Ekman |
| 8,915,882 B2 | 12/2014 | Cabiri |
| 8,915,886 B2 | 12/2014 | Cowe |
| 8,920,374 B2 | 12/2014 | Bokelman |
| 8,932,266 B2 | 1/2015 | Wozencroft |
| D723,157 S | 2/2015 | Clemente |
| 8,945,051 B2 | 2/2015 | Schriver |
| 8,979,802 B2 | 3/2015 | Woehr |
| 8,986,250 B2 | 3/2015 | Beebe |
| 8,992,475 B2 | 3/2015 | Mann |
| 9,011,164 B2 | 4/2015 | Filman |
| 9,011,371 B2 | 4/2015 | Moberg |
| 9,011,387 B2 | 4/2015 | Ekman |
| 9,033,924 B2 | 5/2015 | Yavorsky |
| 9,033,925 B2 | 5/2015 | Moberg |
| 9,050,406 B2 | 6/2015 | Kow |
| 9,061,104 B2 | 6/2015 | Daniel |
| 9,061,110 B2 | 6/2015 | Avery |
| 9,072,827 B2 | 7/2015 | Cabiri |
| 9,072,845 B2 | 7/2015 | Hiles |
| 9,089,475 B2 | 7/2015 | Fangrow |
| 9,089,641 B2 | 7/2015 | Kavazov |
| 9,107,999 B2 | 8/2015 | Moberg |
| 9,138,534 B2 | 9/2015 | Yodfat |
| 9,149,575 B2 | 10/2015 | Cabiri |
| 9,173,996 B2 | 11/2015 | Gray |
| 9,173,997 B2 | 11/2015 | Gross |
| 9,180,248 B2 | 11/2015 | Moberg |
| 9,205,188 B2 | 12/2015 | Lanigan |
| 9,205,199 B2 | 12/2015 | Kemp |
| D747,799 S | 1/2016 | Norton |
| 9,233,215 B2 | 1/2016 | Hourmand |
| 9,242,044 B2 | 1/2016 | Markussen |
| 9,259,532 B2 | 2/2016 | Cabiri |
| 9,283,327 B2 | 3/2016 | Hourmand |
| 9,308,318 B2 | 4/2016 | Lanigan |
| 9,308,324 B2 * | 4/2016 | Shaanan ............... G08B 21/02 |
| 9,308,327 B2 | 4/2016 | Marshall |
| 9,314,569 B2 | 4/2016 | Causey |
| 9,320,849 B2 | 4/2016 | Smith |
| 9,327,073 B2 | 5/2016 | Moberg |
| 9,339,607 B2 | 5/2016 | Langley |
| 9,345,834 B2 | 5/2016 | Henley |
| 9,345,836 B2 | 5/2016 | Cabiri |
| 9,350,634 B2 | 5/2016 | Fadell |
| 9,352,090 B2 | 5/2016 | Brereton |
| 9,364,606 B2 | 6/2016 | Cindrich |
| 9,364,608 B2 | 6/2016 | Moberg |
| 9,381,300 B2 | 7/2016 | Smith |
| 9,393,365 B2 | 7/2016 | Cabiri |
| 9,393,369 B2 | 7/2016 | Cabiri |
| 9,421,321 B2 | 8/2016 | Hanson |
| 9,421,323 B2 | 8/2016 | Cabiri |
| 9,421,337 B2 | 8/2016 | Kemp |
| 9,427,531 B2 | 8/2016 | Hourmand |
| 9,433,732 B2 | 9/2016 | Moberg |
| 9,433,733 B2 | 9/2016 | Moberg |
| 9,446,188 B2 | 9/2016 | Grant |
| 9,446,196 B2 | 9/2016 | Hourmand |
| 9,452,261 B2 | 9/2016 | Alon |
| D768,288 S | 10/2016 | Sean |
| 9,463,280 B2 | 10/2016 | Cabiri |
| 9,463,889 B2 | 10/2016 | Schmitz |
| 9,468,720 B2 | 10/2016 | Mudd |
| 9,474,859 B2 | 10/2016 | Ekman |
| 9,492,610 B2 | 11/2016 | Cabiri |
| 9,492,618 B2 | 11/2016 | Day |
| 9,492,622 B2 | 11/2016 | Brereton |
| D774,640 S | 12/2016 | Tyce |
| 9,511,190 B2 | 12/2016 | Cabiri |
| 9,522,234 B2 | 12/2016 | Cabiri |
| D776,262 S | 1/2017 | Tyce |
| D776,263 S | 1/2017 | Tyce |
| D776,264 S | 1/2017 | Tyce |
| D776,265 S | 1/2017 | Tyce |
| 9,539,384 B2 | 1/2017 | Servansky |
| 9,539,388 B2 | 1/2017 | Causey |
| 9,539,757 B2 | 1/2017 | Ramirez |
| 9,572,926 B2 | 2/2017 | Cabiri |
| 9,572,927 B2 | 2/2017 | Ulrich |
| 9,579,452 B2 | 2/2017 | Adair |
| 9,579,471 B2 | 2/2017 | Carrel |
| 9,610,407 B2 | 4/2017 | Bruggemann |
| 9,656,019 B2 | 5/2017 | Cabiri |
| 9,656,021 B2 | 5/2017 | Brereton |
| 9,656,025 B2 | 5/2017 | Anders |
| 9,707,335 B2 | 7/2017 | Agard |
| 9,707,356 B2 | 7/2017 | Hourmand |
| D794,776 S | 8/2017 | Tyce |
| 9,737,655 B2 | 8/2017 | Clemente |
| 9,744,306 B2 | 8/2017 | Cowe |
| 9,775,948 B2 | 10/2017 | Bechmann |
| 9,782,545 B2 | 10/2017 | Gross |
| 9,789,247 B2 | 10/2017 | Kamen |
| 9,802,030 B2 | 10/2017 | Clemente |
| D804,019 S | 11/2017 | Costello |
| 9,814,830 B2 | 11/2017 | Mernoe |
| 9,814,832 B2 | 11/2017 | Agard |
| 9,814,839 B2 | 11/2017 | Eaton |
| D804,650 S | 12/2017 | Costello |
| D805,186 S | 12/2017 | Costello |
| D805,187 S | 12/2017 | Costello |
| D805,188 S | 12/2017 | Costello |
| D805,189 S | 12/2017 | Costello |
| D805,190 S | 12/2017 | Costello |
| 9,849,242 B2 | 12/2017 | Henley |
| 9,861,759 B2 | 1/2018 | Gross |
| 9,862,519 B2 | 1/2018 | Deutschle |
| D810,278 S | 2/2018 | Cabiri |
| D810,279 S | 2/2018 | Cabiri |
| D811,583 S | 2/2018 | Cabiri |
| D811,584 S | 2/2018 | Cabiri |
| D817,481 S | 5/2018 | Cabiri |
| 9,999,722 B2 | 6/2018 | Yodfat |
| 10,010,681 B2 | 7/2018 | Koch |
| 10,071,196 B2 | 9/2018 | Cabiri |
| 10,076,356 B2 | 9/2018 | Hadvary |
| 10,143,794 B2 | 12/2018 | Lanigan |
| 10,149,943 B2 | 12/2018 | Bar-El |
| D838,367 S | 1/2019 | Norton |
| 10,166,335 B2 | 1/2019 | Reber |
| 10,207,048 B2 | 2/2019 | Gray |
| 10,207,051 B2 | 2/2019 | Cereda |
| 10,227,161 B2 | 3/2019 | Auerbach |
| 10,232,116 B2 | 3/2019 | Ekman |
| 10,258,740 B2 | 4/2019 | McLoughlin |
| D851,752 S | 6/2019 | Nazzaro |
| 10,376,641 B2 | 8/2019 | Hirschel |
| 10,376,647 B2 | 8/2019 | Farris |
| 10,434,262 B2 | 10/2019 | Bendek |
| D865,945 S | 11/2019 | Nazzaro |
| 10,500,352 B2 | 12/2019 | Grant |
| 10,561,798 B2 | 2/2020 | Holland |
| 10,569,012 B2 * | 2/2020 | Schabbach ........ A61M 5/14244 |
| 10,576,213 B2 | 3/2020 | Gylleby |
| 10,576,220 B2 | 3/2020 | Armes |
| 10,583,260 B2 | 3/2020 | Kemp |
| 10,603,430 B2 | 3/2020 | Shor |
| 10,722,645 B2 | 7/2020 | Kamen |
| 10,729,847 B2 | 8/2020 | Gray |
| 10,758,679 B2 | 9/2020 | Bar-El |
| 10,765,808 B2 | 9/2020 | Day |
| 10,842,942 B2 | 11/2020 | Iibuchi |
| 11,027,059 B2 | 6/2021 | Niklaus |
| 2001/0005781 A1 | 6/2001 | Bergens |
| 2001/0018937 A1 | 9/2001 | Nemoto |
| 2001/0025168 A1 | 9/2001 | Gross |
| 2001/0034502 A1 | 10/2001 | Moberg |
| 2001/0041869 A1 | 11/2001 | Causey |

(56) References Cited

U.S. PATENT DOCUMENTS

| | | |
|---|---|---|
| 2001/0056263 A1 | 12/2001 | Alchas |
| 2002/0010423 A1 | 1/2002 | Gross |
| 2002/0016569 A1 | 2/2002 | Critchlow |
| 2002/0022798 A1 | 2/2002 | Connelly |
| 2002/0026594 A1 | 2/2002 | Hayashi |
| 2002/0029018 A1 | 3/2002 | Jeffrey |
| 2002/0040208 A1 | 4/2002 | Flaherty |
| 2002/0043951 A1 | 4/2002 | Moberg |
| 2002/0045867 A1 | 4/2002 | Nielsen |
| 2002/0055711 A1 | 5/2002 | Lavi |
| 2002/0055718 A1 | 5/2002 | Hunt |
| 2002/0065488 A1 | 5/2002 | Suzuki |
| 2002/0100472 A1 | 8/2002 | Casper |
| 2002/0107487 A1 | 8/2002 | Preuthun |
| 2002/0120186 A1 | 8/2002 | Keimel |
| 2002/0123740 A1 | 9/2002 | Flaherty |
| 2002/0133114 A1 | 9/2002 | Itoh |
| 2002/0151855 A1 | 10/2002 | Douglas |
| 2002/0161332 A1 | 10/2002 | Ramey |
| 2002/0169215 A1 | 11/2002 | Meng |
| 2002/0173748 A1 | 11/2002 | McConnell |
| 2002/0173769 A1 | 11/2002 | Gray |
| 2003/0009133 A1 | 1/2003 | Ramey |
| 2003/0014018 A1 | 1/2003 | Giambattista |
| 2003/0038637 A1 | 2/2003 | Bertness |
| 2003/0050602 A1 | 3/2003 | Pettis |
| 2003/0060765 A1 | 3/2003 | Campbell |
| 2003/0069518 A1 | 4/2003 | Daley |
| 2003/0078195 A1 | 4/2003 | Kristensen |
| 2003/0109827 A1 | 6/2003 | Lavi |
| 2003/0125671 A1 | 7/2003 | Aramata |
| 2003/0130618 A1 | 7/2003 | Gray |
| 2003/0135159 A1 | 7/2003 | Daily |
| 2003/0160683 A1 | 8/2003 | Blomquist |
| 2003/0167035 A1 | 9/2003 | Flaherty |
| 2003/0167039 A1 | 9/2003 | Moberg |
| 2003/0171717 A1 | 9/2003 | Farrugia |
| 2003/0181868 A1 | 9/2003 | Swenson |
| 2003/0199825 A1 | 10/2003 | Flaherty |
| 2003/0199827 A1 | 10/2003 | Thorne |
| 2003/0212370 A1 | 11/2003 | Barrelle |
| 2003/0216683 A1 | 11/2003 | Shekalim |
| 2003/0229308 A1 | 12/2003 | Tsals |
| 2003/0236498 A1 | 12/2003 | Gross |
| 2004/0000818 A1 | 1/2004 | Preuthun |
| 2004/0002682 A1 | 1/2004 | Kovelman |
| 2004/0003493 A1 | 1/2004 | Adair |
| 2004/0008009 A1 | 1/2004 | Fukaya |
| 2004/0010207 A1 | 1/2004 | Flaherty |
| 2004/0015131 A1 | 1/2004 | Flaherty |
| 2004/0030353 A1 | 2/2004 | Schmelzeisen-Redeker |
| 2004/0049160 A1 | 3/2004 | Hsieh |
| 2004/0049161 A1 | 3/2004 | Shearn |
| 2004/0064088 A1 | 4/2004 | Gorman |
| 2004/0082911 A1 | 4/2004 | Tiu |
| 2004/0085215 A1 | 5/2004 | Moberg |
| 2004/0092873 A1 | 5/2004 | Moberg |
| 2004/0116866 A1 | 6/2004 | Gorman |
| 2004/0122359 A1 | 6/2004 | Wenz |
| 2004/0122369 A1 | 6/2004 | Schriver |
| 2004/0127857 A1 | 7/2004 | Shemesh |
| 2004/0135078 A1 | 7/2004 | Mandro |
| 2004/0158172 A1 | 8/2004 | Hancock |
| 2004/0158205 A1 | 8/2004 | Savage |
| 2004/0171983 A1 | 9/2004 | Sparks |
| 2004/0186419 A1 | 9/2004 | Cho |
| 2004/0186424 A1 | 9/2004 | Hjertman |
| 2004/0186441 A1 | 9/2004 | Graf |
| 2004/0195989 A1 | 10/2004 | Harriman |
| 2004/0210196 A1 | 10/2004 | Bush, Jr. |
| 2004/0260233 A1 | 12/2004 | Garibotto |
| 2004/0267199 A1 | 12/2004 | Marshall |
| 2005/0027255 A1 | 2/2005 | Lavi |
| 2005/0033234 A1 | 2/2005 | Sadowski |
| 2005/0038388 A1 | 2/2005 | Hommann |
| 2005/0038391 A1 | 2/2005 | Wittland |
| 2005/0049553 A1 | 3/2005 | Triplett |
| 2005/0065466 A1 | 3/2005 | Vedrine |
| 2005/0065472 A1 | 3/2005 | Cindrich |
| 2005/0070845 A1 | 3/2005 | Faries |
| 2005/0071487 A1 | 3/2005 | Lu |
| 2005/0101912 A1 | 5/2005 | Faust |
| 2005/0113761 A1 | 5/2005 | Faust |
| 2005/0124940 A1 | 6/2005 | Martin |
| 2005/0135078 A1 | 6/2005 | Hamada |
| 2005/0154353 A1 | 7/2005 | Alheidt |
| 2005/0159706 A1 | 7/2005 | Wilkinson |
| 2005/0171476 A1 | 8/2005 | Judson |
| 2005/0171487 A1 | 8/2005 | Haury |
| 2005/0171512 A1 | 8/2005 | Flaherty |
| 2005/0174098 A1 | 8/2005 | Watanabe |
| 2005/0177136 A1 | 8/2005 | Miller |
| 2005/0189923 A1 | 9/2005 | Ohishi |
| 2005/0197626 A1 | 9/2005 | Moberg |
| 2005/0197650 A1 | 9/2005 | Sugimoto |
| 2005/0201050 A1 | 9/2005 | Hayashi |
| 2005/0203461 A1 | 9/2005 | Flaherty |
| 2005/0209768 A1 | 9/2005 | Degner |
| 2005/0238507 A1 | 10/2005 | DiIanni |
| 2005/0245956 A1 | 11/2005 | Steinemann |
| 2005/0258714 A1 | 11/2005 | Henderson |
| 2005/0283114 A1 | 12/2005 | Bresina |
| 2005/0288633 A1 | 12/2005 | Jeffrey |
| 2006/0013716 A1 | 1/2006 | Nason |
| 2006/0017412 A1 | 1/2006 | Sasaya |
| 2006/0030816 A1 | 2/2006 | Zubry |
| 2006/0036216 A1 | 2/2006 | Rimlinger |
| 2006/0095010 A1 | 5/2006 | Westbye |
| 2006/0095014 A1 | 5/2006 | Ethelfeld |
| 2006/0122577 A1 | 6/2006 | Poulsen |
| 2006/0124269 A1 | 6/2006 | Miyazaki |
| 2006/0173406 A1 | 8/2006 | Hayes |
| 2006/0173408 A1 | 8/2006 | Wyrick |
| 2006/0173410 A1 | 8/2006 | Moberg |
| 2006/0173439 A1 | 8/2006 | Thorne, Jr. |
| 2006/0184154 A1 | 8/2006 | Moberg |
| 2006/0195029 A1 | 8/2006 | Shults |
| 2006/0206054 A1 | 9/2006 | Shekalim |
| 2006/0206057 A1 | 9/2006 | Deruntz |
| 2006/0211982 A1 | 9/2006 | Prestrelski |
| 2006/0229569 A1 | 10/2006 | Lavi |
| 2006/0253086 A1 | 11/2006 | Moberg |
| 2006/0264831 A1 | 11/2006 | Skwarek |
| 2006/0264888 A1 | 11/2006 | Moberg |
| 2006/0264889 A1 | 11/2006 | Moberg |
| 2006/0264890 A1 | 11/2006 | Moberg |
| 2006/0264894 A1 | 11/2006 | Moberg |
| 2006/0270987 A1 | 11/2006 | Peter |
| 2006/0283465 A1 | 12/2006 | Nickel |
| 2006/0293722 A1 | 12/2006 | Slatkine |
| 2007/0016381 A1 | 1/2007 | Kamath |
| 2007/0021733 A1 | 1/2007 | Hansen |
| 2007/0025879 A1 | 2/2007 | Vandergaw |
| 2007/0049865 A1 | 3/2007 | Radmer |
| 2007/0073228 A1 | 3/2007 | Mernoe |
| 2007/0079894 A1 | 4/2007 | Kraus |
| 2007/0104596 A1 | 5/2007 | Preuthun |
| 2007/0106218 A1 | 5/2007 | Yodfat |
| 2007/0118405 A1 | 5/2007 | Campbell |
| 2007/0123819 A1 | 5/2007 | Mernoe |
| 2007/0129688 A1 | 6/2007 | Scheurer |
| 2007/0149926 A1 | 6/2007 | Moberg |
| 2007/0167912 A1 | 7/2007 | Causey |
| 2007/0179444 A1 | 8/2007 | Causey |
| 2007/0185449 A1 | 8/2007 | Mernoe |
| 2007/0191770 A1 | 8/2007 | Moberg |
| 2007/0197954 A1 | 8/2007 | Keenan |
| 2007/0197968 A1* | 8/2007 | Pongpairochana ...... A61M 5/34 604/67 |
| 2007/0203454 A1 | 8/2007 | Shermer |
| 2007/0203528 A1 | 8/2007 | Vernon |
| 2007/0212103 A1 | 9/2007 | Kikuchi |
| 2007/0219480 A1 | 9/2007 | Kamen |
| 2007/0233003 A1 | 10/2007 | Radgowski |

(56) References Cited

U.S. PATENT DOCUMENTS

| | | |
|---|---|---|
| 2007/0233038 A1 | 10/2007 | Pruitt |
| 2007/0265568 A1 | 11/2007 | Tsals |
| 2007/0270745 A1 | 11/2007 | Nezhat |
| 2007/0274736 A1 | 11/2007 | Sato |
| 2007/0279011 A1 | 12/2007 | Jones |
| 2007/0282269 A1 | 12/2007 | Carter |
| 2008/0021439 A1 | 1/2008 | Brittingham |
| 2008/0033367 A1 | 2/2008 | Haury |
| 2008/0033369 A1 | 2/2008 | Kohlbrenner |
| 2008/0033393 A1 | 2/2008 | Edwards |
| 2008/0051710 A1 | 2/2008 | Moberg |
| 2008/0051711 A1 | 2/2008 | Mounce |
| 2008/0051727 A1 | 2/2008 | Moberg |
| 2008/0051730 A1 | 2/2008 | Bikovsky |
| 2008/0059133 A1 | 3/2008 | Edwards |
| 2008/0068870 A1 | 3/2008 | Eguchi |
| 2008/0097326 A1 | 4/2008 | Moberg |
| 2008/0097381 A1 | 4/2008 | Moberg |
| 2008/0097387 A1 | 4/2008 | Spector |
| 2008/0099015 A1 | 5/2008 | Pocock |
| 2008/0108951 A1 | 5/2008 | Jerde |
| 2008/0108953 A1 | 5/2008 | Moser |
| 2008/0125700 A1 | 5/2008 | Moberg |
| 2008/0140006 A1 | 6/2008 | Eskuri |
| 2008/0140014 A1 | 6/2008 | Miller |
| 2008/0140018 A1 | 6/2008 | Enggaard |
| 2008/0147004 A1 | 6/2008 | Mann |
| 2008/0156476 A1 | 7/2008 | Smisson |
| 2008/0167641 A1 | 7/2008 | Hansen |
| 2008/0188813 A1 | 8/2008 | Miller |
| 2008/0191556 A1 | 8/2008 | Hong |
| 2008/0195049 A1 | 8/2008 | Thalmann |
| 2008/0208138 A1 | 8/2008 | Lim |
| 2008/0215006 A1 | 9/2008 | Thorkild |
| 2008/0215013 A1 | 9/2008 | Felix-Faure |
| 2008/0215015 A1 | 9/2008 | Cindrich |
| 2008/0221522 A1 | 9/2008 | Moberg |
| 2008/0221523 A1 | 9/2008 | Moberg |
| 2008/0234627 A1 | 9/2008 | Dent |
| 2008/0243087 A1 | 10/2008 | Enggaard |
| 2008/0249473 A1 | 10/2008 | Rutti |
| 2008/0255516 A1 | 10/2008 | Yodfat |
| 2008/0259666 A1 | 10/2008 | Eguchi |
| 2008/0262436 A1 | 10/2008 | Olson |
| 2008/0269687 A1 | 10/2008 | Chong |
| 2008/0269689 A1 | 10/2008 | Edwards |
| 2008/0269723 A1 | 10/2008 | Mastrototaro |
| 2008/0274630 A1 | 11/2008 | Shelton |
| 2008/0275407 A1 | 11/2008 | Scheurer |
| 2008/0275425 A1 | 11/2008 | Strickler |
| 2008/0281270 A1 | 11/2008 | Cross |
| 2008/0287873 A1 | 11/2008 | Liberatore |
| 2008/0294094 A1 | 11/2008 | Mhatre |
| 2008/0294143 A1 | 11/2008 | Tanaka |
| 2008/0306449 A1 | 12/2008 | Kristensen |
| 2008/0312601 A1 | 12/2008 | Cane |
| 2008/0315829 A1 | 12/2008 | Jones |
| 2008/0319383 A1 | 12/2008 | Byland |
| 2008/0319416 A1 | 12/2008 | Yodfat |
| 2009/0012478 A1 | 1/2009 | Weston |
| 2009/0041805 A1 | 2/2009 | Walker |
| 2009/0043245 A1 | 2/2009 | Nguyen |
| 2009/0043253 A1 | 2/2009 | Podaima |
| 2009/0048347 A1 | 2/2009 | Cohen |
| 2009/0048578 A1 | 2/2009 | Adams |
| 2009/0054750 A1 | 2/2009 | Jennewine |
| 2009/0054832 A1 | 2/2009 | Sugimoto |
| 2009/0054852 A1 | 2/2009 | Takano |
| 2009/0062767 A1 | 3/2009 | Van Antwerp |
| 2009/0069784 A1 | 3/2009 | Estes |
| 2009/0076360 A1 | 3/2009 | Brister |
| 2009/0076383 A1 | 3/2009 | Toews |
| 2009/0076453 A1 | 3/2009 | Mejlhede |
| 2009/0088694 A1 | 4/2009 | Carter |
| 2009/0088731 A1 | 4/2009 | Campbell |
| 2009/0093763 A1 | 4/2009 | Gonnelli |
| 2009/0093792 A1 | 4/2009 | Gross |
| 2009/0093793 A1 | 4/2009 | Gross |
| 2009/0099510 A1 | 4/2009 | Poulsen |
| 2009/0105650 A1 | 4/2009 | Wiegel |
| 2009/0105663 A1 | 4/2009 | Brand |
| 2009/0118662 A1 | 5/2009 | Schnall |
| 2009/0124977 A1 | 5/2009 | Jensen |
| 2009/0131860 A1 | 5/2009 | Nielsen |
| 2009/0139724 A1 | 6/2009 | Gray |
| 2009/0143730 A1 | 6/2009 | De Polo |
| 2009/0143735 A1 | 6/2009 | De Polo |
| 2009/0149830 A1 | 6/2009 | Spector |
| 2009/0182277 A1 | 7/2009 | Carter |
| 2009/0182284 A1 | 7/2009 | Morgan |
| 2009/0198215 A1 | 8/2009 | Chong |
| 2009/0204076 A1 | 8/2009 | Liversidge |
| 2009/0209896 A1 | 8/2009 | Selevan |
| 2009/0216103 A1 | 8/2009 | Brister |
| 2009/0234319 A1 | 9/2009 | Marksteiner |
| 2009/0240240 A1 | 9/2009 | Hines |
| 2009/0243234 A1 | 10/2009 | Sharifi |
| 2009/0253973 A1 | 10/2009 | Bashan |
| 2009/0254041 A1 | 10/2009 | Krag |
| 2009/0259176 A1 | 10/2009 | Yairi |
| 2009/0281585 A1 | 11/2009 | Katzman |
| 2009/0299288 A1 | 12/2009 | Sie |
| 2009/0299290 A1 | 12/2009 | Moberg |
| 2009/0299397 A1 | 12/2009 | Ruan |
| 2009/0326459 A1 | 12/2009 | Shipway |
| 2009/0326509 A1 | 12/2009 | Muse |
| 2010/0010455 A1 | 1/2010 | Elahi |
| 2010/0018334 A1 | 1/2010 | Lessing |
| 2010/0019705 A1 | 1/2010 | Kimura |
| 2010/0030156 A1 | 2/2010 | Beebe |
| 2010/0030198 A1 | 2/2010 | Beebe |
| 2010/0037680 A1 | 2/2010 | Moberg |
| 2010/0044270 A1 | 2/2010 | Noble |
| 2010/0049128 A1 | 2/2010 | McKenzie |
| 2010/0049144 A1 | 2/2010 | McConnell |
| 2010/0057057 A1 | 3/2010 | Hayter |
| 2010/0076382 A1 | 3/2010 | Weston |
| 2010/0076412 A1 | 3/2010 | Rush |
| 2010/0081993 A1 | 4/2010 | O'Connor |
| 2010/0094255 A1 | 4/2010 | Nycz |
| 2010/0100076 A1 | 4/2010 | Rush |
| 2010/0100077 A1 | 4/2010 | Rush |
| 2010/0106098 A1 | 4/2010 | Atterbury |
| 2010/0121277 A1 | 5/2010 | Fehr |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat |
| 2010/0145305 A1 | 6/2010 | Alon |
| 2010/0152658 A1 | 6/2010 | Hanson |
| 2010/0160894 A1 | 6/2010 | Julian |
| 2010/0162548 A1 | 7/2010 | Leidig |
| 2010/0168607 A1 | 7/2010 | Miesel |
| 2010/0168683 A1 | 7/2010 | Cabiri |
| 2010/0185148 A1 | 7/2010 | Gillespie, III |
| 2010/0191187 A1 | 7/2010 | Kim |
| 2010/0198157 A1 | 8/2010 | Gyrn |
| 2010/0204657 A1 | 8/2010 | Yodfat |
| 2010/0211011 A1 | 8/2010 | Haar |
| 2010/0212407 A1 | 8/2010 | Stringham |
| 2010/0217192 A1 | 8/2010 | Moberg |
| 2010/0217193 A1 | 8/2010 | Moberg |
| 2010/0234767 A1 | 9/2010 | Sarstedt |
| 2010/0234805 A1 | 9/2010 | Kaufmann |
| 2010/0234830 A1 | 9/2010 | Straessler |
| 2010/0241065 A1 | 9/2010 | Moberg |
| 2010/0241103 A1 | 9/2010 | Kraft |
| 2010/0253140 A1 | 10/2010 | Yamashita |
| 2010/0256486 A1 | 10/2010 | Savage |
| 2010/0262404 A1 | 10/2010 | Bertness |
| 2010/0264931 A1 | 10/2010 | Lindegger |
| 2010/0268169 A1 | 10/2010 | Llewellyn-Hyde |
| 2010/0274112 A1 | 10/2010 | Hoss |
| 2010/0274192 A1 | 10/2010 | Mernoe |

(56) References Cited

U.S. PATENT DOCUMENTS

| | | |
|---|---|---|
| 2010/0274202 A1 | 10/2010 | Hyde |
| 2010/0276411 A1 | 11/2010 | Hansen |
| 2010/0280499 A1 | 11/2010 | Yodfat |
| 2010/0286714 A1 | 11/2010 | Gyrn |
| 2010/0331826 A1 | 12/2010 | Field |
| 2011/0031805 A1 | 2/2011 | Yamashita |
| 2011/0034900 A1 | 2/2011 | Yodfat |
| 2011/0040280 A1 | 2/2011 | Ijitsu |
| 2011/0054399 A1 | 3/2011 | Chong |
| 2011/0054400 A1 | 3/2011 | Chong |
| 2011/0057510 A1 | 3/2011 | Yamashita |
| 2011/0060284 A1 | 3/2011 | Harr |
| 2011/0066131 A1 | 3/2011 | Cabiri |
| 2011/0092915 A1 | 4/2011 | Olson |
| 2011/0092952 A1 | 4/2011 | Voellmicke |
| 2011/0098887 A1 | 4/2011 | Fujimoto |
| 2011/0112504 A1 | 5/2011 | Causey |
| 2011/0119033 A1 | 5/2011 | Moberg |
| 2011/0125056 A1 | 5/2011 | Merchant |
| 2011/0137239 A1 | 6/2011 | Debelser |
| 2011/0137247 A1 | 6/2011 | Mesa |
| 2011/0144584 A1 | 6/2011 | Wozencroft |
| 2011/0152780 A1 | 6/2011 | Olivier |
| 2011/0160654 A1 | 6/2011 | Hanson |
| 2011/0160655 A1 | 6/2011 | Hanson |
| 2011/0160666 A1 | 6/2011 | Hanson |
| 2011/0160669 A1 | 6/2011 | Gyrn |
| 2011/0166509 A1 | 7/2011 | Gross |
| 2011/0172645 A1 | 7/2011 | Moga |
| 2011/0172745 A1 | 7/2011 | Na |
| 2011/0178463 A1 | 7/2011 | Cabiri |
| 2011/0178472 A1 | 7/2011 | Cabiri |
| 2011/0184342 A1 | 7/2011 | Pesach |
| 2011/0201998 A1 | 8/2011 | Pongpairochana |
| 2011/0224614 A1 | 9/2011 | Moberg |
| 2011/0224616 A1 | 9/2011 | Slate |
| 2011/0224646 A1 | 9/2011 | Yodfat |
| 2011/0233393 A1 | 9/2011 | Hanson |
| 2011/0238031 A1 | 9/2011 | Adair |
| 2011/0245773 A1 | 10/2011 | Estes |
| 2011/0264326 A1 | 10/2011 | Iwasaki |
| 2011/0264383 A1 | 10/2011 | Moberg |
| 2011/0270160 A1 | 11/2011 | Mernoe |
| 2011/0272205 A1 | 11/2011 | Fujimoto |
| 2011/0273148 A1 | 11/2011 | Ueno |
| 2011/0282282 A1 | 11/2011 | Lorenzen |
| 2011/0282296 A1 | 11/2011 | Harms |
| 2011/0295205 A1 | 12/2011 | Kaufmann |
| 2011/0313238 A1 | 12/2011 | Reichenbach |
| 2011/0313351 A1 | 12/2011 | Kamen |
| 2011/0319861 A1 | 12/2011 | Wilk |
| 2011/0319919 A1 | 12/2011 | Curry |
| 2012/0004602 A1 | 1/2012 | Hanson |
| 2012/0004639 A1 | 1/2012 | Schoonmaker |
| 2012/0010594 A1 | 1/2012 | Holt |
| 2012/0022344 A1 | 1/2012 | Kube |
| 2012/0022496 A1 | 1/2012 | Causey |
| 2012/0022499 A1 | 1/2012 | Anderson |
| 2012/0025995 A1 | 2/2012 | Moberg |
| 2012/0029431 A1 | 2/2012 | Hwang |
| 2012/0035546 A1 | 2/2012 | Cabiri |
| 2012/0041364 A1 | 2/2012 | Smith |
| 2012/0041370 A1 | 2/2012 | Moberg |
| 2012/0041387 A1 | 2/2012 | Ulrich |
| 2012/0041414 A1 | 2/2012 | Estes |
| 2012/0059332 A1 | 3/2012 | Woehr |
| 2012/0071819 A1 | 3/2012 | Ulrich |
| 2012/0071828 A1 | 3/2012 | Tojo |
| 2012/0078217 A1 | 3/2012 | Smith |
| 2012/0096953 A1 | 4/2012 | Bente, IV |
| 2012/0096954 A1 | 4/2012 | Vazquez |
| 2012/0101436 A1 | 4/2012 | Bazargan |
| 2012/0108933 A1 | 5/2012 | Liang |
| 2012/0109059 A1 | 5/2012 | Ranalletta |
| 2012/0116311 A1 | 5/2012 | Ulrich |
| 2012/0118777 A1 | 5/2012 | Kakiuchi |
| 2012/0123387 A1 | 5/2012 | Gonzalez |
| 2012/0129362 A1 | 5/2012 | Hampo |
| 2012/0132203 A1 | 5/2012 | Hodson |
| 2012/0143136 A1 | 6/2012 | Constantineau |
| 2012/0160033 A1 | 6/2012 | Kow |
| 2012/0165733 A1 | 6/2012 | Bazargan |
| 2012/0165780 A1 | 6/2012 | Bazargan |
| 2012/0172804 A1 | 7/2012 | Plumptre |
| 2012/0172817 A1 | 7/2012 | Ulrich |
| 2012/0184917 A1 | 7/2012 | Bom |
| 2012/0192837 A1 | 8/2012 | Kitamura |
| 2012/0215169 A1 | 8/2012 | Moberg |
| 2012/0215199 A1 | 8/2012 | Moberg |
| 2012/0226234 A1 | 9/2012 | Bazargan |
| 2012/0227729 A1 | 9/2012 | Lundahl |
| 2012/0238961 A1 | 9/2012 | Julian |
| 2012/0259282 A1 | 10/2012 | Alderete, Jr. |
| 2012/0296174 A1 | 11/2012 | McCombie |
| 2012/0310153 A1 | 12/2012 | Moberg |
| 2012/0316506 A1 | 12/2012 | Sonderegger |
| 2013/0002045 A1 | 1/2013 | Hassan-Ali |
| 2013/0012873 A1 | 1/2013 | Gross |
| 2013/0012875 A1 | 1/2013 | Gross |
| 2013/0041346 A1 | 2/2013 | Alon |
| 2013/0060194 A1 | 3/2013 | Rotstein |
| 2013/0060233 A1 | 3/2013 | O'Connor |
| 2013/0068319 A1 | 3/2013 | Plumptre |
| 2013/0085457 A1 | 4/2013 | Schiff |
| 2013/0089992 A1 | 4/2013 | Yang |
| 2013/0096509 A1 | 4/2013 | Avery |
| 2013/0110049 A1 | 5/2013 | Cronenberg |
| 2013/0131589 A1 | 5/2013 | Mudd |
| 2013/0131604 A1 | 5/2013 | Avery |
| 2013/0133438 A1 | 5/2013 | Kow |
| 2013/0148270 A1 | 6/2013 | Fujioka |
| 2013/0172808 A1 | 7/2013 | Gilbert |
| 2013/0175192 A1 | 7/2013 | Iio |
| 2013/0190691 A1 | 7/2013 | Cabiri |
| 2013/0190693 A1 | 7/2013 | Ekman |
| 2013/0200549 A1 | 8/2013 | Felts |
| 2013/0204187 A1 | 8/2013 | Avery |
| 2013/0204191 A1 | 8/2013 | Cindrich |
| 2013/0218089 A1 | 8/2013 | Davies |
| 2013/0218092 A1 | 8/2013 | Davies |
| 2013/0226098 A1 | 8/2013 | Tokumoto |
| 2013/0237953 A1 | 9/2013 | Kow |
| 2013/0245595 A1 | 9/2013 | Kow |
| 2013/0245596 A1 | 9/2013 | Cabiri |
| 2013/0245604 A1 | 9/2013 | Kouyoumjian |
| 2013/0253419 A1 | 9/2013 | Favreau |
| 2013/0253420 A1 | 9/2013 | Favreau |
| 2013/0253421 A1 | 9/2013 | Favreau |
| 2013/0253434 A1 | 9/2013 | Cabiri |
| 2013/0253472 A1 | 9/2013 | Cabiri |
| 2013/0267895 A1 | 10/2013 | Hemmingsen |
| 2013/0296785 A1 | 11/2013 | Cabiri |
| 2013/0296792 A1 | 11/2013 | Cabiri |
| 2013/0296799 A1 | 11/2013 | Degtiar |
| 2013/0296824 A1 | 11/2013 | Mo |
| 2013/0304021 A1 | 11/2013 | Cabiri |
| 2013/0310753 A1 | 11/2013 | Oz |
| 2013/0310807 A1 | 11/2013 | Adair |
| 2013/0323699 A1 | 12/2013 | Edwards |
| 2013/0331791 A1 | 12/2013 | Gross |
| 2013/0338584 A1 | 12/2013 | Mounce |
| 2014/0012229 A1 | 1/2014 | Bokelman |
| 2014/0018735 A1 | 1/2014 | Causey |
| 2014/0031747 A1 | 1/2014 | Ardehali |
| 2014/0052072 A1 | 2/2014 | Simas, Jr. |
| 2014/0055073 A1 | 2/2014 | Favreau |
| 2014/0055076 A1 | 2/2014 | Favreau |
| 2014/0058349 A1 | 2/2014 | Bazargan |
| 2014/0083517 A1 | 3/2014 | Moia |
| 2014/0088509 A1 | 3/2014 | Sonderegger |
| 2014/0094755 A1 | 4/2014 | Bazargan |
| 2014/0121633 A1 | 5/2014 | Causey |
| 2014/0128807 A1 | 5/2014 | Moberg |
| 2014/0128815 A1 | 5/2014 | Cabiri |

(56) References Cited

U.S. PATENT DOCUMENTS

| | | |
|---|---|---|
| 2014/0128835 A1 | 5/2014 | Moberg |
| 2014/0135692 A1 | 5/2014 | Alderete, Jr. |
| 2014/0135694 A1 | 5/2014 | Moberg |
| 2014/0142499 A1 | 5/2014 | Moberg |
| 2014/0148784 A1 | 5/2014 | Anderson |
| 2014/0148785 A1 | 5/2014 | Moberg |
| 2014/0163522 A1 | 6/2014 | Alderete, Jr. |
| 2014/0163526 A1 | 6/2014 | Cabiri |
| 2014/0171881 A1 | 6/2014 | Cabiri |
| 2014/0174223 A1 | 6/2014 | Gross |
| 2014/0188073 A1 | 7/2014 | Cabiri |
| 2014/0194819 A1 | 7/2014 | Maule |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0207080 A1 | 7/2014 | Allerdings |
| 2014/0207104 A1 | 7/2014 | Vouillamoz |
| 2014/0210631 A1 | 7/2014 | Zavis |
| 2014/0213975 A1 | 7/2014 | Clemente |
| 2014/0214001 A1 | 7/2014 | Mortazavi |
| 2014/0228768 A1 | 8/2014 | Eggert |
| 2014/0228780 A1 | 8/2014 | Cabiri |
| 2014/0236087 A1 | 8/2014 | Alderete, Jr. |
| 2014/0243786 A1 | 8/2014 | Gilbert |
| 2014/0249502 A1 | 9/2014 | Nie |
| 2014/0261758 A1 | 9/2014 | Wlodarczyk |
| 2014/0288511 A1 | 9/2014 | Tan-Malecki |
| 2014/0322935 A1 | 10/2014 | Filman |
| 2014/0330240 A1 | 11/2014 | Cabiri |
| 2014/0343406 A1 | 11/2014 | Damjanovic |
| 2014/0343503 A1 | 11/2014 | Holmqvist |
| 2014/0364808 A1 | 12/2014 | Niklaus |
| 2015/0005703 A1 | 1/2015 | Hutchinson |
| 2015/0011965 A1 | 1/2015 | Cabiri |
| 2015/0011976 A1 | 1/2015 | Vouillamoz |
| 2015/0032084 A1 | 1/2015 | Cabiri |
| 2015/0045729 A1 | 2/2015 | Denzer |
| 2015/0057613 A1 | 2/2015 | Clemente |
| 2015/0057615 A1 | 2/2015 | Mernoe, V |
| 2015/0073344 A1 | 3/2015 | Van Damme |
| 2015/0088071 A1 | 3/2015 | Cabiri |
| 2015/0112278 A1 | 4/2015 | Ray |
| 2015/0119797 A1 | 4/2015 | Cabiri |
| 2015/0119798 A1 | 4/2015 | Gross |
| 2015/0157806 A1 | 6/2015 | Knutsson |
| 2015/0165121 A1 | 6/2015 | Murakami |
| 2015/0174346 A1 | 6/2015 | Dhuppad |
| 2015/0180146 A1 | 6/2015 | Filman |
| 2015/0182691 A1 | 7/2015 | Mcloughlin |
| 2015/0202375 A1 | 7/2015 | Schabbach |
| 2015/0224253 A1 | 8/2015 | Cabiri |
| 2015/0224258 A1 | 8/2015 | Holtwick |
| 2015/0250946 A1 | 9/2015 | Cabiri |
| 2015/0297833 A1 | 10/2015 | Henderson |
| 2015/0320990 A1 | 11/2015 | Burton |
| 2015/0367074 A1 | 12/2015 | Draper |
| 2015/0367075 A1* | 12/2015 | Cave .............. A61M 5/34 604/240 |
| 2015/0374926 A1 | 12/2015 | Gross |
| 2016/0015910 A1* | 1/2016 | Mukai ............. A61M 5/5086 604/111 |
| 2016/0030665 A1 | 2/2016 | Cabiri |
| 2016/0038691 A1 | 2/2016 | Mounce |
| 2016/0051756 A1 | 2/2016 | Cabiri |
| 2016/0051765 A1 | 2/2016 | Morris |
| 2016/0051767 A1 | 2/2016 | Higgins |
| 2016/0058941 A1 | 3/2016 | Wu |
| 2016/0082182 A1* | 3/2016 | Gregory ........... A61M 5/14248 604/152 |
| 2016/0136353 A1 | 5/2016 | Adams |
| 2016/0144117 A1 | 5/2016 | Chun |
| 2016/0151586 A1 | 6/2016 | Kemp |
| 2016/0158435 A1 | 6/2016 | Wu |
| 2016/0158436 A1 | 6/2016 | Yang |
| 2016/0175515 A1 | 6/2016 | McCullough |
| 2016/0184512 A1 | 6/2016 | Marbet |
| 2016/0184519 A1* | 6/2016 | Blundred .......... A61M 5/16827 604/89 |
| 2016/0186906 A1 | 6/2016 | Blake |
| 2016/0193406 A1 | 7/2016 | Cabiri |
| 2016/0199590 A1 | 7/2016 | Schabbach |
| 2016/0199592 A1 | 7/2016 | Eggert |
| 2016/0213840 A1 | 7/2016 | Schabbach |
| 2016/0220755 A1 | 8/2016 | Lanigan |
| 2016/0228644 A1 | 8/2016 | Cabiri |
| 2016/0228652 A1 | 8/2016 | Cabiri |
| 2016/0256352 A1 | 9/2016 | Bar-El |
| 2016/0296699 A1 | 10/2016 | Cabiri |
| 2016/0296713 A1 | 10/2016 | Schader |
| 2016/0296716 A1 | 10/2016 | Cabiri |
| 2016/0303324 A1 | 10/2016 | Cabiri |
| 2016/0317736 A1 | 11/2016 | Schabbach |
| 2016/0317737 A1 | 11/2016 | Schabbach |
| 2016/0331900 A1 | 11/2016 | Wei |
| 2016/0339168 A1 | 11/2016 | Hutchinson |
| 2016/0346478 A1 | 12/2016 | Bar-El |
| 2016/0354553 A1 | 12/2016 | Anderson |
| 2017/0007774 A1 | 1/2017 | Brockmeier |
| 2017/0028132 A1 | 2/2017 | Cronenberg |
| 2017/0043092 A1* | 2/2017 | Murakami ........ A61M 5/20 |
| 2017/0058349 A1 | 3/2017 | Levy |
| 2017/0080158 A1 | 3/2017 | Cabiri |
| 2017/0106138 A1 | 4/2017 | Cabiri |
| 2017/0175859 A1 | 6/2017 | Brockmeier |
| 2017/0224915 A1 | 8/2017 | Destefano |
| 2017/0246399 A1 | 8/2017 | Forlani |
| 2017/0246403 A1 | 8/2017 | Cowe |
| 2017/0281859 A1 | 10/2017 | Agard |
| 2017/0312450 A1 | 11/2017 | Gross |
| 2017/0354781 A1 | 12/2017 | Cronenberg |
| 2017/0354782 A1 | 12/2017 | Quinn |
| 2017/0354783 A1 | 12/2017 | Gazeley |
| 2017/0354785 A1 | 12/2017 | Gazeley |
| 2017/0354788 A1 | 12/2017 | Quinn |
| 2018/0001073 A1 | 1/2018 | Clemente |
| 2018/0008769 A1 | 1/2018 | O'Connor |
| 2018/0021508 A1 | 1/2018 | Destefano |
| 2018/0028747 A1 | 2/2018 | Hanson |
| 2018/0028765 A1 | 2/2018 | Waller |
| 2018/0043091 A1 | 2/2018 | Agard |
| 2018/0055995 A1 | 3/2018 | Hanson |
| 2018/0133413 A1 | 5/2018 | Grant |
| 2018/0214637 A1 | 8/2018 | Kemp |
| 2018/0221584 A1 | 8/2018 | Grimoldby |
| 2018/0236173 A1 | 8/2018 | McCaffrey |
| 2018/0304029 A1 | 10/2018 | Koch |
| 2018/0339168 A1* | 11/2018 | Helmer ............. A61M 5/3287 |
| 2019/0015582 A1 | 1/2019 | Naftalovitz |
| 2019/0022306 A1 | 1/2019 | Gibson |
| 2019/0060578 A1 | 2/2019 | Farris |
| 2019/0071217 A1 | 3/2019 | Brown |
| 2019/0091404 A1 | 3/2019 | Nazzaro |
| 2019/0099549 A1 | 4/2019 | Lanigan |
| 2019/0117880 A1 | 4/2019 | Hirschel |
| 2019/0175821 A1 | 6/2019 | Kamen |
| 2019/0224415 A1 | 7/2019 | Dugand |
| 2019/0240417 A1 | 8/2019 | Hostettler |
| 2019/0328968 A1 | 10/2019 | Giambattista |
| 2019/0366012 A1 | 12/2019 | Gross |
| 2020/0009323 A1 | 1/2020 | Nair |
| 2020/0164151 A1 | 5/2020 | Farris |
| 2020/0215270 A1 | 7/2020 | Ogawa |
| 2020/0282144 A1 | 9/2020 | Pearson |
| 2020/0297929 A1 | 9/2020 | Zhang |
| 2020/0360602 A1 | 11/2020 | Gray |
| 2021/0138157 A1 | 5/2021 | Bar-El |
| 2021/0220551 A1 | 7/2021 | Dowd |

FOREIGN PATENT DOCUMENTS

| | | |
|---|---|---|
| CA | 2990453 A1 | 1/2017 |
| CN | 2107925 | 6/1992 |
| CN | 1224341 A | 7/1999 |

(56) References Cited

FOREIGN PATENT DOCUMENTS

| | | |
|---|---|---|
| CN | 1355716 | 6/2002 |
| CN | 1408443 A | 4/2003 |
| CN | 1505535 A | 6/2004 |
| CN | 1543363 | 11/2004 |
| CN | 1636605 A | 7/2005 |
| CN | 1658919 | 8/2005 |
| CN | 1671432 | 9/2005 |
| CN | 2748099 | 12/2005 |
| CN | 1747683 A | 3/2006 |
| CN | 1756573 A | 4/2006 |
| CN | 1863566 A | 11/2006 |
| CN | 1917912 | 2/2007 |
| CN | 1921900 | 2/2007 |
| CN | 1929884 A | 3/2007 |
| CN | 101001661 A | 7/2007 |
| CN | 101090749 A | 12/2007 |
| CN | 101163513 | 4/2008 |
| CN | 101227943 A | 7/2008 |
| CN | 101239205 A | 8/2008 |
| CN | 101267853 | 9/2008 |
| CN | 201233444 | 5/2009 |
| CN | 101448536 A | 6/2009 |
| CN | 101460207 A | 6/2009 |
| CN | 101478999 | 7/2009 |
| CN | 101522235 A | 9/2009 |
| CN | 101541362 A | 9/2009 |
| CN | 101557847 | 10/2009 |
| CN | 101573155 | 11/2009 |
| CN | 101641126 A | 2/2010 |
| CN | 101687083 A | 3/2010 |
| CN | 101703816 | 5/2010 |
| CN | 101868269 | 10/2010 |
| CN | 101868273 A | 10/2010 |
| CN | 201692438 U | 1/2011 |
| CN | 101970033 A | 2/2011 |
| CN | 102022308 A | 4/2011 |
| CN | 102038998 | 5/2011 |
| CN | 102083483 | 6/2011 |
| CN | 102083487 | 6/2011 |
| CN | 102089024 | 6/2011 |
| CN | 201941304 U | 8/2011 |
| CN | 102186733 A | 9/2011 |
| CN | 102245228 | 11/2011 |
| CN | 102245235 | 11/2011 |
| CN | 102256657 A | 11/2011 |
| CN | 202086877 | 12/2011 |
| CN | 102307606 | 1/2012 |
| CN | 102370487 | 3/2012 |
| CN | 102378638 A | 3/2012 |
| CN | 102480215 | 5/2012 |
| CN | 102573616 | 7/2012 |
| CN | 102639169 A | 8/2012 |
| CN | 102639174 | 8/2012 |
| CN | 102665805 A | 9/2012 |
| CN | 102733161 | 10/2012 |
| CN | 102883759 | 1/2013 |
| CN | 102917739 | 2/2013 |
| CN | 102958550 | 3/2013 |
| CN | 102971027 | 3/2013 |
| CN | 103079616 A | 5/2013 |
| CN | 103118737 | 5/2013 |
| CN | 103269736 | 8/2013 |
| CN | 103520792 | 1/2014 |
| CN | 104127938 | 11/2014 |
| CN | 104132038 A | 11/2014 |
| CN | 104219998 | 12/2014 |
| CN | 104245018 | 12/2014 |
| CN | 104321092 | 1/2015 |
| CN | 104321093 | 1/2015 |
| CN | 104321100 | 1/2015 |
| CN | 104334216 | 2/2015 |
| CN | 104379196 | 2/2015 |
| CN | 104394912 | 3/2015 |
| CN | 104703641 A | 6/2015 |
| CN | 104759006 | 7/2015 |
| CN | 104812428 | 7/2015 |
| CN | 104853787 | 8/2015 |
| CN | 104955504 A | 9/2015 |
| CN | 105025958 | 11/2015 |
| CN | 105102025 A | 11/2015 |
| CN | 105107065 | 12/2015 |
| CN | 105307709 | 2/2016 |
| CN | 105324140 | 2/2016 |
| CN | 105816942 | 8/2016 |
| CN | 205434562 | 8/2016 |
| CN | 105979990 | 9/2016 |
| CN | 106178185 | 12/2016 |
| CN | 106714878 | 5/2017 |
| DE | 855313 C | 11/1952 |
| DE | 1064693 B | 9/1959 |
| DE | 19518807 A1 | 12/1995 |
| DE | 19717107 A1 | 11/1998 |
| EP | 0017412 A1 | 10/1980 |
| EP | 0222656 A1 | 5/1987 |
| EP | 0401179 A1 | 12/1990 |
| EP | 0526986 A1 | 2/1993 |
| EP | 0744975 A1 | 12/1996 |
| EP | 0851774 A1 | 7/1998 |
| EP | 0925082 A1 | 6/1999 |
| EP | 1003581 A1 | 5/2000 |
| EP | 1003581 B1 | 11/2000 |
| EP | 1124600 A1 | 8/2001 |
| EP | 1156843 | 11/2001 |
| EP | 1219312 A2 | 7/2002 |
| EP | 1249250 A1 | 10/2002 |
| EP | 1472477 A1 | 11/2004 |
| EP | 1530979 A1 | 5/2005 |
| EP | 1666080 A1 | 6/2006 |
| EP | 1372762 B1 | 2/2007 |
| EP | 1930038 A2 | 6/2008 |
| EP | 1974759 A1 | 10/2008 |
| EP | 2060606 A1 | 5/2009 |
| EP | 2140897 A1 | 1/2010 |
| EP | 2173413 A1 | 4/2010 |
| EP | 2185227 A2 | 5/2010 |
| EP | 2192935 A1 | 6/2010 |
| EP | 1624913 B1 | 7/2010 |
| EP | 2316510 A2 | 5/2011 |
| EP | 2345441 A1 | 7/2011 |
| EP | 2361648 A1 | 8/2011 |
| EP | 2364739 A1 | 9/2011 |
| EP | 2364741 A1 | 9/2011 |
| EP | 2393534 A1 | 12/2011 |
| EP | 2412395 A1 | 2/2012 |
| EP | 2452708 A1 | 5/2012 |
| EP | 2468340 A1 | 6/2012 |
| EP | 2468342 A1 | 6/2012 |
| EP | 2498589 A1 | 9/2012 |
| EP | 2574355 A1 | 4/2013 |
| EP | 2578188 A1 | 4/2013 |
| EP | 2650031 A1 | 10/2013 |
| EP | 2698180 A1 | 2/2014 |
| EP | 2712650 A1 | 4/2014 |
| EP | 2714155 A2 | 4/2014 |
| EP | 2727617 A1 | 5/2014 |
| EP | 2799740 A2 | 11/2014 |
| EP | 2393535 B1 | 3/2015 |
| EP | 2862588 A1 | 4/2015 |
| EP | 2878321 A1 | 6/2015 |
| EP | 2886144 A1 | 6/2015 |
| EP | 2454483 B1 | 8/2015 |
| EP | 2932993 A1 | 10/2015 |
| EP | 1904130 B1 | 3/2016 |
| EP | 2991705 A1 | 3/2016 |
| EP | 3124066 | 2/2017 |
| EP | 3125066 | 2/2017 |
| EP | 3266478 A1 | 1/2018 |
| EP | 2819724 B1 | 3/2019 |
| EP | 3266478 B1 | 1/2020 |
| FR | 2770136 A1 | 4/1999 |
| FR | 2905273 A1 | 3/2008 |
| GB | 2436526 A | 10/2007 |
| JP | S55146165 | 11/1980 |
| JP | S62112566 A | 5/1987 |

(56) References Cited

FOREIGN PATENT DOCUMENTS

| | | |
|---|---|---|
| JP | S63287364 | 11/1988 |
| JP | H01172843 U | 12/1989 |
| JP | H05062828 A | 3/1993 |
| JP | H07194701 A | 8/1995 |
| JP | 3035448 U | 3/1997 |
| JP | H09505758 A | 6/1997 |
| JP | H10167593 | 6/1998 |
| JP | H11507260 A | 6/1999 |
| JP | 2000107289 A | 4/2000 |
| JP | 2000515394 A | 11/2000 |
| JP | 2001512992 A | 8/2001 |
| JP | 2002505601 A | 2/2002 |
| JP | 2002507459 A | 3/2002 |
| JP | 2002528234 | 9/2002 |
| JP | 2002528676 A | 9/2002 |
| JP | 2003501157 A | 1/2003 |
| JP | 2003527138 A | 9/2003 |
| JP | 2003534061 A | 11/2003 |
| JP | 2004501721 A | 1/2004 |
| JP | 2004512100 A | 4/2004 |
| JP | 2005523127 A | 8/2005 |
| JP | 2005527249 A | 9/2005 |
| JP | 2005270629 A | 10/2005 |
| JP | 2006501043 | 1/2006 |
| JP | 2006507067 A | 3/2006 |
| JP | 2006510450 A | 3/2006 |
| JP | 2006525046 A | 11/2006 |
| JP | 2007509661 A | 4/2007 |
| JP | 2007306990 A | 11/2007 |
| JP | 2008100762 A | 5/2008 |
| JP | 2008534131 A | 8/2008 |
| JP | 2008220961 A | 9/2008 |
| JP | 2009020101 | 1/2009 |
| JP | 2009502273 A | 1/2009 |
| JP | 2009101093 A | 5/2009 |
| JP | 4305704 B2 | 7/2009 |
| JP | 2010501281 A | 1/2010 |
| JP | 2010540054 A | 12/2010 |
| JP | 2010540156 A | 12/2010 |
| JP | 2011136153 A | 7/2011 |
| JP | 2012010954 | 1/2012 |
| JP | 2012100927 A | 5/2012 |
| JP | 4947871 B2 | 6/2012 |
| JP | 2012516738 | 7/2012 |
| JP | 2013500811 A | 1/2013 |
| JP | 2013504405 | 2/2013 |
| JP | 2013505433 A | 2/2013 |
| JP | 2013517094 | 5/2013 |
| JP | 2013517095 A | 5/2013 |
| JP | 2013519473 A | 5/2013 |
| JP | 2013521084 A | 6/2013 |
| JP | 2013523292 | 6/2013 |
| JP | 2013524905 | 6/2013 |
| JP | 2013524906 | 6/2013 |
| JP | 2013524907 | 6/2013 |
| JP | 2013530778 A | 8/2013 |
| JP | 2013531520 A | 8/2013 |
| JP | 2013531540 A | 8/2013 |
| JP | 2014010954 | 1/2014 |
| JP | 2014030489 A | 2/2014 |
| JP | 2014515669 A | 7/2014 |
| JP | 2014518743 A | 8/2014 |
| JP | 2014521443 A | 8/2014 |
| JP | 2014525339 A | 9/2014 |
| JP | 5616906 B2 | 10/2014 |
| JP | 2015514486 A | 5/2015 |
| JP | 2015144850 | 8/2015 |
| JP | 2015524722 A | 8/2015 |
| JP | 2015166048 | 9/2015 |
| JP | 2015536162 A | 12/2015 |
| JP | 2015536715 A | 12/2015 |
| JP | 2016525428 A | 8/2016 |
| JP | 2016530016 A | 9/2016 |
| JP | 2017200617 | 11/2017 |
| KR | 20140000766 U | 2/2014 |
| WO | 8911302 A1 | 11/1989 |
| WO | 9009202 A1 | 8/1990 |
| WO | 9307922 A1 | 4/1993 |
| WO | 9321974 | 11/1993 |
| WO | 9407553 A1 | 4/1994 |
| WO | 9415660 A1 | 7/1994 |
| WO | 1994015660 A1 | 7/1994 |
| WO | 9513838 A1 | 5/1995 |
| WO | 9521645 A1 | 8/1995 |
| WO | 9609083 A1 | 3/1996 |
| WO | 9632975 A1 | 10/1996 |
| WO | 9700091 A1 | 1/1997 |
| WO | 9710012 A1 | 3/1997 |
| WO | 9721457 A1 | 6/1997 |
| WO | 9733638 A1 | 9/1997 |
| WO | 9857683 A1 | 12/1998 |
| WO | 9857686 A1 | 12/1998 |
| WO | 9929151 A1 | 6/1999 |
| WO | 9959665 A1 | 11/1999 |
| WO | 0025844 A1 | 5/2000 |
| WO | 0069509 A1 | 11/2000 |
| WO | 0130415 A2 | 5/2001 |
| WO | 0130421 A2 | 5/2001 |
| WO | 0170304 A1 | 9/2001 |
| WO | 0172357 A2 | 10/2001 |
| WO | 0187384 A1 | 11/2001 |
| WO | 0189607 A2 | 11/2001 |
| WO | 0189613 A1 | 11/2001 |
| WO | 0202165 A2 | 1/2002 |
| WO | 0204049 A1 | 1/2002 |
| WO | 0234315 A1 | 5/2002 |
| WO | 0238204 A2 | 5/2002 |
| WO | 02056934 A2 | 7/2002 |
| WO | 02056943 A2 | 7/2002 |
| WO | 02072182 A1 | 9/2002 |
| WO | 03026726 | 4/2003 |
| WO | 03062672 A1 | 7/2003 |
| WO | 03090833 A1 | 11/2003 |
| WO | 03103750 A2 | 12/2003 |
| WO | 2004000397 A1 | 12/2003 |
| WO | 2004032989 A2 | 4/2004 |
| WO | 2004032990 A2 | 4/2004 |
| WO | 2004069302 A2 | 8/2004 |
| WO | 2004098684 A2 | 11/2004 |
| WO | 2004105841 A1 | 12/2004 |
| WO | 2005018703 A2 | 3/2005 |
| WO | 2005028358 | 3/2005 |
| WO | 2005037350 A2 | 4/2005 |
| WO | 2005070485 A1 | 8/2005 |
| WO | 2005072795 A2 | 8/2005 |
| WO | 2005077441 A2 | 8/2005 |
| WO | 2006016364 A2 | 2/2006 |
| WO | 2006018617 A1 | 2/2006 |
| WO | 2006037434 A1 | 4/2006 |
| WO | 2006052737 A1 | 5/2006 |
| WO | 2006069380 A1 | 6/2006 |
| WO | 2006102676 A2 | 9/2006 |
| WO | 2006104806 A2 | 10/2006 |
| WO | 2006121921 A2 | 11/2006 |
| WO | 2006127905 | 11/2006 |
| WO | 2007017052 A1 | 2/2007 |
| WO | 2007051563 A1 | 5/2007 |
| WO | 2007056504 A1 | 5/2007 |
| WO | 2007066152 A2 | 6/2007 |
| WO | 2007073228 A1 | 6/2007 |
| WO | 2007092618 A2 | 8/2007 |
| WO | 2007119178 A2 | 10/2007 |
| WO | 2007130868 A1 | 11/2007 |
| WO | 2008001377 A2 | 1/2008 |
| WO | 2008014908 A1 | 2/2008 |
| WO | 2008024781 | 2/2008 |
| WO | 2008024810 A2 | 2/2008 |
| WO | 2008024814 A2 | 2/2008 |
| WO | 2008034743 A1 | 3/2008 |
| WO | 2008057976 A2 | 5/2008 |
| WO | 2008072229 A2 | 6/2008 |
| WO | 2008076459 A1 | 6/2008 |
| WO | 2008078318 A2 | 7/2008 |
| WO | 2008129549 A1 | 10/2008 |

(56) References Cited

FOREIGN PATENT DOCUMENTS

| | | |
|---|---|---|
| WO | 2008131684 | 11/2008 |
| WO | 2009019438 A1 | 2/2009 |
| WO | 2009022132 A2 | 2/2009 |
| WO | 2009043000 A1 | 4/2009 |
| WO | 2009043564 A1 | 4/2009 |
| WO | 2009044401 A2 | 4/2009 |
| WO | 2009046989 A2 | 4/2009 |
| WO | 2009069064 A1 | 6/2009 |
| WO | 2009081262 A1 | 7/2009 |
| WO | 2009125398 A2 | 10/2009 |
| WO | 2009144085 A2 | 12/2009 |
| WO | 2010078227 A1 | 7/2010 |
| WO | 2010078242 A1 | 7/2010 |
| WO | 2010089313 A1 | 8/2010 |
| WO | 2010117841 | 10/2010 |
| WO | 2011034799 A1 | 3/2011 |
| WO | 2011075105 A1 | 6/2011 |
| WO | 2011090955 A1 | 7/2011 |
| WO | 2011090956 A2 | 7/2011 |
| WO | 2011091265 | 7/2011 |
| WO | 2011097487 | 8/2011 |
| WO | 2011101378 A1 | 8/2011 |
| WO | 2011104711 A1 | 9/2011 |
| WO | 2011110872 A1 | 9/2011 |
| WO | 2011113806 A1 | 9/2011 |
| WO | 2011124631 A1 | 10/2011 |
| WO | 2011129175 A1 | 10/2011 |
| WO | 2011131778 A1 | 10/2011 |
| WO | 2011131780 A2 | 10/2011 |
| WO | 2011131781 A1 | 10/2011 |
| WO | 2011133823 A1 | 10/2011 |
| WO | 2011141907 A1 | 11/2011 |
| WO | 2011156373 A1 | 12/2011 |
| WO | 2012000836 A1 | 1/2012 |
| WO | 2012003221 A1 | 1/2012 |
| WO | 2012032411 A2 | 3/2012 |
| WO | 2012040528 A1 | 3/2012 |
| WO | 2012064258 A1 | 5/2012 |
| WO | 2012108955 | 8/2012 |
| WO | 2012134588 A1 | 10/2012 |
| WO | 2012145685 A1 | 10/2012 |
| WO | 2012145752 A2 | 10/2012 |
| WO | 2012160157 A1 | 11/2012 |
| WO | 2012160160 A1 | 11/2012 |
| WO | 2012160164 | 11/2012 |
| WO | 2012164397 A1 | 12/2012 |
| WO | 2012168691 A1 | 12/2012 |
| WO | 2013036602 A1 | 3/2013 |
| WO | 2013058697 A1 | 4/2013 |
| WO | 2013115843 A1 | 8/2013 |
| WO | 2013148270 A2 | 10/2013 |
| WO | 2013148435 A1 | 10/2013 |
| WO | 2013173092 A1 | 11/2013 |
| WO | 2014039574 | 3/2014 |
| WO | 2014052676 A1 | 4/2014 |
| WO | 2014060563 A2 | 4/2014 |
| WO | 2014070453 A1 | 5/2014 |
| WO | 2014081411 A1 | 5/2014 |
| WO | 2014107408 A1 | 7/2014 |
| WO | 2014132293 A1 | 9/2014 |
| WO | 2014144096 | 9/2014 |
| WO | 2014159017 A1 | 10/2014 |
| WO | 2014179117 A1 | 11/2014 |
| WO | 2014179210 A1 | 11/2014 |
| WO | 2014179774 A1 | 11/2014 |
| WO | 2014194183 A2 | 12/2014 |
| WO | 2015018787 A1 | 2/2015 |
| WO | 2015048791 A1 | 4/2015 |
| WO | 2015048803 A2 | 4/2015 |
| WO | 2015078868 A1 | 6/2015 |
| WO | 2015091758 A1 | 6/2015 |
| WO | 2015091850 A1 | 6/2015 |
| WO | 2015114158 A1 | 8/2015 |
| WO | 2015114428 A1 | 8/2015 |
| WO | 2015118358 A1 | 8/2015 |
| WO | 2015146276 | 10/2015 |
| WO | 2015163009 A1 | 10/2015 |
| WO | 2015187797 | 12/2015 |
| WO | 2016060986 | 4/2016 |
| WO | 2016087626 A1 | 6/2016 |
| WO | 2016087627 A1 | 6/2016 |
| WO | 2016141082 A1 | 9/2016 |
| WO | 2016196934 | 12/2016 |
| WO | 2017022639 A1 | 2/2017 |
| WO | 2017033193 | 3/2017 |
| WO | 2017041996 A1 | 3/2017 |
| WO | 2017064483 | 4/2017 |
| WO | 2017161076 A1 | 9/2017 |
| WO | 2017210448 | 12/2017 |
| WO | 2018060023 | 4/2018 |
| WO | 2018222521 A1 | 12/2018 |
| WO | 2019224782 A1 | 11/2019 |
| WO | 2020120087 A1 | 6/2020 |
| WO | 2020193468 A1 | 10/2020 |

OTHER PUBLICATIONS

Office Action dated Apr. 20, 2017 in U.S. Appl. No. 13/886,867, by Cabiri.

Office Action dated Apr. 22, 2016 in CN Application No. 2014102892041.

Office Action dated Apr. 23, 2015 in JP Application No. 2012-550069. 6 pages.

Office Action dated Apr. 24, 2013 in CN Application No. 201080040968. 7. 8 pages.

Office Action dated Apr. 5, 2010 in U.S. Appl. No. 12/244,666. 11 pages.

Office Action dated Apr. 5, 2010 in U.S. Appl. No. 12/244,688. 14 pages.

Office Action dated Apr. 7, 2020 in Chinese Application No. 201880036318.1.

Office Action dated Aug. 10, 2017 in U.S. Appl. No. 14/372,384, by Cabiri.

Office Action dated Aug. 13, 2015 in U.S. Appl. No. 14/553,399 by Cabiri. 6 pages.

Office Action dated Aug. 13, 2018 in IN Application No. 857/KOLNP/2012. 4 pages.

Office Action dated Aug. 14, 2017 in CN Application No. 201410178318.9.

Office Action dated Aug. 15, 2013 in CN Application No. 200880117084.X. 8 pages.

Office Action dated Aug. 15, 2013 in U.S. Appl. No. 13/429,942 by Cabiri. 12 pages.

Office Action dated Aug. 26, 2014 in CN Application No. 201180006567.4. 10 pages.

Office Action dated Aug. 29, 2014 in JP Application No. 2012-550068. 8 pages.

Office Action dated Aug. 29, 2014 in JP Application No. 2012-550069. 6 pages.

Office Action dated Aug. 6, 2014 in EP Application No. 11 707 942.6. 4 pages.

Office Action dated Dec. 1, 2015 in CN Application No. 201410289204. 1.

Office Action dated Dec. 10, 2013 in CN Application No. 201180006567.4. 8 pages.

Office Action dated Dec. 12, 2013 in JP Application No. 2012-529808. 11 pages.

Office Action dated Dec. 15, 2017 in U.S. Appl. No. 15/269,248, by Cabiri.

Office Action dated Dec. 15, 2020 in Japanese Application No. 2019-566222.

Office Action dated Dec. 29, 2016 in CN Application No. 201510695320.8. 12 pages.

Office Action dated Dec. 3, 2015 in CN Application No. 201280068544. 0. 16 pages.

Office Action dated Dec. 4, 2017 in CN Application No. 201410178374. 2.

Office Action dated Dec. 9, 2016 in U.S. Appl. No. 14/593,051, by Gross.

(56) References Cited

OTHER PUBLICATIONS

Office Action dated Feb. 15, 2017 in CN Application No. 201380027455.6.
Office Action dated Feb. 16, 2017 in CN Application No. 2014101783189.
Office Action dated Feb. 19, 2018 in EP Application No. 14789668.2.
Office Action dated Feb. 20, 2015 in U.S. Appl. No. 13/521,181 by Cabiri. 13 pages.
Office Action dated Feb. 21, 2012 in U.S. Appl. No. 12/689,249. 6 pages.
Office Action dated Feb. 24, 2015 in U.S. Appl. No. 14/258,661 by Cabiri. 7 pages.
Office Action dated Feb. 24, 2016 in U.S. Appl. No. 13/429,942 by Cabiri. 8 pages.
Office Action dated Feb. 24, 2017 in U.S. Appl. No. 13/964,651, by Gross.
Office Action dated Feb. 28, 2014 in CN Application No. 201180006571.0.
Office Action dated Feb. 4, 2014 in EP Application No. 11 707 942.6. 6 pages.
Office Action dated Jan. 10, 2017 in U.S. Appl. No. 14/193,692, by Gross.
Office Action dated Jan. 12, 2018 in EP Application No. 14789667.4.
Office Action dated Jan. 15, 2016 in U.S. Appl. No. 13/472,112 by Cabiri. 8 pages.
Office Action dated Jan. 16, 2014 in U.S. Appl. No. 13/429,942 by Cabiri. 10 pages.
Office Action dated Jan. 17, 2017 in EP Application No. 13716886.0.
Office Action dated Jan. 28, 2015 in U.S. Appl. No. 13/429,942 by Cabiri. 9 pages.
Office Action dated Jan. 30, 2013 in CN Application No. 200880117084.X. 8 pages.
Office Action dated Jan. 31, 2018 in U.S. Appl. No. 15/235,931, by Cabiri.
Office Action dated Jan. 4, 2016 in U.S. Appl. No. 13/892,905 by Cabiri. 17 pages.
Office Action dated Jan. 4, 2016 in U.S. Appl. No. 14/096,977 by Cabiri.
Office Action dated Jan. 5, 2016 in U.S. Appl. No. 14/696,644 by Cabiri. 13 pages.
Office Action dated Jan. 8, 2014 in U.S. Appl. No. 13/521,167 by Cabiri. 7 pages.
Office Action dated Jul. 13, 2011 in U.S. Appl. No. 12/559,563. 9 pages.
Office Action dated Jul. 2, 2012 in U.S. Appl. No. 13/272,555. 13 pages. 13 pages.
Office Action dated Nov. 13, 2017 in U.S. Appl. No. 14/193,692, by Gross.
Office Action dated Nov. 14, 2017 in U.S. Appl. No. 14/593,041, by Cabiri.
Office Action dated Nov. 16, 2015 in U.S. Appl. No. 13/733,516 by Cabiri. 9 pages.
Office Action dated Nov. 16, 2017 in CN Application No. 201480054191.8.
Office Action dated Nov. 17, 2017 in U.S. Appl. No. 14/510,846, by Cabiri.
Office Action dated Nov. 2, 2014 in CN Application No. 201180006571.0. 8 pages.
Office Action dated Nov. 2, 2016 in CN Application No. 2013800571961. 16 pages.
Office Action dated Nov. 21, 2014 in U.S. Appl. No. 13/429,840 by Cabiri. 10 pages.
Office Action dated Nov. 21, 2014 in U.S. Appl. No. 13/472,112 by Cabiri. 10 pages.
Office Action dated Nov. 25, 2015 in U.S. Appl. No. 14/372,384 by Cabiri. 24 pages.
Office Action dated Nov. 25, 2016 in U.S. Appl. No. 13/874,017, by Cabiri.
Office Action dated Nov. 29, 2019 in CN Application No. 201680032632.3.
Office Action dated Nov. 4, 2013 in EP Application No. 11 709 234.6. 4 pages.
Office Action dated Nov. 5, 2013 in JP Application No. 2010-527595. 6 pages.
Office Action dated Nov. 5, 2014 in U.S. Appl. No. 13/643,470 by Alon. 15 pages.
Office Action dated Nov. 6, 2015 in U.S. Appl. No. 14/715,791 by Cabiri. 8 pages.
Office Action dated Nov. 8, 2017 in U.S. Appl. No. 13/874, 121, by Degtiar.
Office Action dated Nov. 9, 2016 in U.S. Appl. No. 14/683,253, by Cabiri.
Office Action dated Oct. 11, 2017 in U.S. Appl. No. 29/605,061, by Cabiri. 9 pages.
Office Action dated Oct. 17, 2012 in U.S. Appl. No. 13/063,236.
Office Action dated Oct. 28, 2011 in U.S. Appl. No. 12/615,828. 10 pages.
Office Action dated Oct. 28, 2015 in U.S. Appl. No. 13/429,942 by Cabiri. 8 pages.
Office Action dated Oct. 28, 2016 in CN Application No. 201410178374.2.
Office Action dated Oct. 5, 2017 in U.S. Appl. No. 29/605,068, by Cabiri. 9 pages.
Office Action dated Oct. 6, 2017 in U.S. Appl. No. 14/861,478, by Cabiri.
Office Action dated Oct. 6, 2017 in U.S. Appl. No. 29/604,616, by Cabiri. 11 pages.
Office Action dated Oct. 6, 2017 in U.S. Appl. No. 29/605,051, by Cabiri. 11 pages.
Office Action dated Oct. 7, 2015 in U.S. Appl. No. 14/186,403 for Cabiri.
Office Action dated Oct. 9, 2013 in IL Application No. 208634.
Office Action dated Oct. 9, 2014 in U.S. Appl. No. 13/873,335. 6 pages.
Office Action dated Oct. 9, 2020 in JP Application No. 2018-538073.
Office Action dated Sep. 13, 2017 in EP Application No. 13783458.6. 4 pages.
Office Action dated Sep. 18, 2015 in U.S. Appl. No. 13/874,085 by Cabiri. 11 pages.
Office Action dated Sep. 2, 2010 in U.S. Appl. No. 12/244,688. 9 pages.
Office Action dated Sep. 21, 2010 in U.S. Appl. No. 12/244,666. 12 pages.
Office Action dated Sep. 26, 2018 in JP Application No. 2018-535062.
Office Action dated Sep. 28, 2017 in IN Application No. 2528/DELNP/2010.
Office Action dated Sep. 29, 2013 in CN Application No. 201080040968.7. 8 pages.
Office Action dated Sep. 29, 2020 in JP Application No. 2018-538527.
Office Action dated Sep. 30, 2010 in U.S. Appl. No. 12/689,250. 10 pages.
Office Action dated Sep. 30, 2015 in U.S. Appl. No. 13/667,739 by Cabiri. 11 pages.
Office Action dated Sep. 30, 2016 in U.S. Appl. No. 13/886,867, by Cabiri.
Office Action dated Sep. 30, 2020 in CN Application No. 201780033863.0.
Office Action dated Sep. 6, 2011 in U.S. Appl. No. 12/345,818. 6 pages.
Office Action dated Sep. 8, 2017 is U.S. Appl. No. 15/510,846, by Aida.
Office Action dated Sep. 9, 2015 in U.S. Appl. No. 13/643,470 by Alon. 24 pages.
Office Action issued Aug. 17, 2021 in IN Application No. 201827027625.

(56) References Cited

OTHER PUBLICATIONS

Office Action issued Dec. 17, 2015 in CN Application No. 201380017192.0.
Office Action issued Dec. 15, 2020 in Japanese Application No. 2019-566118.
Office Action issued Feb. 19, 2016 in U.S. Appl. No. 14/553,399 by Cabiri. 7 pages.
Adler et al., "Pulse Width Modulation", Electronics in Meccano, No. 6, Published Jan. 2000, retrieved from http://www.eleinmec.com/article.asp?28 on Jul. 3, 2023.
Chan et al.; "Manufacturing Consideration in Developing a Prefilled Syringe Investigating the Effect of Headspace Pressure"; American Pharmaceutical Review, downloaded from webpage <https://www.americanpharmaceuticalreview.com/Featured-Articles/112325-Manufacturing-Consideration-in-Developing-a-Prefilled-Syringe-Investigating-the-Effect-of-Headspace-Pressure/>, May 8, 2012, 7 pages.
Communication Pursuant to Rules 161 and 162 dated Apr. 6, 2018 in EP Application No. 16784688.0. 3 pages.
Copaxone®, Innovative Drugs, Teva Pharmaceuticals, downloaded from webpage: http://tevapharm.com/copaxone/, Download date: Jan. 2009, original posting date: unknown, 3 pages.
Daikyo Crystal Zenith® polymer, Manufactured by Daikyo Seiko, Ltd. (Jun. 25, 2008). 2 pages.
Definition of Monolithic. In Merriam-Webster's online dictionary. Retrieved from https://www.merriam-webster.com/dictionary/monolithic (Year 2021).
Edwards et al., "Appendix 3 Measurement of Leakage of Tuberculin Syringes"; World Health Organization Monograph Series No. 12; BCG Vaccination, Tuberculosis Research Office World Health Organization Copenhagen; World Health Organization; Palais Des Nations, Geneva, 1953. 15 pages.
European Search Report (Partial) dated Mar. 8, 2017 in EP Application 16193157.1. 7 pages.
Examination Report dated May 8, 2017 in EP Application No. 12750951.1. 4 pages.
Extended European Search Report dated Aug. 7, 2014 in EP Application No. 1417477.4. 7 pages.
Extended European Search Report dated Feb. 12, 2018 in EP Application No. 17191756.0. 8 pages.
Extended European Search Report dated Feb. 13, 2017 in EP Application No. 16171626.1. 9 pages.
Extended European Search Report dated Feb. 23, 2015 in EP Application No. 14166596.8. 6 pages.
Extended European Search Report dated Feb. 23, 2015 in EP Application No. 14166591.9. 6 pages.
Extended European Search Report dated Jan. 20, 2017 in EP Application No. 16164319.2. 5 pages.
Extended European Search Report dated Jul. 28, 2020 in European Application No. 20172466.3. 8 pages.
Extended European Search Report dated Jul. 3, 2017 in EP Application No. 16190054.3. 7 pages.
Extended European Search Report dated Mar. 27, 2014 in EP Application No. 14154717.4. 6 pages.
Extended European Search Report dated Mar. 8, 2016 in EP Application No. 14166592.7. 11 pages.
Extended European Search Report dated Nov. 10, 2016 in EP Application No. 08808111.2. 9 pages.
Extended Search Report dated Jul. 3, 2017 in EP Application No. 16200040.0. 4 pages.
Extended Search Report dated Jul. 7, 2017 in EP Application No. 16193157.1. 14 pages.
Extended Search Report dated Jun. 13, 2016 in EP Application No. 16157430.6. 7 pages.
Int'l Preliminary Examination Report dated Apr. 5, 2016 in Int'l Application No. PCT/US2014/058433.
Int'l Preliminary Examination Report issued Apr. 5, 2016 in Int'l Application No. PCT/US2014/058446.
Int'l Preliminary Examination Report issued Apr. 5, 2016 in Int'l Application No. PCT/US2014/058456.
Int'l Preliminary Report of Patentability dated Aug. 16, 2019 in Int'l Application No. PCT/US2018/034882.
Int'l Preliminary Report on Patentability date Jan. 8, 2018 in Int'l Application No. PCT/US2016/056218.
Int'l Preliminary Report on Patentability dated Apr. 7, 2010 in Int'l Application No. PCT/IL2008/001312. 14 pages.
Int'l Preliminary Report on Patentability dated Aug. 14, 2014 in Int'l Application No. PCT/US2012/050696. 8 pages.
Int'l Preliminary Report on Patentability dated Aug. 2, 2012 in Int'l Application No. PCT/US2011/021604. 6 pages.
Int'l Preliminary Report on Patentability dated Dec. 5, 2017 in In'tl Application No. PCT/US2016/035720.
Int'l Preliminary Report on Patentability dated Feb. 5, 2019 in Int'l Application No. PCT/US2016/068058.
Int'l Preliminary Report on Patentability dated Feb. 7, 2013 in Int'l Application No. PCT/US2011/021604.
Int'l Preliminary Report on Patentability dated Feb. 7, 2013 in Int'l Application No. PCT/US2011/021605. 9 pages.
Int'l Preliminary Report on Patentability dated Jan. 18, 2018 in Int'l Application No. PCT/US2016/056210.
Int'l Preliminary Report on Patentability dated Jan. 18, 2018 in Int'l Application No. PCT/US2016/056213.
Int'l Preliminary Report on Patentability dated Jan. 18, 2018 in Int'l Application No. PCT/US2016/056223.
Int'l Preliminary Report on Patentability dated Jan. 18, 2018 in Int'l Application No. PCT/US2016/056227.
Int'l Preliminary Report on Patentability dated Jan. 9, 2011 in Int'l Application No. PCT/US2010/048556.
Int'l Preliminary Report on Patentability dated Jul. 16, 2015 in Int'l Application No. PCT/US2013/078040. 9 pages.
Int'l Preliminary Report on Patentability dated Mar. 15, 2011 in Int'l Application No. PCT/US2009/056778.
Int'l Preliminary Report on Patentability dated May 14, 2015 in Int'l Application No. PCT/US2013/065211. 10 pages.
Int'l Preliminary Report on Patentability dated Nov. 22, 2017 in Int'l Application No. PCT/US2016/068371.
Int'l Preliminary Report on Patentability dated Nov. 27, 2014 in Int'l Application No. PCT/US2013/039465. 8 pages.
Int'l Preliminary Report on Patentability dated Nov. 30, 2017 in Int'l Application No. PCT/US2016/068367.
Int'l Preliminary Report on Patentability dated Nov. 9, 2018 in Int'l Application No. PCT/US2016/056238.
Int'l Preliminary Report on Patentability dated Oct. 1, 2014 in Int'l Application No. PCT/US13/31598.
Int'l Preliminary Report on Patentability dated Oct. 9, 2014 in Int'l Application No. PCT/US2013/033118. 7 pages.
Int'l Preliminary Report on Patentability dated Sep. 1, 2011 in Int'l Application No. PCT/US2010/048556. 6 pages.
Office Action issued Feb. 28, 2014 in CN Application No. 201180006571.0. 9 pages.
Office Action issued Feb. 3, 2016 in U.S. Appl. No. 14/931,439 by Cabiri. 8 pages.
Office Action issued Jan. 8, 2013 in JP Application No. 2010-527595. 8 pages.
Office Action issued Jul. 1, 2016 in U.S. Appl. No. 15/132,740 by Cabiri. 10 pages.
Office Action issued Jul. 2, 2015 in U.S. Appl. No. 14/096,977 by Cabiri.
Office Action issued Jul. 8, 2016 in CN Application No. 201510695320.8. 11 pages.
Office Action issued Jul. 9, 2020 in EP Application No. 16828833.0.
Office Action issued May 4, 2016 in U.S. Appl. No. 15/069,080 by Cabiri. 7 pages.
Office Action issued Oct. 5, 2016 in U.S. Appl. No. 13/964,651, by Gross.
Office Action issued Sep. 27, 2020 in CN Application No. 201680088261.0.
Office Action issued Sep. 29, 2020 in JP Application No. 2019-505206.
Search Report dated Nov. 24, 2015 in EP Application No. 14166592.7.
Search Report dated Oct. 14, 2016 in CN Application No. 2014101783742.

(56) References Cited

OTHER PUBLICATIONS

U.S. Appl. No. 60/997,459, filed Oct. 2, 2007.
U.S. Appl. No. 61/192, 198, filed Sep. 15, 2008.
Office Action dated Jul. 2, 2015 in U.S. Appl. No. 14/096,977 by Cabiri.
Office Action dated Jul. 22, 2020 in Japanese Application No. 2018-538074.
Office Action dated Jul. 23, 2018 in CN Application No. 201480054177.8.
Office Action dated Jul. 29, 2013 in JP Application No. 2012-529808. 10 pages.
Office Action dated Jul. 29, 2016 in U.S. Appl. No. 14/696,644, by Cabiri. 11 pages.
Office Action dated Jul. 3, 2017 in CN Application No. 201410178374.2.
Office Action dated Jul. 31, 2015 in U.S. Appl. No. 13/521,181 by Cabiri. 11 pages.
Office Action dated Jul. 7, 2014 in U.S. Appl. No. 12/244,666 by Gross. 16 pages.
Office Action dated Jul. 7, 2016 in U.S. Appl. No. 13/892,905 by Cabiri. 19 pages.
Office Action dated Jun. 1, 2016 in CN Application No. 201380027455.6. 10 pages.
Office Action dated Jun. 10, 2016 in U.S. Appl. No. 13/964,651 by Gross.
Office Action dated Jun. 14, 2018 in U.S. Appl. No. 13/874,121, by Degtiar.
Office Action dated Jun. 17, 2016 in CN Application No. 201280068544.0. 20 pages.
Office Action dated Jun. 2, 2016 in CN Application No. 2014101783189.
Office Action dated Jun. 3, 2014 in JP Application No. 2010-527595. 8 pages.
Office Action dated Jun. 3, 2021 in CN Application No. 201880034803.5.
Office Action dated Jun. 4, 2015 in U.S. Appl. No. 13/667,739 by Cabiri. 10 pages.
Office Action dated Jun. 9, 2017 in EP Application No. 14166591.9.
Office Action dated Jun. 9, 2017 in EP Application No. 14166596.8.
Office Action dated Mar. 1, 2018 in EP Application No. 14166592.7.
Office Action dated Mar. 10, 2015 in CN Application No. 201180006567.4. 9 pages.
Office Action dated Mar. 10, 2015 in U.S. Appl. No. 12/244,666 by Gross. 17 pages.
Office Action dated Mar. 10, 2015 in U.S. Appl. No. 13/643,470 by Alon. 16 pages.
Office Action dated Mar. 13, 2017 in U.S. Appl. No. 14/372,384, by Cabiri.
Office Action dated Mar. 15, 2018 in U.S. Appl. No. 29/628,592 by Cabiri. 11 pages.
Office Action dated Mar. 22, 2017 in CN Application No. 201480054191.8.
Office Action dated Mar. 23, 2015 in JP Application No. 2012-550068. 6 pages.
Office Action dated Mar. 30, 2018 in U.S. Appl. No. 14/850,450 by Gross.
Office Action dated Mar. 5, 2014 in CN Application No. 200880117084.X. 8 pages.
Office Action dated Mar. 7, 2017 in U.S. Appl. No. 14/696,644, by Cabiri.
Office Action dated May 1, 2015 in U.S. Appl. No. 14/638,525 by Filman. 6 pages.
Office Action dated May 13, 2015 in CN Application No. 201380025566.3. 6 pages.
Office Action dated May 14, 2018 in EP Application No. 08808111.2.
Office Action dated May 16, 2012 in U.S. Appl. No. 12/615,828. 10 pages.
Office Action dated May 17, 2016 in U.S. Appl. No. 13/886,867 by Cabiri. 18 pages.
Office Action dated May 18, 2015 in U.S. Appl. No. 13/429,942 by Cabiri. 9 pages.
Office Action dated May 18, 2016 in U.S. Appl. No. 13/667,739 by Cabiri. 11 pages.
Office Action dated May 18, 2018 in EP 14166591.9.
Office Action dated May 21, 2021 in JP Application No. 2018-538073.
Office Action dated May 23, 2013 in U.S. Appl. No. 13/063,236.
Office Action dated May 23, 2014 in U.S. Appl. No. 13/472,112 by Cabiri. 9 pages.
Office Action dated May 24, 2017 in CN Application No. 201380057196.1. 20 pages.
Office Action dated May 24, 2017 in U.S. Appl. No. 13/874, 121, by Degtiar.
Office Action dated May 25, 2016 in U.S. Appl. No. 13/874,017 by Cabiri.
Office Action dated May 29, 2017 in EP Application No. 14789667.4.
Office Action dated May 3, 2012 in CN Application No. 200880117084.X. 8 pages.
Office Action dated May 31, 2016 in U.S. Appl. No. 14/593,051 by Gross.
Office Action dated May 4, 2017 in CN Application No. 201410183666.5.
Office Action dated May 5, 2015 in CN Application No. 201180006571.0.
Office Action dated Nov. 10, 2016 in U.S. Appl. No. 13/874, 121, by Degtiar.
Int'l Preliminary Report on Patentability issued Dec. 3, 2019 in Int'l Applicaiton No. PCT/US2018/034597.
Int'l Preliminary Report on Patentability issued May 26, 2015 in Int'l Application No. PCT/US2012/066036.
Int'l Preliminary Report on Patentability issued Nov. 3, 2015 in Int'l Application No. PCT/US14/35662.
Int'l Search Report (Partial), dated Dec. 20, 2016 in Int'l Application No. PCT/US2016/056247.
Int'l Search Report and Written Opinion dated Apr. 21, 2017 in Int'l Application No. PCT/US2016/068367.
Int'l Search Report and Written Opinion dated Apr. 3, 2014 in Int'l Application No. PCT/US2013/078040. 10 pages.
Int'l Search Report and Written Opinion dated Apr. 5, 2013 in Int'l Application No. PCT/US2012/050696. 13 pages.
Int'l Search Report and Written Opinion dated Aug. 12, 16 in Int'l Application No. PCT/US2016/035720.
Int'l Search Report and Written Opinion dated Aug. 14, 2018 in Int'l Application No. PCT/US2018/034882.
Int'l Search Report and Written Opinion dated Aug. 28, 2014 in Int'l Applicaiton No. PCT/US2014/035662. 15 pages.
Int'l Search Report and Written Opinion dated Aug. 5, 2013 in Int'l Application No. PCT/US2013/033118. 9 pages.
Int'l Search Report and Written Opinion dated Aug. 6, 2018 in Int'l Application No. PCT/US2018/035000.
Int'l Search Report and Written Opinion dated Dec. 12, 2014 in Int'l Application No. PCT/US2014/058433.
Int'l Search Report and Written Opinion dated Dec. 15, 2016 in Int'l Application No. PCT/US2016/056258.
Int'l Search Report and Written Opinion dated Dec. 2, 2016 in Int'l Application No. PCT/US2016/056210.
Int'l Search Report and Written Opinion dated Dec. 5, 2016 in Int'l Application No. PCT/US2016/056233.
Int'l Search Report and Written Opinion dated Dec. 8, 2016 in Int'l Application No. PCT/US2016/056227.
Int'l Search Report and Written Opinion dated Jan. 12, 2011 in Int'l Application No. PCT/US2010/048556; Written Opinion. 9 pages.
Int'l Search Report and Written Opinion dated Jan. 26, 2017 in Int'l Application No. PCT/US2016/056213.
Int'l Search Report and Written Opinion dated Jan. 7, 2014 in Int'l Application No. PCT/US2013/065211. 13 pages.
Int'l Search Report and Written Opinion dated Jul. 12, 2017 in Int'l Application No. PCT/US2016/056238.
Int'l Search Report and Written Opinion dated Jul. 31, 2014 in Int'l Application No. PCT/US2014/033598. 8 pages.

(56) References Cited

OTHER PUBLICATIONS

Int'l Search Report and Written Opinion dated Jul. 6, 2017 in Int'l Application No. PCT/US2017/022966.
Int'l Search Report and Written Opinion dated Jun. 30, 2014 in Int'l Application No. PCT/US2013/031598. 19 pages.
Int'l Search Report and Written Opinion dated Mar. 2, 2015 in Int'l Application No. PCT/US2014/058446.
Int'l Search Report and Written Opinion dated Mar. 27, 2017 in Int'l Application No. PCT/US2016/056247.
Int'l Search Report and Written Opinion dated May 13, 2009 in Int'l Application No. PCT/IL2008/001312. 16 pages.
Int'l Search Report and Written Opinion dated May 15, 2017 in Int'l Application No. PCT/US2016/068371.
Int'l Search Report and Written Opinion dated Nov. 28, 2016 in Int'l Application No. PCT/US2016/056218.
Int'l Search Report and Written Opinion dated Nov. 30, 2016 in Int'l Application No. PCT/US2016/056223.
Int'l Search Report and Written Opinion dated Nov. 5, 2012 in Int'l Application No. PCT/US2012/039465. 11 pages.
Int'l Search Report and Written Opinion dated Sep. 18, 2018 in Int'l Application No. PCT/US2018/035107.
Int'l Search Report and Written Opinion issued Apr. 26, 2017 in Int'l Application No. PCT/US2016/068049.
Int'l Search Report and Written Opinion issued Aug. 7, 2018 in Int'l Application No. PCT/US2018/034597.
Int'l Search Report and Written Opinion issued Jul. 26, 2013 in Int'l Application No. PCT/US2013/039465.
Int'l Search Report and Written Opinion issued May 27, 2015 in Int'l Application No. PCT/US2014/058456.
Int'l Search Report dated Apr. 20, 2017 in Int'l Application No. PCT/US2016/068058.
Int'l Search Report dated Apr. 26, 2010 in Int'l Application No. PCT/US2009/069552. 8 pages.
Int'l Search Report dated Aug. 11, 2010 in Int'l Application No. PCT/US2009/056778.
Int'l Search Report dated Jun. 17, 2011 in Int'l Application No. PCT/US2011/021604. 8 pages.
Int'l Search Report dated Oct. 12, 2011 in Int'l Application No. PCT/US2011/021605. 16 pages.
Int'l Search Report dated Sep. 22, 2011 in Int'l Application No. PCT/IL11/00368; Written Opinion. 8 pages.
Int'l Written Opinion dated Jul. 19, 2012 in Int'l Application No. PCT/US2011/021605.
International Preliminary Report on Patentability and Written Opinion issued Jul. 5, 2011 in International Application No. PCT/US2009/069552. 6 pages.
International Search Report dated Jul. 30, 2013 in International Application No. PCT/US2012/066036.
Liao, et al., "Research progress of needle stick protective equipment," General Nursing, 2011, No. 28, 2 pages.
Notice of Allowance dated Aug. 24, 2015 in U.S. Appl. No. 29/479,307 by Norton. 10 pages.
Notice of Allowance issued Apr. 25, 2016 in U.S. Appl. No. 14/553,399 by Cabiri. 6 pages.
Notice of Allowance issued May 11, 2016 in U.S. Appl. No. 14/931,439 by Cabiri. 6 pages.
Office Action dated Apr. 19, 2016 in U.S. Appl. No. 14/372,384, by Cabiri. 23 pages.

\* cited by examiner

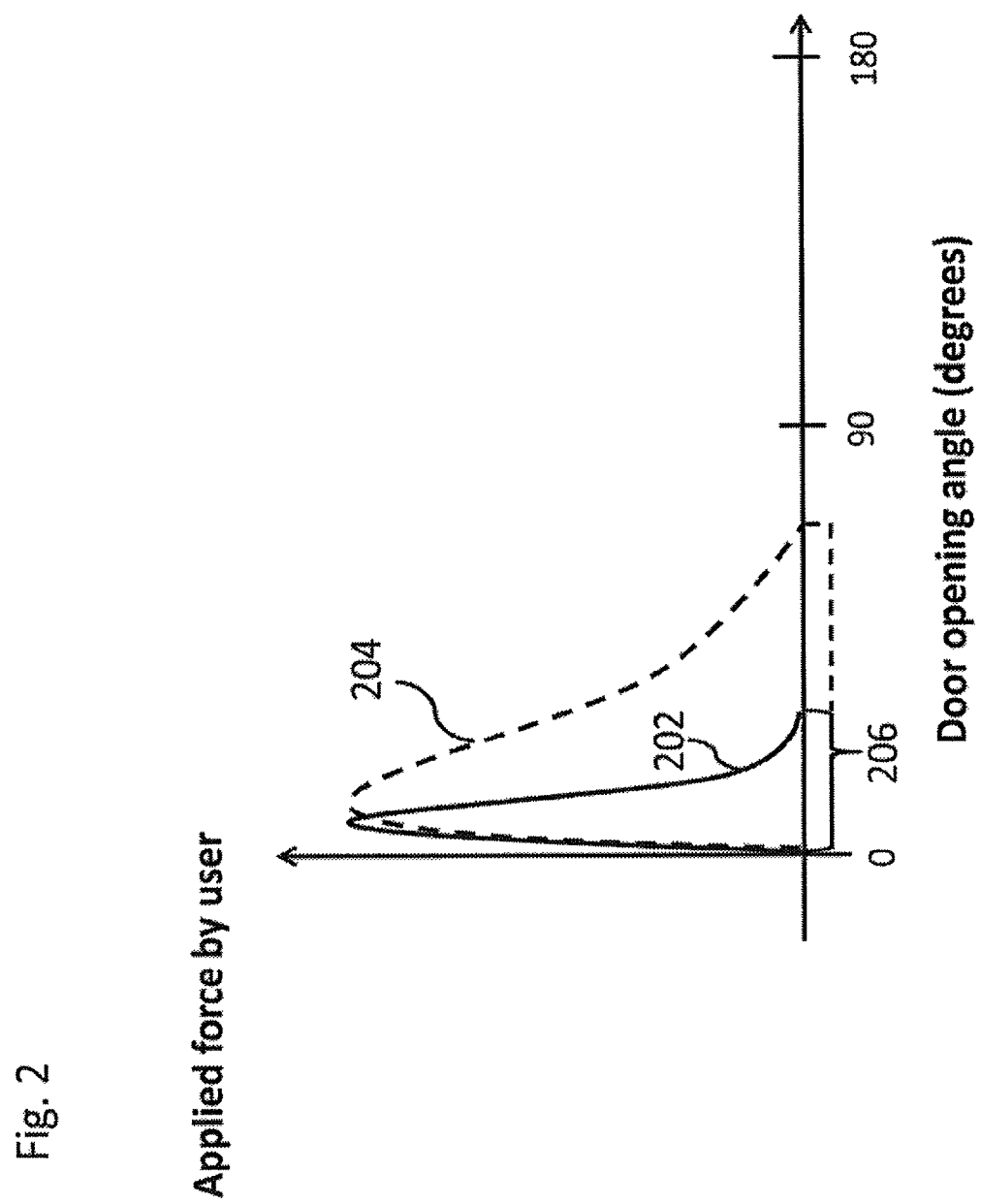

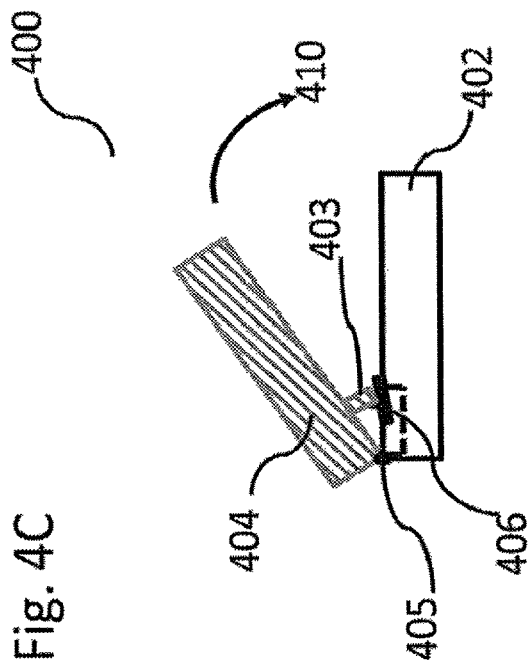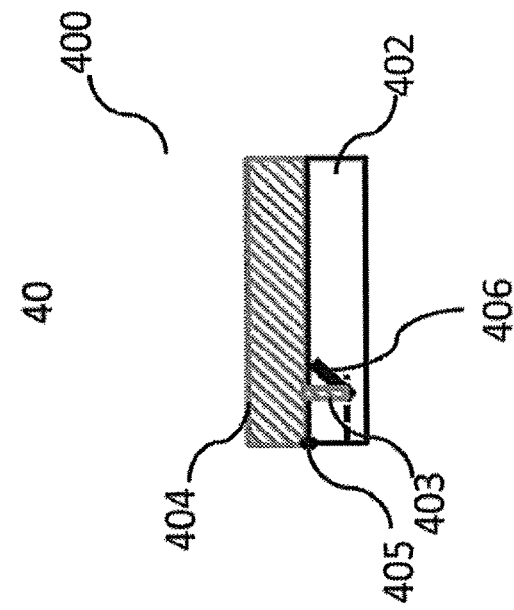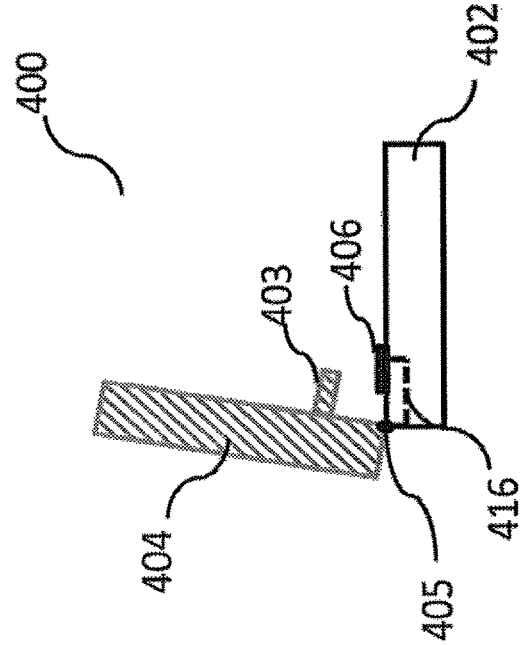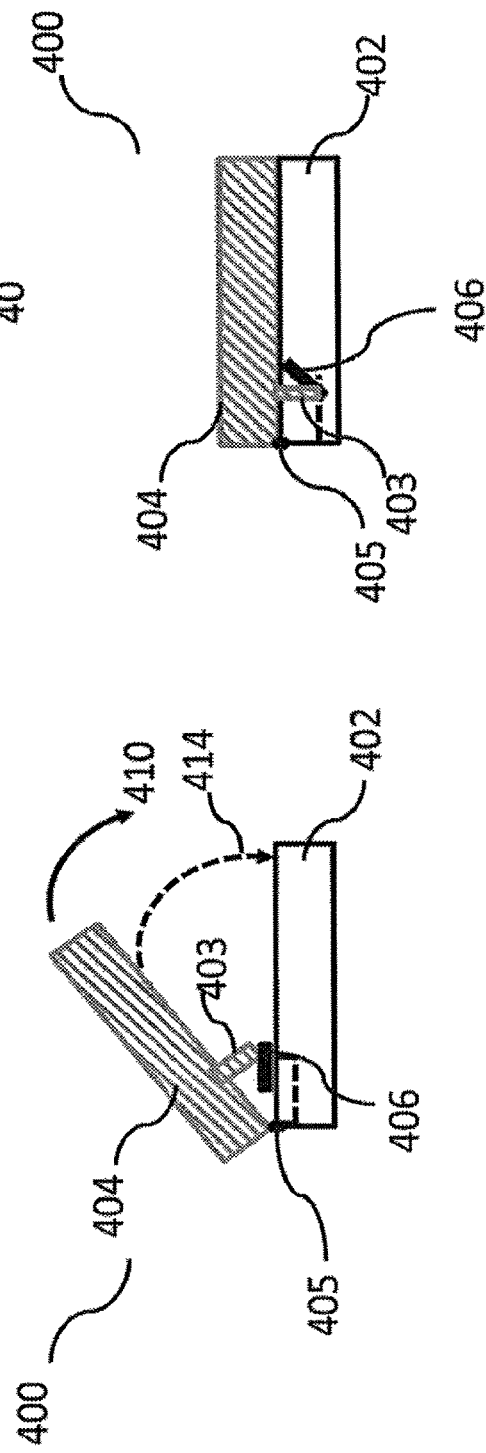

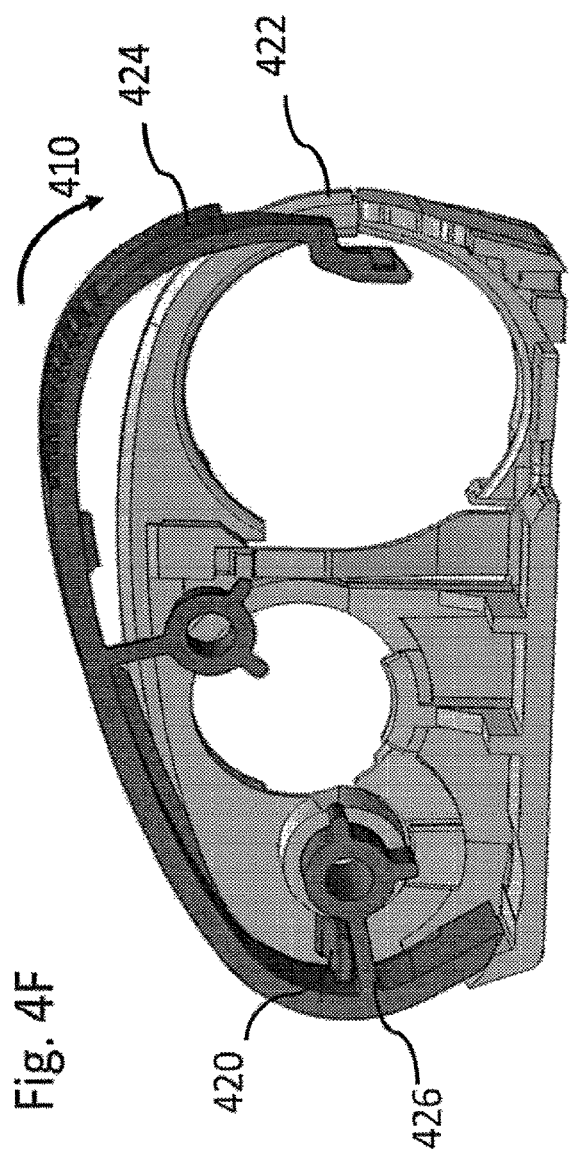
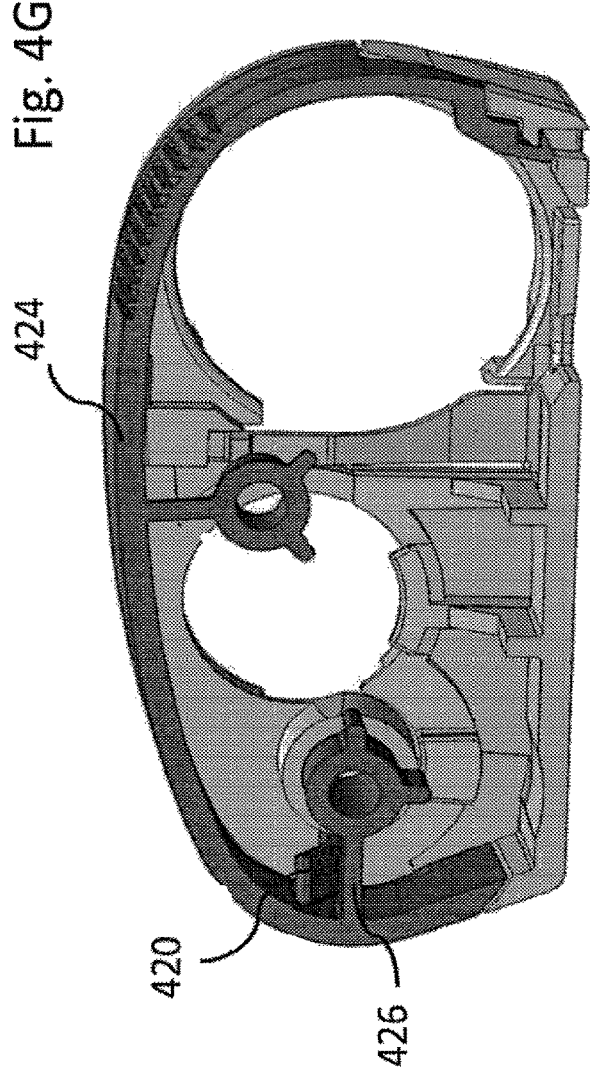

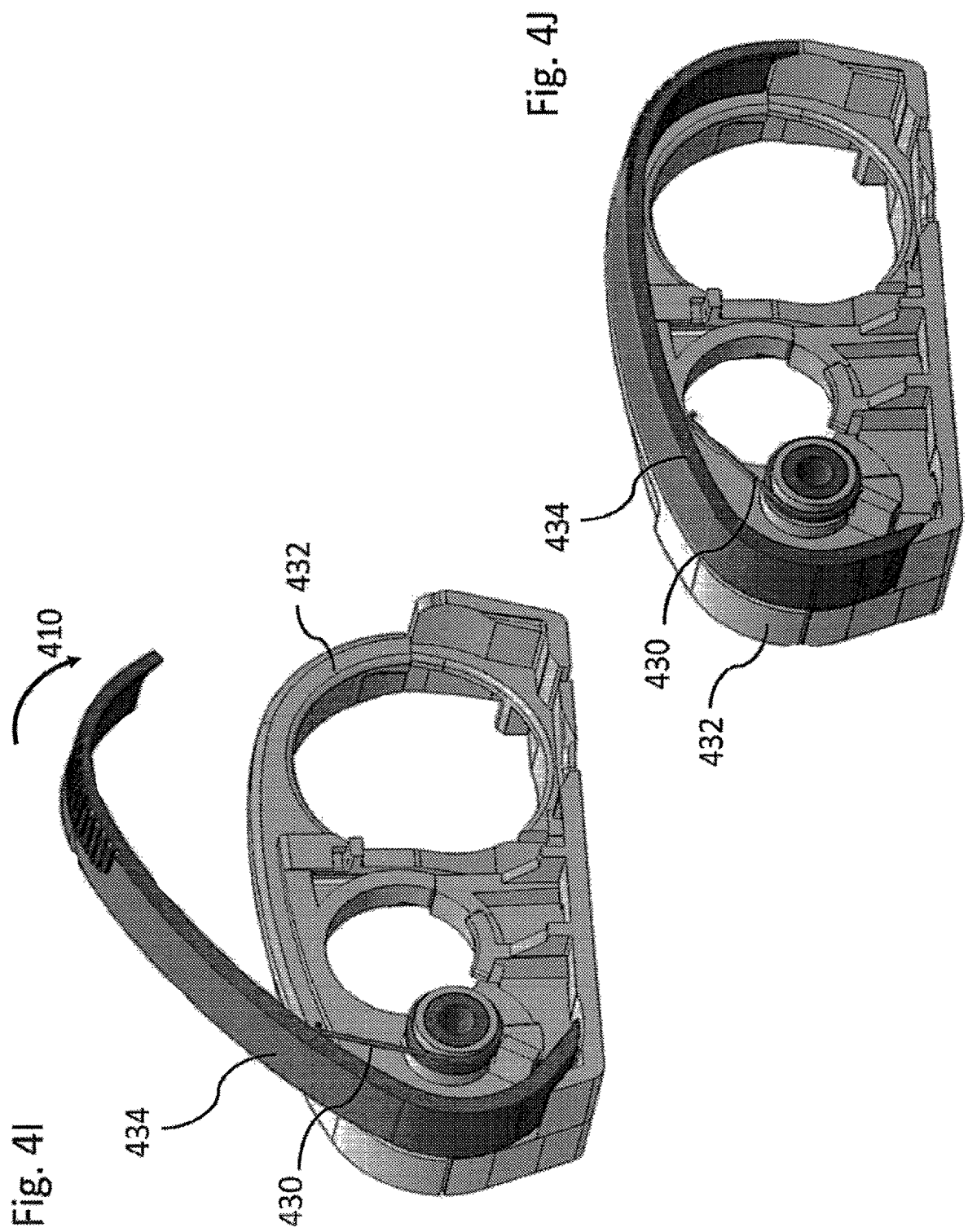

PARTIAL DOOR CLOSURE PREVENTION SPRING

CROSS-REFERENCE TO RELATED APPLICATIONS

This application is a divisional application of U.S. patent application Ser. No. 16/321,557, filed Jan. 29, 2019, which is a section 371 of International Application No. PCT/US16/068049, filed Dec. 21, 2016, which claims the benefit of U.S. Provisional Application No. 62/369,505, filed Aug. 1, 2016, the contents of which are incorporated herein by their entirety.

RELATED APPLICATIONS

This application claims the benefit of priority under 35 USC 119(e) of U.S. Provisional Patent Application No. 62/369,505 filed on Aug. 1, 2016, the contents of which are incorporated herein by reference in their entirety.

FIELD AND BACKGROUND OF THE INVENTION

The present invention, in some embodiments thereof, relates to a method for indicating the position of a door and, more particularly, but not exclusively, to a method for indicating the position of a medical device door.

SUMMARY OF THE INVENTION

Following are some examples of some embodiments of the invention:
Example 1. A drug delivery device, comprising:
housing, wherein said housing defines an opening and a chamber for a drug cartridge;
a movable door connected to said housing, having a range of movement between a fully open position and a closed position, wherein said door blocks access to said opening when said door is in said closed position;
a biasing element connected to said housing or said door, wherein said biasing element is positioned to interfere with the movement of said door by applying an opening force to open said door when said range of movement of said door is near said closed position, thus defining an exclusion zone;
a locking mechanism between said door and said housing, said locking mechanism applies a locking force on said door greater and in an opposite direction to the force applied by said biasing element.
Example 2. The device of example 1, further comprising a drug dispensing mechanism; wherein closing of said movable door engages said drug dispensing mechanism to release drug from said drug cartridge.
Example 3. The device of examples 1 or 2, wherein said movable door is connected to said housing via a hinge, wherein said locking mechanism is positioned in a distance from said hinge at the contact point between said movable door and said housing.
Example 4. The device of any of the previous examples, wherein said movable door further comprising a hinge support, wherein when said movable door is closed said hinge support pushes said biasing element with a closing force which is greater than said opening force.
Example 5. The device of example 4, wherein when said opening force is greater than said closing force said biasing element moves said movable door to a perceptibly open position by pushing said hinge support.
Example 6. The device of example 4, wherein said movable door protrudes at least 4 mm from said housing when said movable door is in said perceptibly open position.
Example 7. The device of any of examples 3 to 6, wherein said biasing element applies said opening force when during the rotation of said movable door on said hinge said door reaches the last 20-30% of said range of movement.
Example 8. The device of any of examples 3 to 6, wherein said biasing element applies said opening force in the last 20-30 degrees of the rotation of said movable door on said hinge towards a closing position.
Example 9. The device of any one of examples 3 to 8, wherein said biasing element is positioned within said hinge.
Example 10. The device of any of the previous examples, wherein said door interlocks with locking geometries on said housing for locking said door.
Example 11. The device of any of the previous examples, wherein said locking mechanism irreversibly locks said movable door.
Example 12. The device of examples 1 or 2, wherein said door is a sliding door.
Example 13. The device of any of the previous examples, wherein said biasing element is a leaf spring, and/or a torsion spring.
Example 14. The device of any of the previous example, wherein said biasing element is a deformable element configured for elasticity deforming.
Example 15. The device of any of the previous examples, wherein said door further comprises a transmission to couple between a motor of said device and a drug cartridge when said door is in said closed position.
Example 16. A method for visually indicating that a door of a drug delivery device is open, comprising:
receiving by said door a closing force to move said door;
detecting that said door is not closed;
pushing said door with an opening force by a biasing element, to a perceptibly open position; and
indicating that said door is open by identifying said perceptibly open position of said door compared to said drug delivery device housing.
Example 17. The method of example 16, wherein said indicating further comprises indicating that said door is open by identifying at least one gap between said door and said drug delivery device housing.
Example 18. The method of examples 16 or 17, wherein said receiving further comprises receiving said closing force to move said door, wherein said closing force is greater than said opening force.
Example 19. The method of anyone of examples 16 to 18, wherein said detecting further comprises detecting that said door is not locked by a locking mechanism of said door and/or housing of said drug delivery device.
Example 20. The method of anyone of examples 16 to 19, wherein said indicating further comprises indicating that said door is open by visually identifying said perceptibly open position.
Example 21. The method of anyone of examples 16 to 19, wherein said indicating further comprises indicating that said door is open by touching said door and said drug delivery device housing.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2 is a graph showing the change in the force applied by a biasing element on a medical device door as a function of the door opening angle, according to some embodiments of the invention;

FIGS. 4A-4J are schematic views depicting the closing of a medical device rotating door, according to some embodiments of the invention;

DESCRIPTION OF SPECIFIC EMBODIMENTS OF THE INVENTION

Figure 1A:
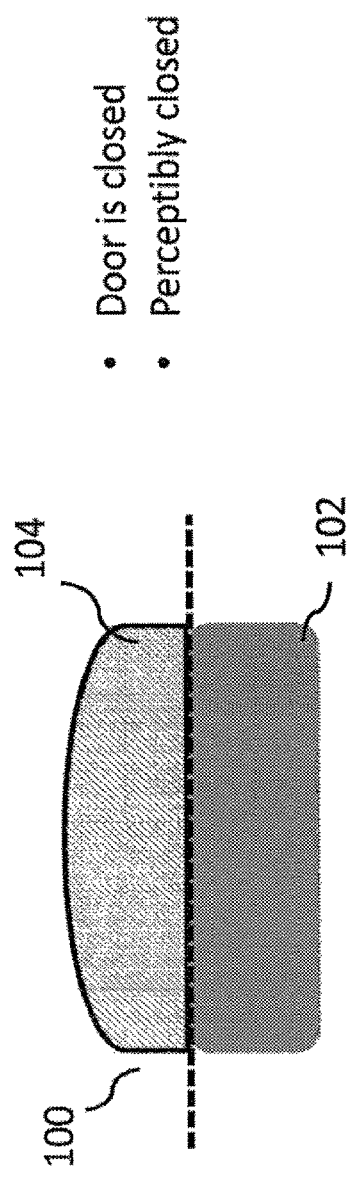
FIGS. 1A-1C are schematic front views depicting different positions of a medical device door in relation to the medical device casing, according to some embodiments of the invention.

The present invention, in some embodiments thereof, relates to a method for indicating the position of a door and, more particularly, but not exclusively, to a method for indicating the position of a medical device door.

An aspect of some embodiments relates to preventing a medical device door from being in an exclusion zone. In some embodiments, the exclusion zone is located near the closing position of the door. Alternatively, the exclusion zone is located at the last 50% of the medical device door range of movement, for example the last 5, 10, 15, 20%. In some embodiments, the exclusion zone is located at the last 25 degrees, for example last 20, 15, 10 degrees of the rotation of the device door towards a closed position.

In some embodiments, a biasing element applies a force on the door, when the door is within the exclusion zone. In some embodiments, the biasing element pushes the door open to a perceptibly open position. In some embodiments, when the door is at a perceptibly open position, a user of the device receives a clear visual indication that the door is open. Alternatively, when the door is at a perceptibly open position, a user can feel by touching the door and/or the device that the door is open. In some embodiments, for example, when the door is at a perceptibly open position the door protrudes at least 2 mm, for example 3, 4, 5, 6, 7 mm, from the device casing. In some embodiments, a potential advantage of having a biasing element which generates a limited range exclusion zone is that the biasing element does not interfere with access into the device when it pushes the door wide open. Additionally, having a device with a door wide open, for example when the door significantly protrudes out from the casing, may lead to problems during packaging and/or transportation of the device.

In some embodiments, a user applies force on the door in an opposite direction to the force applied by the biasing element, for example to move the door to a closing position. In some embodiments, the force applied by the user is larger than the opening force applied by the biasing element. In some embodiments, if the door is not further pushed by a user, then the biasing element pushes the door to the perceptibly open position.

In some embodiments, when the door is pushed to a closed position, a closing mechanism located on the door and/or on the medical device applies a greater force compared to the force applied by the biasing element. In some embodiments, the locking mechanism can be released, for example to allow opening of the door to a perceptibly open position by the biasing element. Alternatively, the locking element prevents the re-opening of the door, for example to ensure that the door remains closed, for example in case of a single use device.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1B:
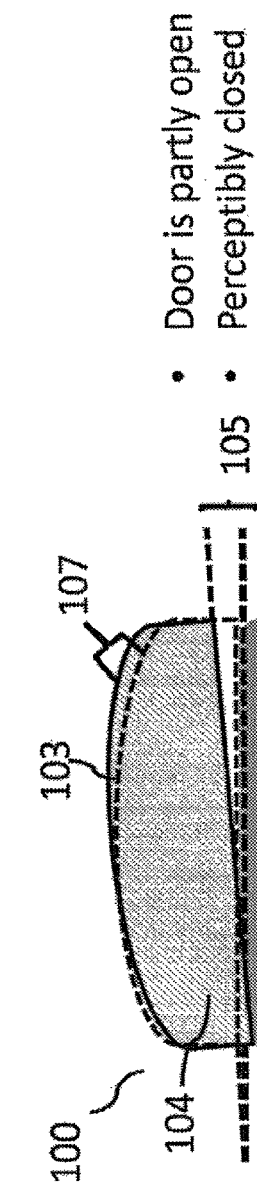
Figure 1C:
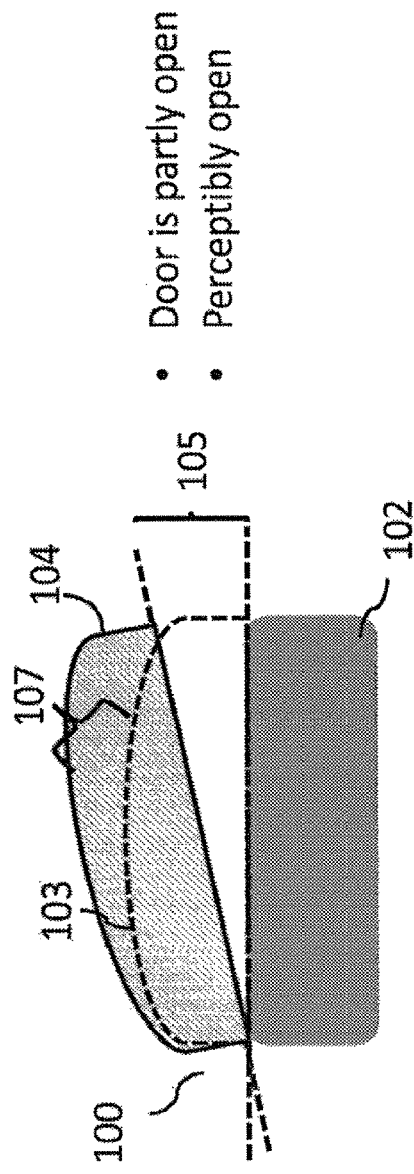

In some embodiments, a drug dispensing mechanism of a drug delivery device, for example medical device 100 in FIGS. 1A-1C, operates to dispense drug molecules only when the medical device door, for example door 104 is closed on the device housing 102, for example as shown in FIG. 1A. Optionally, when the door is closed, the door is locked by a locking mechanism. In some embodiments, when the door is fully closed, a user of the device receives a visual indication that the door is closed. In some embodiments, when the door is closed there are no visible gaps between the door and the housing. Additionally, the door and the housing form a uniform outer surface of the medical device.

In some embodiments, if the door is not closed or is in a nearly closed position, for example as shown in FIG. 1B the drug is not dispensed. In some embodiments, when the door is in a nearly closed position, a user receives a visual indication that the door is closed because, for example a gap 105 formed between the door 104 and the housing 102 is not wide enough to indicate that the door is still open, and therefore the door is perceptibly closed. In some embodiments, when the door is a nearly closed position, a gap 107 formed between the door and an upper part 103 of the housing is not visible, and cannot be identified by touching the outer surface of the medical device 100. In some embodiments, when the door is still open but is perceptibly closed, a user activates the device but a drug cannot be delivered.

In some embodiments, in order to indicate to a user that the door is not closed, the door 104 is placed in a perceptibly open position. In some embodiments, in a perceptibly open position the gap formed between the door 104 and the housing 102, for example gap 105 is wide enough to visually indicate and/or to be identified by touch that the door is not closed. In some embodiments, the gap 107 formed between the door 104 and the upper part 103 of housing 102 is also visible and can be identified by touching the outer surface of the medical device, for example the upper part of the medical device 100. In some embodiments, when a user receives the indication that the door is not closed, he can then apply more force to close the door and optionally to ensure locking of the door.

Exemplary Formation of an Exclusion Zone

According to some embodiments, in order to place the door in a perceptibly open position, an exclusion zone is formed. In some embodiments, the door is not allowed to be positioned within the exclusion zone, unless a user applies force on the door.

Reference is now made to FIG. 2, describing the formation of an exclusion zone for a door position, according to some embodiments of the invention.

According to some exemplary embodiments, a biasing element for example an elastic biasing element or a deformable biasing element applies force on the door when the door is reaching a closed position. In some embodiments, the biasing element continuously applies force on the door from a near closed position until the door reaches a closing position. In some embodiments, an exclusion zone as long as the biasing element applies force on the door. In some embodiments, the biasing element applies enough force to move the door to perceptibly open position if the total force applied on the door is in the direction of the force applied by the biasing element.

According to some exemplary embodiments, when the door is pushed from an open position to a closing position of 0 degrees between the door and the device housing, a biasing element starts to apply force on the door when the door opening degree is less than 90 degrees. In some embodiments, the biasing element applies force on the door until the door reaches an angle of 0 degrees. Optionally, the biasing element applies force on the door when the door is closed or locked.

According to some exemplary embodiments, when the door opening angle degree is less than 90 degrees, a biasing element, for example a torsion spring gradually applies force on the door. In some embodiments, for example as seen in graph 204 a user needs to apply force larger than the force applied by the torsion spring and in an opposite direction until the door is closed. In some embodiments, the increase in force applied by the user against the torsion spring is more gradual compared to the force that needs to be applied against a leaf spring as seen in graph 202. In some embodiments, the amount of force that needs to be applied by a user to close the door depends on the elasticity of the biasing element.

In some embodiments, the leaf spring starts to apply force on the door when the door angle is less than 45 degrees. In some embodiments, the leaf spring and the torsion spring form an exclusion zone 206, however the exclusion zone formed by the torsion spring is larger compared to the exclusion zone formed by the leaf spring. In some embodiments, force application in wider opening angles, for example by the torsion spring allows to form larger exclusion zones. In some embodiments, a larger exclusion zone allows for example, a better indication that the door of the medical device is open.

According to some exemplary embodiments, when the door is closed or reaches a near closing position, a locking mechanism locks the door. In some embodiments, the locking mechanism applies a force larger than the biasing element. In some embodiments, when the door is locked the force applied by the user to keep the door closed is zero, as shown in graphs 202 and 204.

Exemplary Process for Closing a Door

Figure 3:
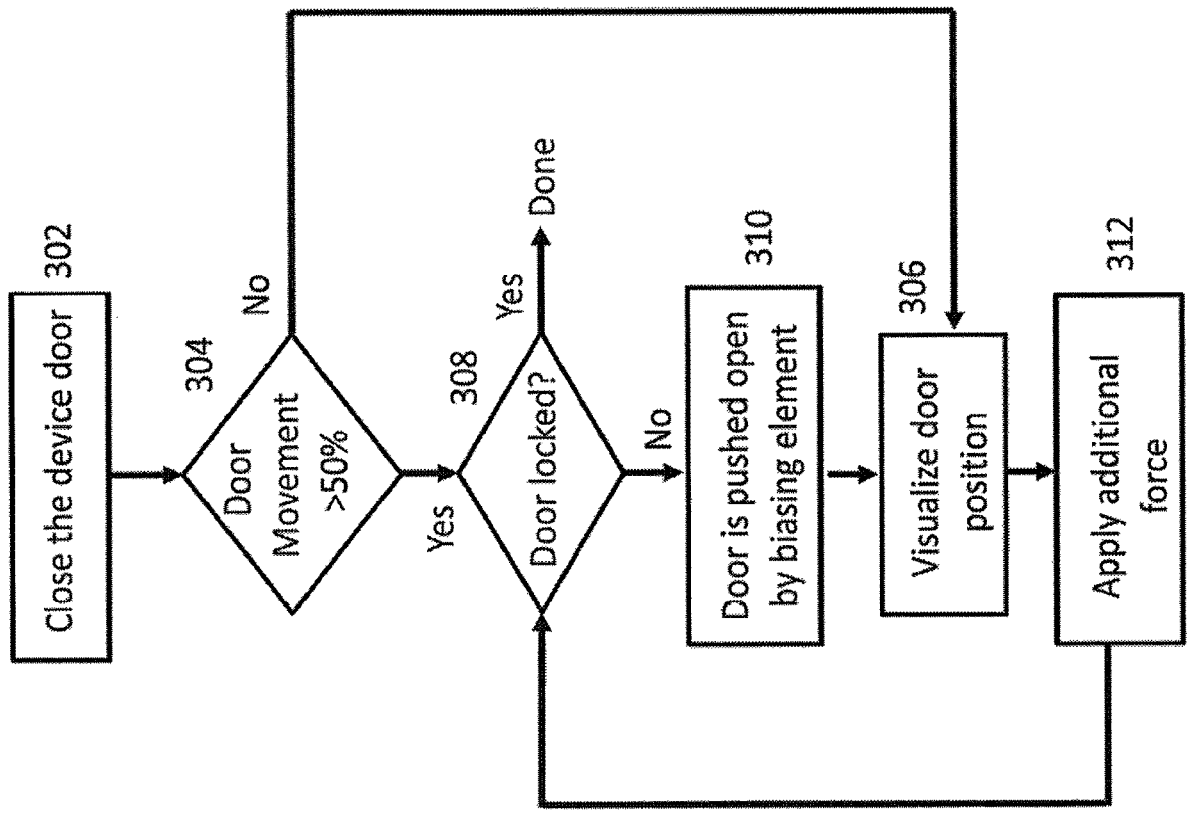
FIG. 3 is a flow chart depicting a process of closing a medical device door, according to some embodiments of the invention.

According to some exemplary embodiments, a medical device user, closes a door of the device to allow the device to operate according to a desired activation process. Reference is now made to FIG. 3, depicting a process for closing a door of a medical device, according to some embodiments of the invention.

According to some exemplary embodiments, the door is closed by a user of the medical device at 302. In some embodiments, the user closes the door by applying sufficient force on the door to allow the door movement to a closing position. In some embodiments, the force applied by the user is larger than the force applied by a biasing element. Additionally, the force applied by the user is in and in an opposite direction to the force applied by the biasing element. In some embodiments, the user applies force on the door, to move the door to a locking position.

According to some exemplary embodiments, the door movement is estimated at 304. In some embodiments, if the door moves less than 50% of the door range of movement, then the user visualizes the door position at 306, for example to receive a visual indication about the door position. In some embodiments, following the visualization of the door position, the user applies additional force to close the door at 312.

According to some exemplary embodiments, if the door moves more than 50% of the door range of movement, then the user checks whether the door is locked at 308. In some embodiments, if the door is locked, then no further actions are required. Alternatively, if the door is not locked then a biasing element pushes the door open at 310. In some embodiments, the biasing element pushes the door to a perceptibly open position.

According to some exemplary embodiments, the user visualizes the door position at 306. In some embodiments, the user visualizes that the door is at a perceptibly open position at 306, optionally by visualizing a gap between the door and the device casing, for example gap 108 shown in FIG. 1C.

According to some exemplary embodiments, if the door is visualized in a perceptibly open position, then the user applies additional force to close the door at 312. In some embodiments, the user applies a larger force on the door at 312. In some embodiments, after the additional force is applied by the user, the door movement is estimated at 304, as previously described.

Exemplary Closing of a Rotating Door

Reference is now made to FIGS. 4A-4J depicting the closing of a rotating medical device door, according to some embodiments of the invention.

According to some exemplary embodiments, medical device 400 comprises a movable door, for example rotating door 404 and housing 402, and a biasing element 406 connected to housing 402. In some embodiments, the rotating door 404 is connected to housing 402 via a hinge 405 which allows the axial rotation of the rotating door 404. In some embodiments a hinge support 403 is connected to rotating door 404. In some embodiments, the biasing element is positioned on the left side of the hinge support. Alternatively, for example when the hinge is placed on the right side of the biasing element, the hinge support is positioned on the left side of the biasing element.

According to some exemplary embodiments, for example as shown in FIG. 4A, when the rotating door 404 is in an open position, biasing element 406 is not in contact with the door or with hinge support 403, and therefore does not apply force on the door.

According to some exemplary embodiments, for example as shown in FIG. 4B, biasing element 406 is in contact with the hinge support 403, and optionally applies minimal or zero force on hinge support 403. In some embodiments, in this position, the rotating door 404 is placed in a perceptibly open position, for example a position that allows a visual indication that the door is open. In some embodiments, the biasing element 406 makes contact with the rotating door 404 or with the hinge support 403 at the last 45 degrees 414, for example last 30, 25, 20, 15, 10 degrees of the door rotation towards closing position.

According to some exemplary embodiments, for example as shown in FIG. 4C, to close the rotating door, an additional force is applied in direction 410, in an opposite direction to the force applied by the biasing element 406 on the hinge support 403. In some embodiments, if the force applied in direction 410 is zero, or is smaller than the force applied by the biasing element 406, then the rotating door 404 is pushed open, for example to the perceptibly open position shown in FIG. 4B. Alternatively, if the force applied in direction 410 is larger than the force applied by the biasing element and is applied for a sufficient time period, the rotating door 404 is closed, for example as shown in FIG. 4D. In some embodiments, when the door is closed the hinge support pushes the biasing element into a groove within housing 402. Optionally, when the door is closed a locking mechanism locks the door. In some embodiments, the locking mechanism irreversibly locks the door.

Figure 4E:
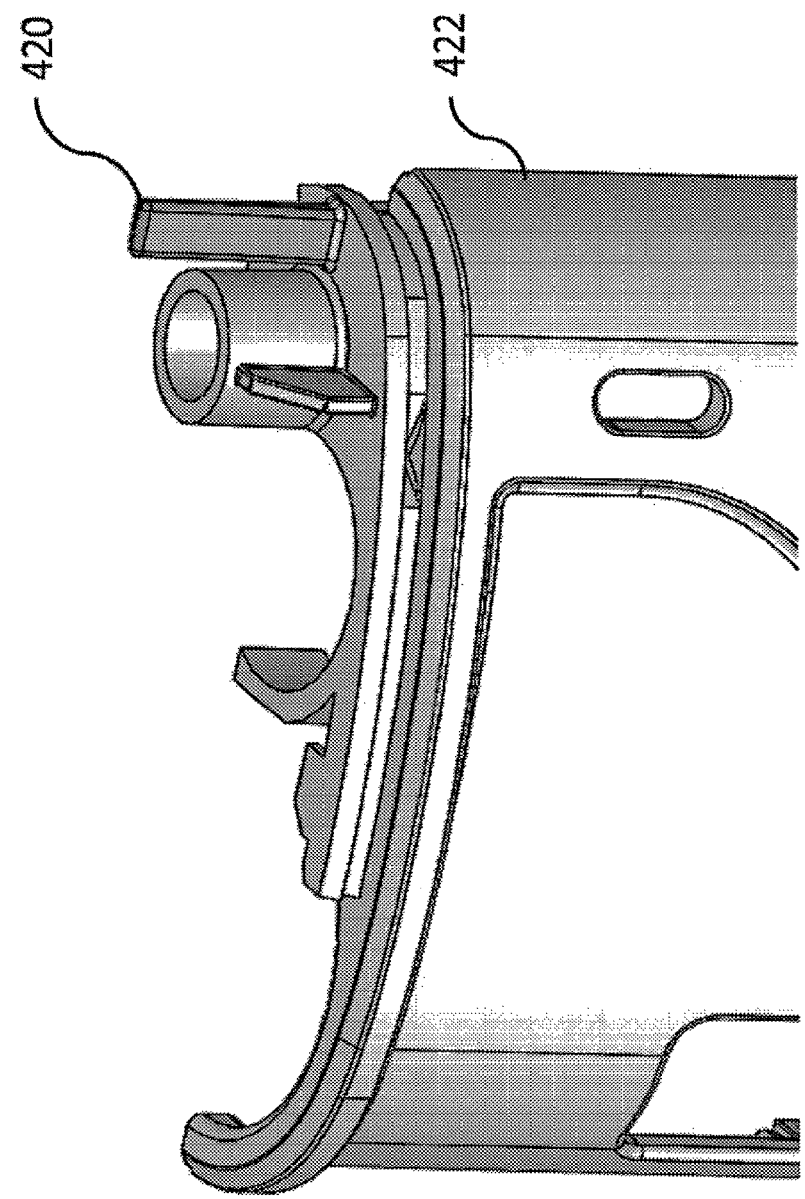

Reference is now made to FIGS. 4E-4G, depicting closing a rotating door by application of force against a biasing element in the form of a leaf spring, according to some embodiments of the invention.

According to some exemplary embodiments, for example as shown in FIG. 4E, a biasing element in the form of a leaf spring 420 is connected to housing 422. In some embodiments, when the door, for example door 424 is in perceptibly open position, leaf spring 420 is in contact with a hinge support 426 of door 424. In a perceptibly open position, the leaf spring 420 prevents the closure of door 424 unless an additional force is applied by moving the door 424 in direction 410. In some embodiments, when the door is moved in direction 410 until it reaches a closed position, the hinge support 426 applies sufficient force to bend leaf spring 420, for example as shown in FIG. 4G.

Figure 4H:
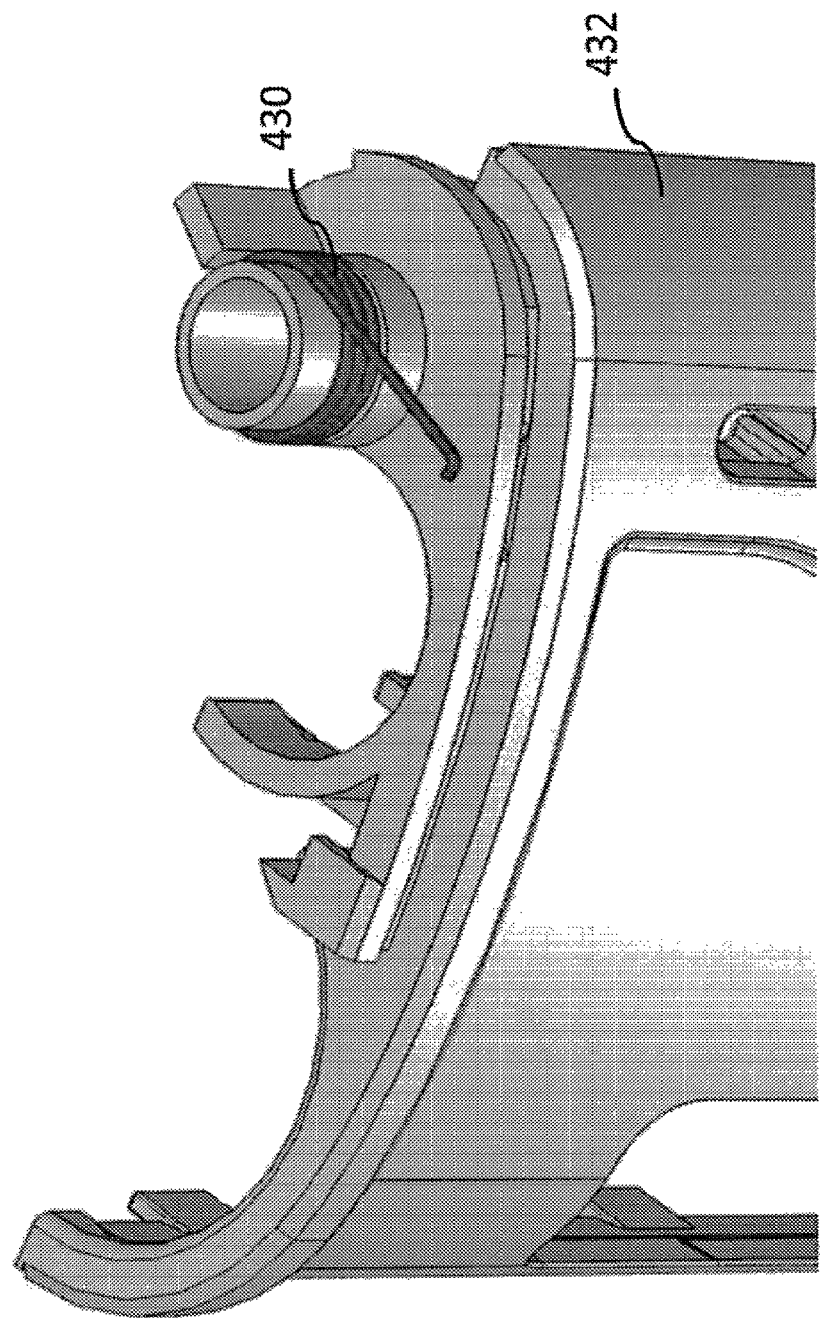

Reference is now made to FIGS. 4H-4J, depicting closing a rotating door by application of force against a biasing element in the form of a torsion spring, according to some embodiments of the invention.

According to some exemplary embodiments, for example as shown in FIG. 4H, a biasing element in the form of a torsion spring 430 is connected to housing 432. In some embodiments, when the door, for example door 434 is in perceptibly open position, torsion spring 430 is in contact with door 434. In a perceptibly open position, the torsion spring 430 prevents the closure of door 434 unless an additional force is applied by moving the door 434 in direction 410. In some embodiments, when the door is moved in direction 410 until it reaches a closed position, the door 434 applies sufficient force to bend torsion spring 430, for example as shown in FIG. 4J.

Exemplary Closing of a Sliding Door

Reference is now made to FIGS. 5A-5D depicting the closing of a sliding medical device door, according to some embodiments of the invention.

Figure 5A:
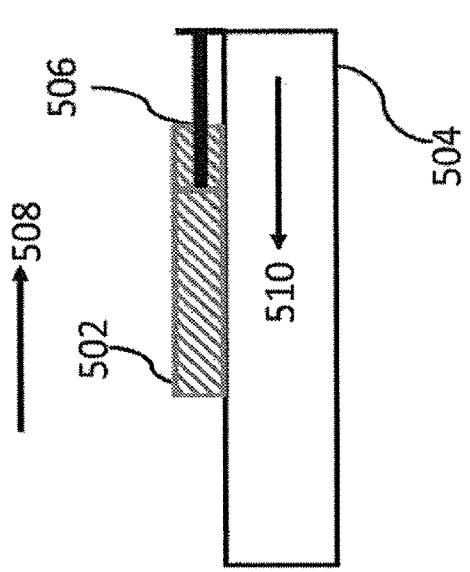
FIGS. 5A-5G are schematic views depicting the closing of a medical device sliding door, according to some embodiments of the invention.

According to some exemplary embodiments, medical device 500 comprises a sliding door 502, housing 504 and a biasing element 506 connected to housing 504. In some embodiments, for example as shown in FIG. 5A, the sliding door 502 is open and is not in contact with the biasing element 506. In some embodiments, in this position device components are inserted into the housing 504, for example a drug cartridge.

Figure 5C:
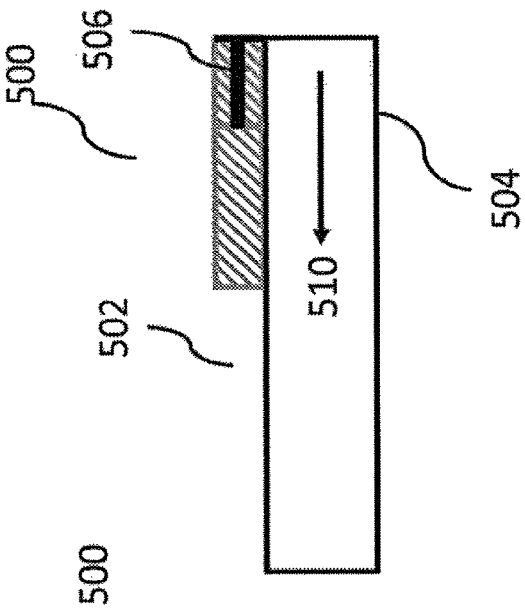
Figure 5B:
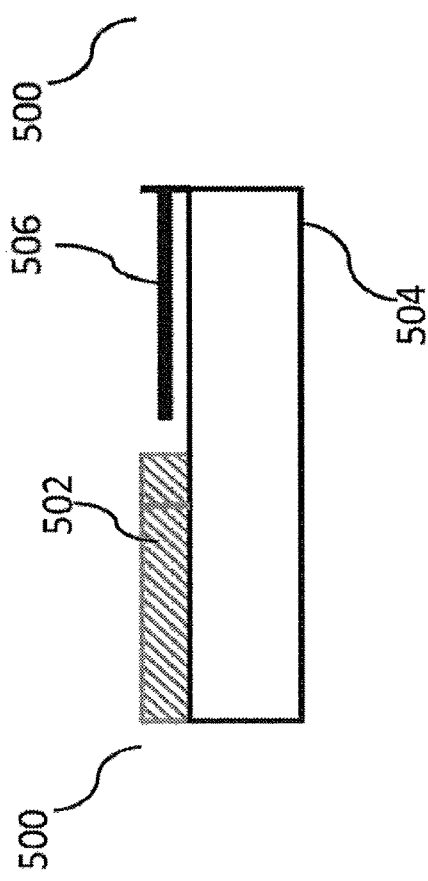

According to some exemplary embodiments, for example as shown in FIG. 5B a user applies force on the sliding door 502 in direction 508 to push the door to a closing position. In some embodiments, when the biasing element 506 applies minimal force or zero force on the sliding door 502, sliding door is positioned in a perceptibly open position.

According to some exemplary embodiments, in order to further push and close the sliding door 502, the user applies force in direction 508 in an opposite direction to the force applied by the biasing element, for example as shown in FIG. 5C. In some embodiments, the force applied by the user is larger than the force applied by the biasing element. Optionally, the user applies the force until the door is closed. In some embodiments, if the user stops applying the force before the sliding door 502 is closed, then the biasing element pushes the door in direction 510 to the perceptibly open position shown in FIG. 5B.

Figure 5D:
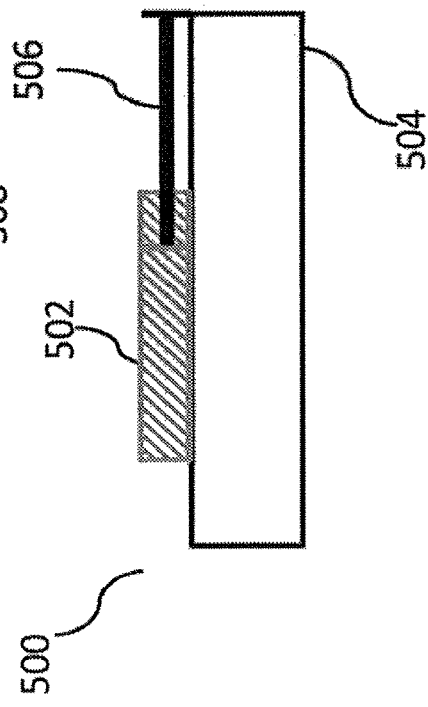

According to some exemplary embodiments, if the sliding door 502 is pushed by the user for a sufficient time period with a force larger than the force applied by biasing element, then the door is closed, for example as shown in FIG. 5D. In some embodiments, when the sliding door 502 is closed a locking mechanism placed on the door and/or on the housing 504 locks the door. In some embodiments, the locking mechanism applies force which is larger than the force applied by the biasing element, for example to prevent the opening of the door.

Figure 5G:
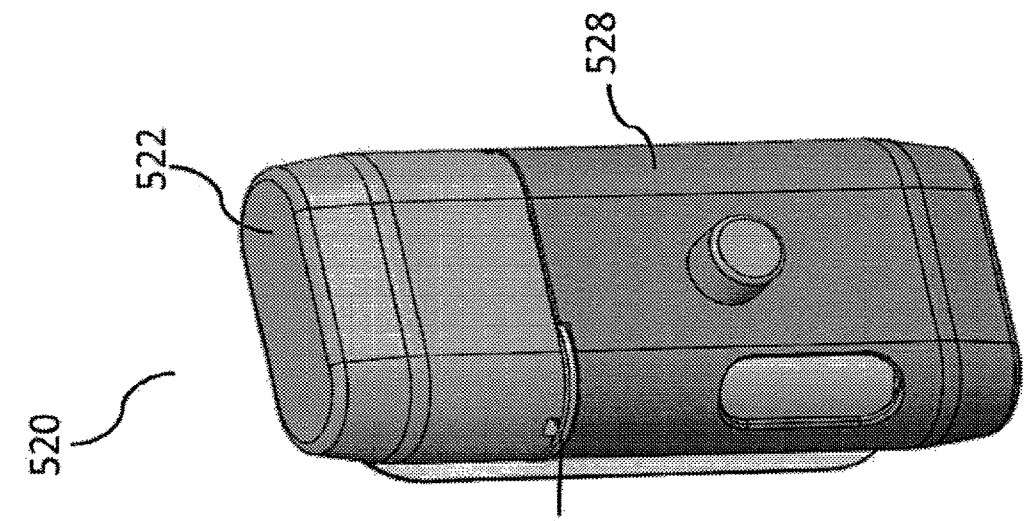
Figure 5F:
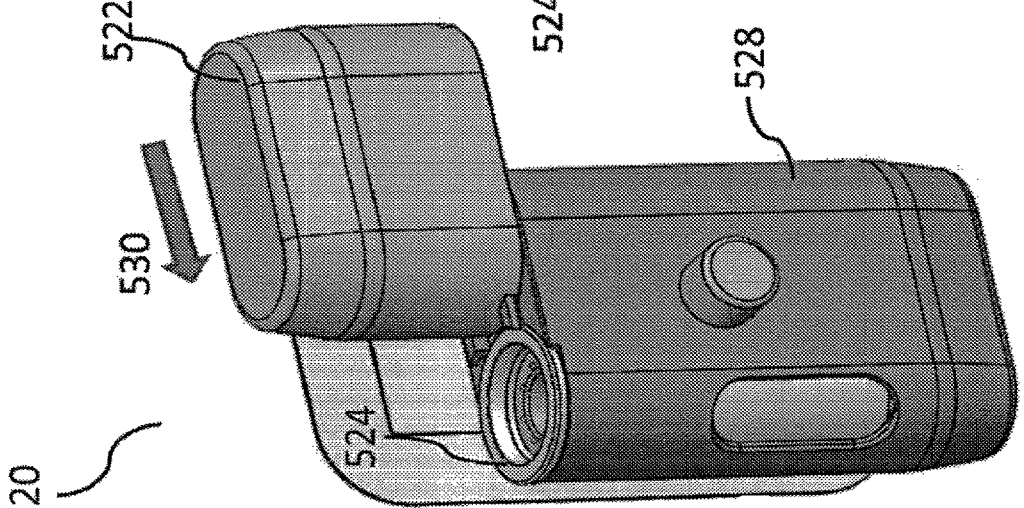
Figure 5E:
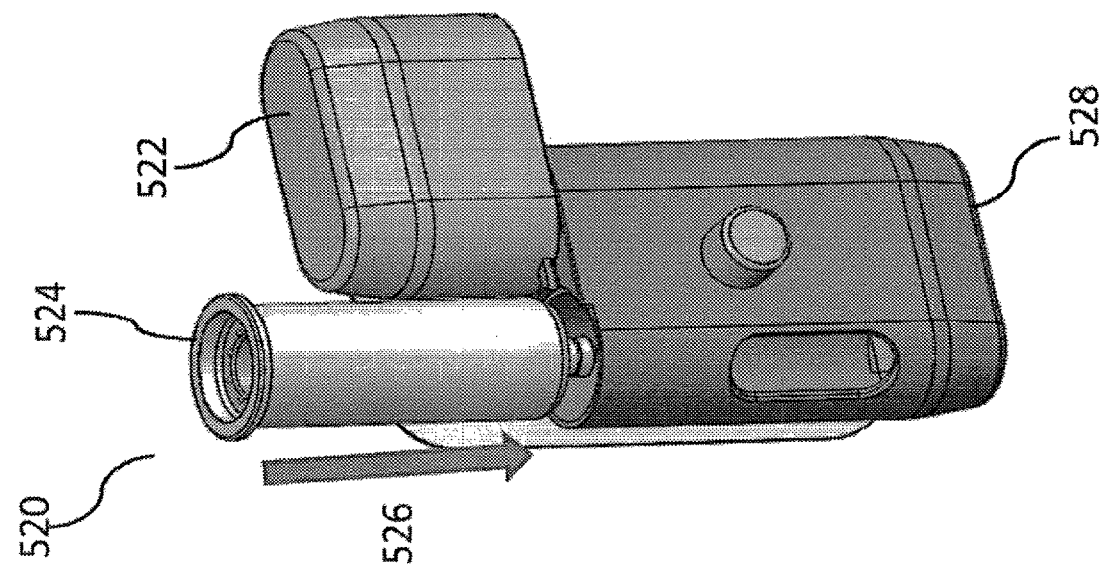

Reference is now made to FIGS. 5E-5G depicting a medical device with a sliding door in an open and a closed position, according to some embodiments of the invention.

According to some exemplary embodiments, when sliding door 522 of medical device 520 is in an open position, for example as shown in FIG. 5E, drug cartridge 524 is pushed in direction 526 into housing 528. In some embodiments, when the drug cartridge 524 is placed inside housing 528, the sliding door 522 is pushed in direction 530, for example to cover the drug cartridge 524. In some embodiments, to completely cover the drug cartridge sliding door 522 applies force against a biasing element connected to housing 528. In some embodiments, when the sliding door 522 is in a fully closed position, and is optionally locked, the drug cartridge 524 is fully covered, for example as shown in FIG. 5G. Optionally, when the sliding door 522 is locked, a drug can be delivered when medical device 520 is activated.

Exemplary Drug Delivery Device

Reference is now made to FIGS. 6A-6E depicting a drug delivery device, according to some embodiments of the invention.

According to some exemplary embodiments, a drug delivery device 600 comprising housing 602 and a movable door, for example rotating door 604 connected to housing 602 via hinge 606. In some embodiments, housing 602 defines a chamber for a drug reservoir, for example cartridge 614. In some embodiments, cartridge 614 stores drug molecules that are released when a drug dispensing mechanism of device 600 is engaged.

Figure 6A:
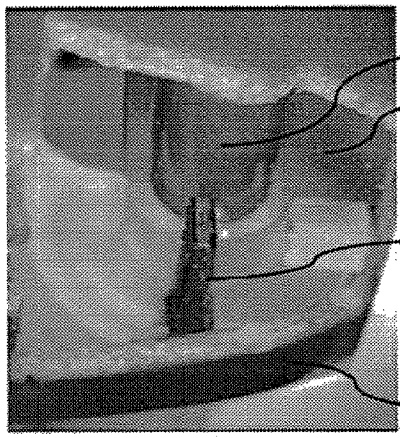
FIGS. 6A-6E are schematic views depicting different components of a medical device when the medical device door is in an open and a closed position, according to some embodiments of the invention.
Figure 6B:
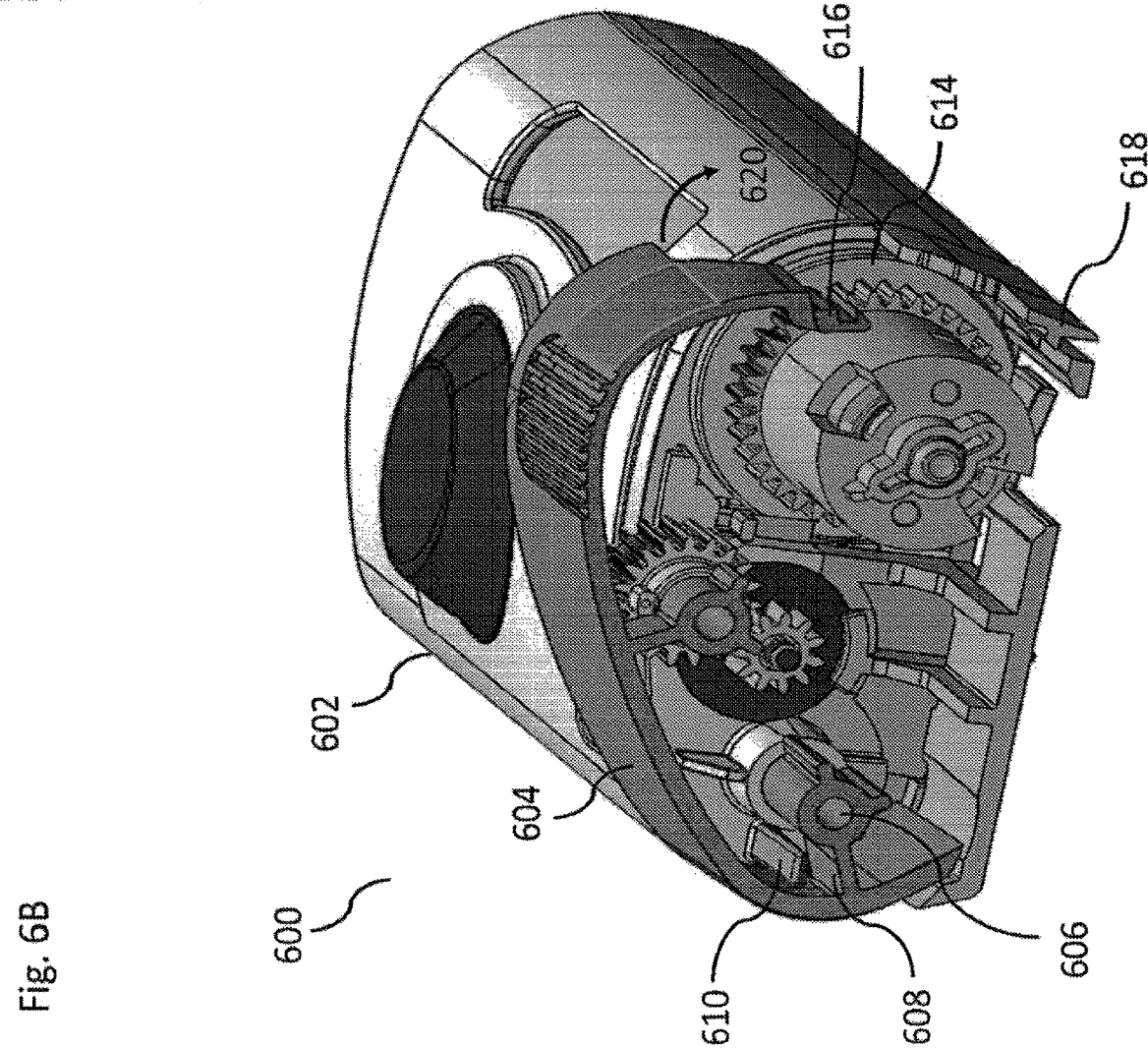
Figure 6C:
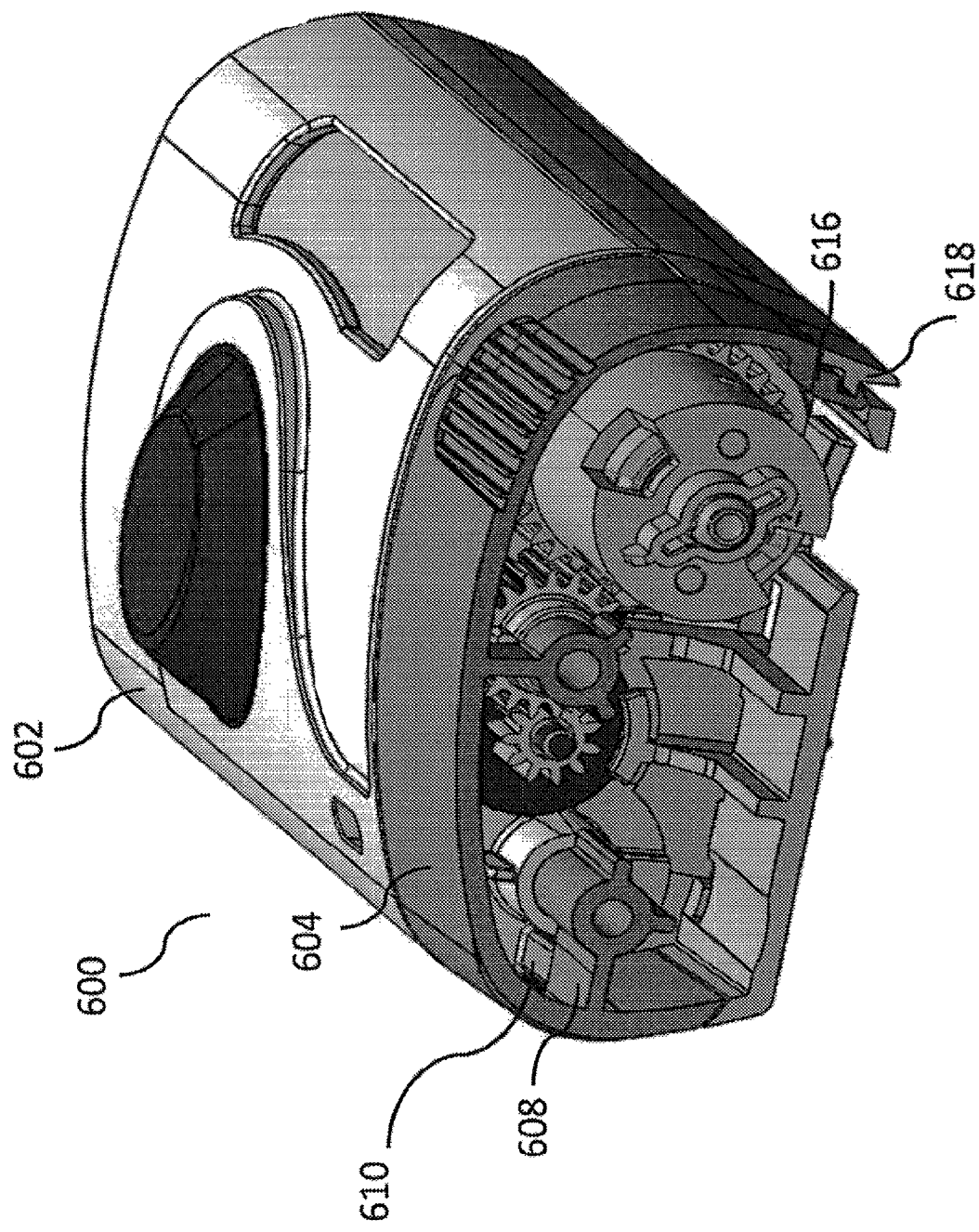
Figure 6D:
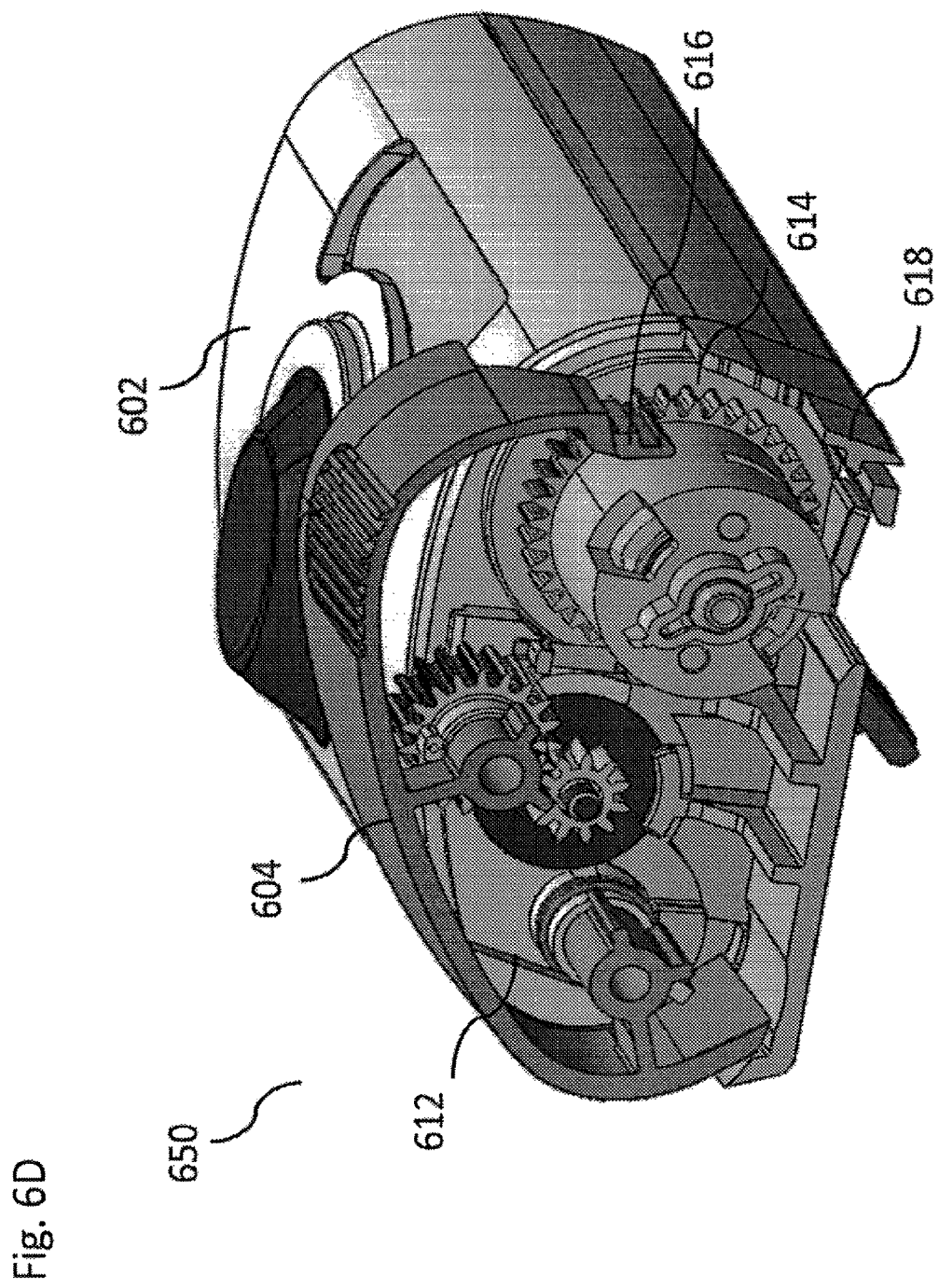

According to some exemplary embodiments, drug delivery device 600 further comprising a biasing element, for example a leaf spring 610 and/or torsion spring 612, connected to housing 602. In some embodiments, door 604 is connected to hinge 606 via hinge support 608. In some embodiments, when the door 604 is in a fully open position, for example as shown in FIG. 6A, the door is not in contact with the biasing element, and does not apply any force on the biasing element. In some embodiments, when the door 604 is pushed in direction 620 to a perceptibly open position, for example as shown in FIGS. 6B and 6D, the biasing element, for example leaf spring 610 or torsion spring 612 is in contact with the door 604. Alternatively, the biasing element is in contact with the hinge support 608. In some embodiments, when the door 604 is in a perceptibly open position, the biasing element prevents the closure of the door unless sufficient force is applied in direction 620.

According to some exemplary embodiments, when the door 604 moves in direction 620, the door applies additional force on the biasing element. Alternatively, when the door 604 moves in direction 620, the hinge support 608 applies additional force on the biasing element, for example on the leaf spring 610. Optionally, when the door moves in direction 620 an increasing force is applied on the biasing element.

Figure 6E:
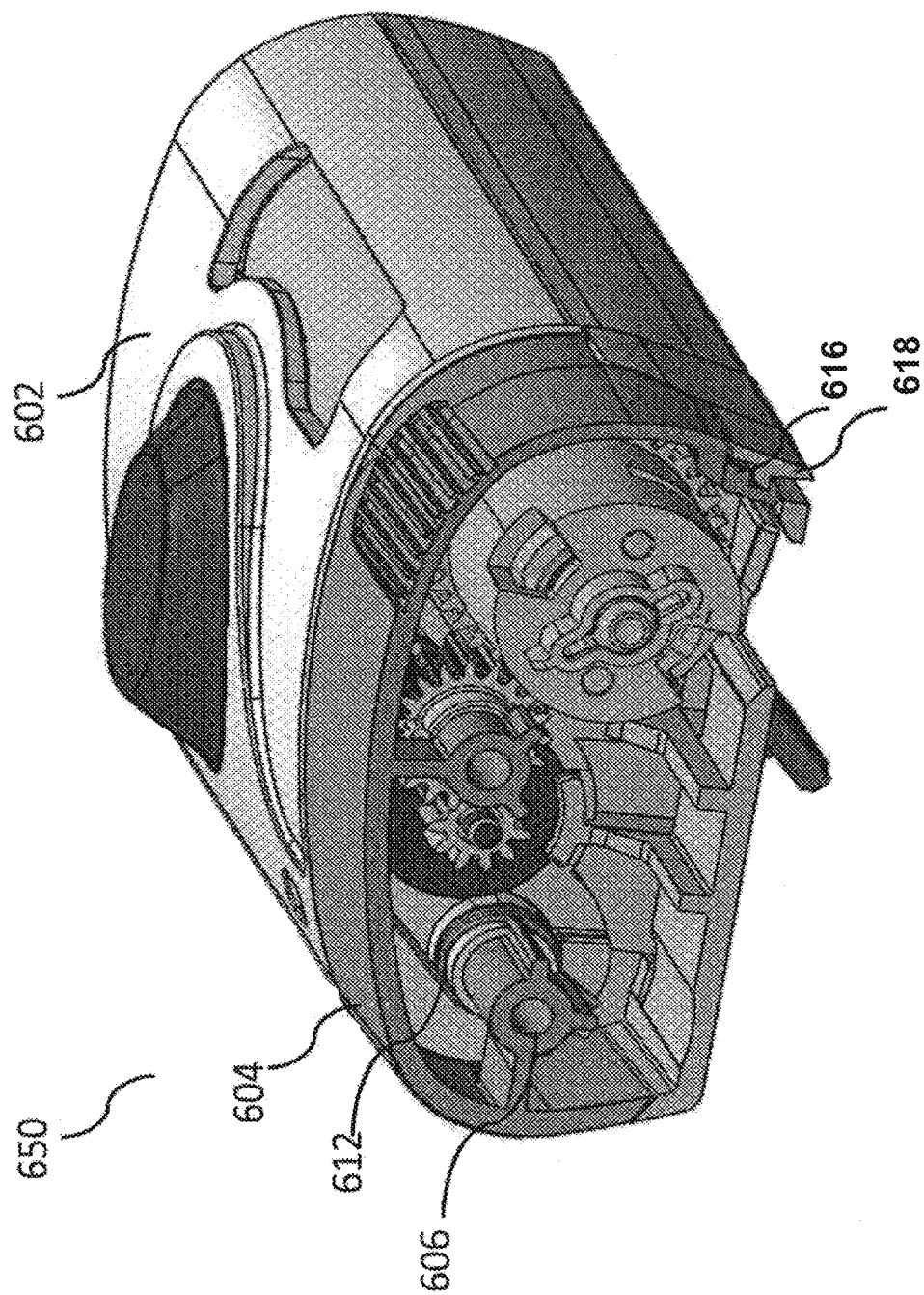

According to some exemplary embodiments, door 604 is further pushed in direction 620 with a force greater than the force applied by the biasing element in order to reach a closing position. In some embodiments, when door 604 is closed, for example as shown in FIGS. 6C and 6E, a locking mechanism placed at the distal end of the door, for example locking mechanism 616 locks door 604 to housing 602. Alternatively or additionally, locking mechanism 618 placed on housing 602 locks door 602 and/or locking mechanism 616. In some embodiments, locking mechanism is placed in the contact point between door 604 and housing 602. Optionally, the locking mechanism is placed in a distance from hinge 606. In some embodiments, the door interlocks with locking geometries on said housing.

According to some exemplary embodiments, if door 604 is not locked and there is no force applied in direction 620, the biasing element, for example leaf spring 610 or torsion spring 612 pushes the door back to the perceptibly open position, for example the perceptibly open position shown in FIGS. 6B and 6D.

According to some exemplary embodiments, both a torsion spring and a leaf spring are connected to the housing of a medical device and apply force on the door. In some embodiments, the torsion spring applies force on the door at least at the last 50% of the door range of movement towards closure. In some embodiments, the leaf spring applies additional force on the door at least at the last 30% of the door range of movement towards closure.

According to some exemplary embodiments, when door 604 remains closed or locked, a drug dispensing mechanism of the drug delivery device is engaged, for example to allow drug dispensing from cartridge 614 upon device activation. In some embodiments, when door 604 is partially open, for example when door 604 is in a perceptibly open position, drug dispensing mechanism is not engaged and drug is not released from cartridge 614 when the device is activated.

According to some exemplary embodiments, the biasing element is an elastic element made from metal. Alternatively, the biasing element is a deformable element with a limited elastic range and is made, for example from plastic or elastomer.

Exemplary Engaging Drug Dispensing Mechanism

Figure 7A:
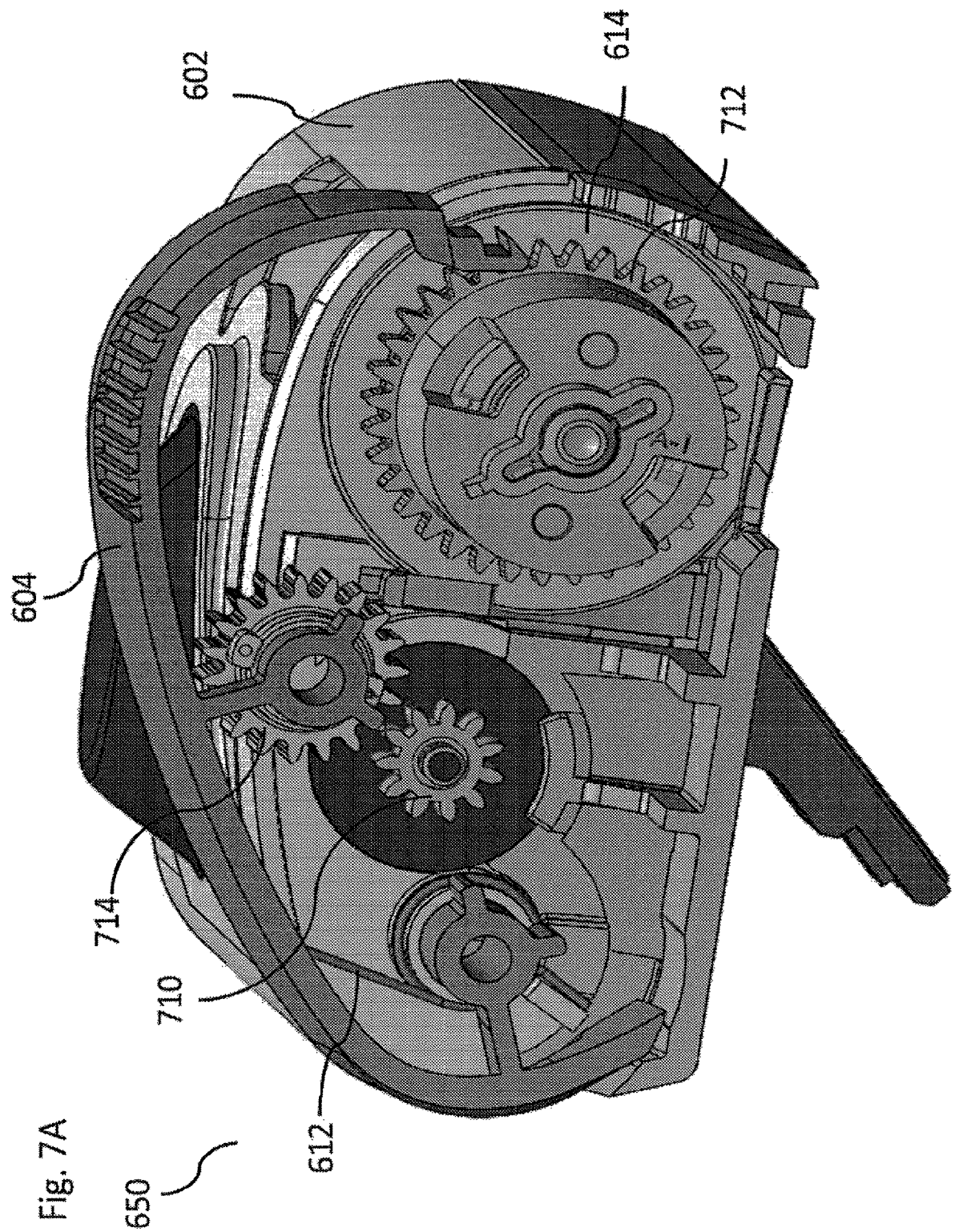
FIGS. 7A-7B are schematic views of an engagement mechanism between a motor of a medical device and a cartridge inserted into the medical device when the door of the medical device is open and when the door is closed, according to some embodiments of the invention.
Figure 7B:
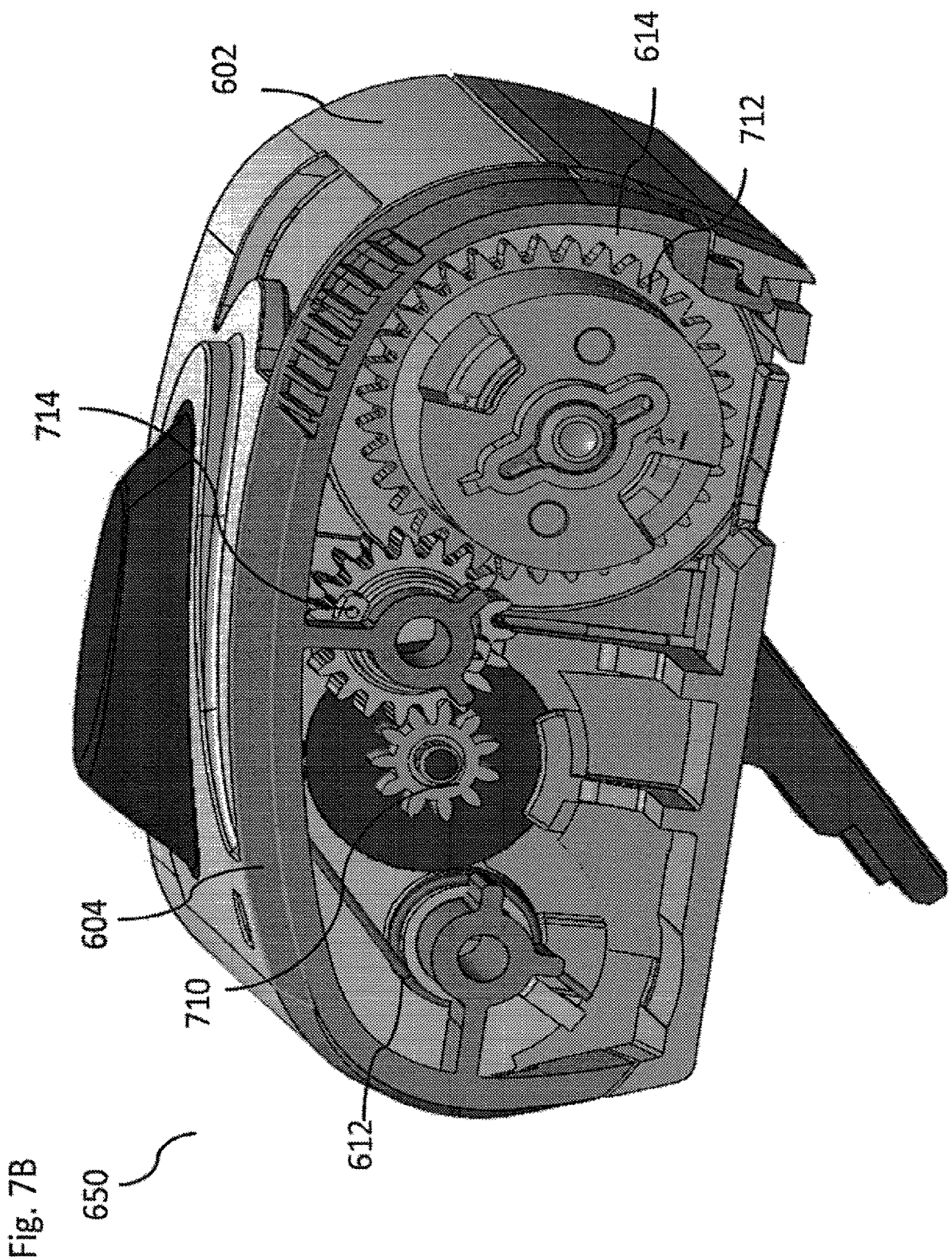

Reference is now made to FIGS. 7A and 7B, depicting the engagement of a drug dispensing mechanism, according to some embodiments of the invention.

According to some exemplary embodiments, medical device 650 comprising a motor mechanism 710 and a cartridge mechanism 712 of drug cartridge 614. In some embodiments, when door 604 is not closed for example when door is in a perceptibly open position the cartridge mechanism 712 is not engaged to motor mechanism 710. In some embodiments, when cartridge mechanism 712 is not engaged, a drug cannot be dispensed from cartridge 614, optionally even if the medical device 650 is activated by a user.

According to some exemplary embodiments, when door 604 is closed, for example by applying additional force against the biasing element 612, the cartridge mechanism 712 is engaged to motor mechanism 710. In some embodiments, a door transmission 714 is connected to door 604 and is coupled between the motor mechanism 710 and the cartridge mechanism 712, for example as shown in FIG. 7B. In some embodiments, when door 604 is closed, the door transmission 714 delivers the rotation of the motor mechanism 710 to the cartridge mechanism 712, for example to dispense drug from cartridge 614 upon medical device 650 activation.

It is expected that during the life of a patent maturing from this application many relevant biasing elements will be developed; the scope of the term biasing element is intended to include all such new technologies a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method for visually indicating that a door of a medical injector device is open, the method comprising:
    applying a closing force, which is greater than an opening force exerted on the door by a biasing element, to the door to move the door from a first position towards a closed position;
    stopping the applying of the closing force to the door, wherein the door, when the closing force is stopped, is at a second position, which is between the closed position and a last 30 degrees of rotation towards the closed position; and
    moving the door, as a result of stopping the applying of the closing force with the door at the second position and via the opening force exerted by the biasing element, from the second position to a perceptibly open position that visually indicates that the door is open, wherein:
    the perceptibly open position of the door is less than a fully opened position of the door,
    the fully opened position of the door is greater than a 30 degree rotation away from the closed position of the door, and
    the opening force is exerted on the door by the biasing element only when the door reaches the last 30 degrees of rotation towards the closed position.

2. The method of claim 1, wherein the perceptibly open position of the door has at least one gap between the door and a housing of the medical injector device.

3. The method of claim 1, wherein moving the door to the perceptibly open position comprises pushing the door to protrude at least 4 mm from a housing of the medical injector device.

4. The method of claim 1, wherein the biasing element is a deformable elastic element.

5. The method of claim 1, wherein the biasing element is a torsion spring.

6. The method of claim 1, wherein the door, when closed, is locked to a housing of the medical injector device.

7. A method for visually indicating that a door of a medical injector device is open, the method comprising:
    applying a closing force, which is greater than an opening force exerted on the door by a biasing element, to the door to move the door from a first position towards a closed position;
    stopping the applying of the closing force to the door, wherein the door, when the closing force is stopped, is at a second position, which is between the closed position and a last 30 degrees of a range of movement of the door; and
    moving the door, as a result of stopping the applying of the closing force with the door at the second position and via the opening force exerted by the biasing element, from the second position to a perceptibly open position that visually indicates that the door is open, wherein:
    the perceptibly open position of the door is less than a fully opened position of the door,
    the fully opened position of the door is 100 degrees of the range of movement of the door, and
    the opening force is exerted on the door by the biasing element only when the door reaches the last 30 degrees of the range of movement towards the closed position.

8. The method of claim 7, wherein the perceptibly open position of the door comprises at least one gap between the door and a housing of the medical injector device.

9. The method of claim 7, wherein moving the door to the perceptibly open position comprises moving the door to protrude at least 4 mm from a housing of the medical injector device.

10. The method of claim 7, wherein the biasing element is a deformable elastic element.

11. The method of claim 7, wherein the biasing element is a torsion spring.

12. The method of claim 7, wherein the door, when closed, is locked to a housing of the medical injector device.

13. The method of claim 1, further comprising inserting a container containing a medicament into the medical injector device when the door is in the fully opened position.

14. The method of claim 13, wherein the container containing the medicament is a cartridge containing the medicament.

15. The method of claim 1, further comprising injecting a medicament using a motor within the medical injector device when the door is closed.

16. The method of claim 7, further comprising inserting a container containing a medicament into the medical injector device when the door is in the fully opened position.

17. The method of claim 16, wherein the container containing the medicament is a cartridge containing the medicament.

18. The method of claim 7, further comprising injecting a medicament using a motor within the medical injector device when the door is closed.

* * * * *